US007202279B1

(12) United States Patent
Kozikowski et al.

(10) Patent No.: US 7,202,279 B1
(45) Date of Patent: Apr. 10, 2007

(54) CYCLIC DIPEPTIDES AND AZETIDINONE COMPOUNDS AND THEIR USE IN TREATING CNS INJURY AND NEURODEGENERATIVE DISORDERS

(75) Inventors: Alan P. Kozikowski, Princeton, NJ (US); Alan I. Faden, Washington, DC (US); Gian Luca Araldi, San Diego, CA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/246,307

(22) Filed: Feb. 8, 1999

Related U.S. Application Data

(63) Continuation-in-part of application No. 09/022,184, filed on Feb. 11, 1998, now abandoned.

(60) Provisional application No. 60/095,788, filed on Aug. 7, 1998.

(51) Int. Cl.
  *A61K 31/12* (2006.01)
(52) U.S. Cl. .................. 514/659; 514/661; 514/675; 514/676; 514/690; 514/691; 514/660
(58) Field of Classification Search ............... 514/19, 514/247, 408, 410, 412, 413; 544/359, 373, 544/387; 548/453, 466
  See application file for complete search history.

(56) References Cited

U.S. PATENT DOCUMENTS

| 5,661,150 | A |   | 8/1997  | Shirasaki et al. |         |
|-----------|---|---|---------|------------------|---------|
| 5,679,679 | A | * | 10/1997 | Bowen et al.     | 514/249 |
| 5,837,706 | A |   | 11/1998 | Shirasaki et al. |         |
| 5,859,001 | A |   | 1/1999  | Simpkins et al.  |         |
| 6,787,541 | B1|   | 9/2004  | Gillespie et al. |         |
| 6,916,835 | B2|   | 7/2005  | Thatcher et al.  |         |

FOREIGN PATENT DOCUMENTS

FR           1583797    * 10/1969

OTHER PUBLICATIONS

Patel et al. 'Pharmacotherapy of Cognitive Impairment in Alzheimer's Disease: A Review', J. of Geriatric Psychiatry and Neurobiology. vol. 8, pp. 81-95, Apr. 1995.*
Martin et al. "Neurodegeneration in excitotoxicity, global cerebral ischemia, and target deprivation: A perspective on the contributions of apoptosis and necrosis," Brain research bulletin, (Jul. 1, 1998) 46 (4) 281-309.*
Mattson "Pathways towards and away from Alzheimer's Disease," Nature. Aug. 5, 2004, vol. 430, pp. 631-639.*
La Ferla et al., "The Alzeheimer's αβ peptide induces neurodegeneration and apoptotic cell death in transgenic mice", Nature Genetics 1995, 9, 21-30.
Eldadah et al., "The Role of CED-3-Related Cysteine Proteases in Apoptosis of Cerebellar Granule Cells", *J. Nueroscience* 1997, 17 (16), 6105-6113.
Su et al., "Immunohistochemical evidence for apoptosis in Alzheimer's disease", *NeuroReport* 1994, 5, 2529-2533.
Smucker, "Maximizing Function in Alzheimer's Disease: What Role for Tacrine", *American Family Physician* 1996, 645-652.
Ott et al., "Complementary and Alternative Medicines for Alzheimer's Disease", *J. of Geriatric Psychiatry and Neurobiology* 1998, 11, 163-173.
Ruther et al., "Sustained improvements in patients with dementia of Alzheimer's type (DAT) 6 months after termination of Cerebrolvsin therapy", *J. Neural Transmission* 2000, 107, 815-829.
Nalbantoglu et al., "Impaired learning and LTP in mice expressing the carboxy terminus of the Alzheimer amyloid precursor protein", *Nature* 1997, 387, 500-505.
Hsiao et al., "Correlative Memory Deficits, αβ Elevation, and Amyloid Plaques in Transgenic Mice", *Science* 1996, 274, 99-102.
D'Hooge et al., "Spatial learning deficit in mice expressing human 751-amino acid β-amyloid precursor protein", *NeuroReport* 1996, 2807-2811.
Graves et al., "The Association between Head Trauma and Alzheimer's Disease", *American J. Epidemiology* 1990, 131(3), 491-501.
Plassman et al., "Documented hear injury in early adulthood and risk of Alzheimer's disease and other dementias", *Neurology* 2000, 55, 1158.
Massimo Falorni, et al. "Chiral Ligands Containing Heteroatoms. 11.[1] Optically Active 2-Hydroxymethyl Piperazines as Catalysts in the Enantioselective Addition of Diethylzinc to Benzaldehyde", *Tetrahedron Asymmetry*, vol. 4, No. 11, pp. 2389-2398, (1993).
Gamini S. Jayatilake, et al., "Metabolites from an Antarctic Sponge-Associated Bacterium *Pseudomonas aeruginosa*", *J. Nat. Prod.*, vol. 59, pp. 293-296, (1996).
List of 51 U.S. patents claiming neuroprotection.
Yakovlev, A. G., et al., "Mechanisms of Neural Cell Death: Implications for Development of Neuroprotective Treatment Strategies", The American Society for Experimental NeuroTherapeutics, Inc., vol. 1-5, pp. 5-16, Jan. 2004.
Faden, A. I., et al., "Novel small peptides with neuroprotective and nootropic properties", Journal of Alzheimer's Disease vol. 6 (2004) pp. S93-S97.

(Continued)

*Primary Examiner*—Anish Gupta
(74) *Attorney, Agent, or Firm*—Scully, Scott, Murphy & Presser, P.C.

(57) ABSTRACT

The present invention provides 4-substituted-2-azetidinone compounds, bicyclic 2-5-diketopiperazine compounds, and pharmaceutical compositions thereof that are potent, safe and effective neuroprotective agents. Due to their strong central nervous system (CNS) activity, the compounds can be used to enhance memory and to treat a variety of neurological disorders. The compounds are particularly useful for treating neurological disorders caused by, or associated with, CNS trauma.

36 Claims, 14 Drawing Sheets

OTHER PUBLICATIONS

Faden, A. I., et al., "Novel Diketopiperazine Enhances Motor and Cognitive Recovery After Traumatic Brain Injury in Rats and Shows Neuroprotection In Vitro and In Vivo", Journal of Cerebral Blood Flow & Metabolism, vol. 23, pp. 342-354.

Faden, A. I., et al., "Neuroprotective and Nootropic Actions of a Novel Cyclized Dipeptide After Controlled Cortical Impact Injury in Mice", Journal of Cerebral Blood Flow & Metabolism, Vo. 23, pp. 355-363.

Faden, A. I., et al., "Neuroprotective effects of novel small peptides in vitro and after brain injury", Laboratory for the Study of CNS Injury, Department of Neuroscience, Georgetown University of Medical Center, available at www.sciencedirect.com.

* cited by examiner

CYCLIC DIPEPTIDES AND AZETIDINONE COMPOUNDS AND THEIR USE IN TREATING CNS INJURY AND NEURODEGENERATIVE DISORDERS

1. CROSS-REFERENCE TO RELATED APPLICATIONS

This application is a continuation-in-part of application Ser. No. 09/022,184, filed Feb. 11, 1998, now abandoned, and a continuation-in-part of provisional application Ser. No. 60/095,788, filed Aug. 7, 1998. The contents of both of these applications are hereby incorporated herein by reference in their entireties.

This invention was made in part under Department of Defense Grant No. DAMD 17-93-V-3018 and CDC Grant No. R49 CCR 306634-07. The U.S. Government has certain rights in this invention.

2. FIELD OF THE INVENTION

The present invention relates to novel classes of compounds which possess substantial neurological activity, pharmaceutical compositions thereof and methods of using the compounds as neuroprotective agents and/or to enhance cognition of animals, including humans. More particularly, the invention relates to cyclic dipeptides and 4-substituted-2-azetidinone compounds, as well as homo- and heterodimers of these compounds, and methods of using compounds to treat central nervous system injuries, including stroke, brain trauma and spinal cord trauma, as well as to improve cognitive impairments caused by CNS injuries or neurodegenerative disorders such as Alzheimer's disease.

3. BACKGROUND OF THE INVENTION

Central nervous system (CNS) trauma, caused by injuries such as spinal and head injuries, are becoming more prevalent. Many of these injuries are caused by common events such as automobile accidents, serious falls, diving accidents, crushing industrial injuries and gunshot or stab wounds.

Traumatic brain or spinal cord injuries cause tissue damage through both direct and indirect, or secondary, means. Direct tissue damage is typically caused by direct mechanical injury to the tissue. Secondary tissue damage is believed to be caused by the activation of endogenous, autodestructive, neurochemical substances. Other types of acute CNS injuries, such as stroke or hypoxia, also exhibit secondary tissue damage that shares many of the secondary injury factors associated with neurotrauma.

Thyrotropin-releasing hormone (TRH), which has been identified as L-pyroglutamyl-L-histidyl-L-prolinamide, is a small peptide that has been found in various cells of the body, mainly in the neural cells of the CNS. The structure of TRH is shown below:

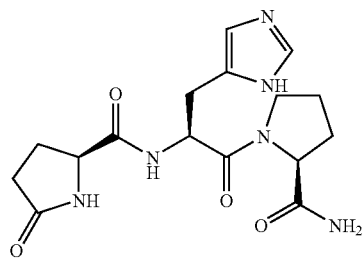

The right portion of the molecule is known to those of skill in the art as the "prolinamide" portion; the center portion of the molecule is known as the "histidyl" or "imidazole ring" portion; and the left portion of the molecule is known as the "pyroglutamyl" portion.

Endogenous TRH can act as a neurotransmitter, a neuromodulator or both. A major percentage of TRH is released from the hypothalamic nerve terminals in the median eminence to stimulate the secretion of thyroid stimulating hormone, the function for which TRH is named. TRH is also found in other areas of the CNS, and in tissues of the body such as the alimentary tract, pancreas, placenta and retina.

The function of TRH in these various areas of the body is largely unknown. However, numerous physiological actions in addition to the hypophysiotrophic function for which TRH is named have been observed. For example, TRH has autonomic and analeptic effects (Yarborouh et al., 1979, Prog. Neurobiol. 12:291–312), as well as the ability to reverse or attenuate certain physiological effects of opioids (Holaday et al., 1978, Life Sci. 22:1537–1543), neurotensin (Prange et al., 1979, In: Central Nervous System Effects of Hypothalamic Hormones and Other Peptides, pp. 75–96, Raven, N.Y.), leukotrienes (Lux et al., 1983, Nature 302: 822–824) and platelet-activating factor (Lux et al., 1983, Circ. Shock 10:262). TRH administration reduces neurological deficits after traumatic spinal cord injury in cats (Faden et al., 1981, N. Engl. J. Med. 305:1063–1067). Additionally, treatment with TRH has also been found to improve electrical activity and neurological recovery in cats subjected to brainstem compression (Fukuda et al., 1979, Folia Pharmacol. Jpn. 75:321–331), and to shorten postconcussional behavioral suppression following head impact trauma in mice (Manaka and Sano, 1978, Neurosci. Lett. 8:255–258). One of the advantages of TRH is that it acts as a physiological opiate antagonist without affecting nociception.

However, as a drug to treat CNS trauma, TRH has several drawbacks. The major disadvantage is that TRH is very rapidly metabolized. As a consequence, high doses and/or continuous infusions are necessary for effective treatment. The short plasma half-life (4–5 min.) is most likely due to rapid in vivo degradation or metabolism of the peptide at both the prolineamide and pyroglutamyl portions of the molecule. Cleavage of the pyroglutamyl moiety of TRH by peptidases causes the formation of the metabolite cyclo-histidyl-proline-diketopiperazine. Deamidation of TRH results in the formation of the free acid TRH-OH.

Because of the drawbacks of TRH, two classes of compounds have been studied: cyclic dipeptides and azetidinones. The cyclicdipeptides [also known as bicyclic 2,5-dioxopiperazines; bicyclic 2,5-diketopiperazines; cyclo (dipeptides); or dipeptide anhydrides] are generally based upon observed metabolite products of TRH. The azetidones are based upon TRH in which the pyroglutamyl portion has been replaced with 2-azetidinone.

Cleavage of the amino-terminal pyroglutamic acid from TRH by pyroglutamyl aminopeptidase followed by cyclization of His-Pro-NH$_2$ yields the metabolite cyclo(His-Pro) (Prasad & Peterkofsky, 1976, J. Biol. Chem. 251:3229–3234; Prasad et al., 1977, Nature 268:142–144). Cyclo(His-Pro), as well as certain other cyclic dipeptides have been tested for biological activity. However, of those tested, only four—cyclo(His-Pro), cyclo(Leu-Gly), cyclo (Tyr-Arg) and cyclo(Asp-Pro)—exhibit any biological activity in mammals (for a review of the activities of various cyclic dipeptides see Prasad et al., 1995, Peptides 16(1): 151–164, and the references cited therein). Of these, none has been identified as being useful as a neuroprotective agent or to treat neurological disorders such as Alzheimer's disease.

GB 2 127 807 discloses certain 2-5-diketo-piperazines useful for inhibiting the development of tolerance to the cataleptic effect after repeated administration of neuroleptics, and for the treatment of memory disturbance, tardive dyskenesias and Parkinson's disease. DD 153208 discloses certain 2,5-diketopiperazines that are potentially useful as synthetic ergot alkaloids. DD 246767 discloses the cyclic dipeptide cyclo(Lys-Pro), and pharmaceutical compositions thereof, that are useful as stimulants of nerve fiber growth and nerve cell differentiation and maintenance. JP 63135386 describes certain hydroxyproline cyclic dipeptides useful as plant growth accelerators. However, none of these compounds has been identified as being useful as a neuroprotectant or to treat neurological disorders such as Alzheimer's disease.

Modification of one or more of the constituent amino acids of TRH has led to the development of various TRH analogues, some of which are highly resistant to enzymatic degradation and are far more potent than TRH with respect to CNS activity (Metcalf, 1982, Brain Research 486:389–408). The advantage of such compounds in CNS injury is that they may permit utilization of lower drug concentrations and single parenteral dosing (Faden, "Role of TRH and Opiate Receptor Antagonists in Limiting Central Nervous System Injury," In: Physiological Basis for Functional Recovery in Neurological Disease, S. Waxman, Ed., Vol. 47, Raven, N.Y., 1987, pp. 531–546).

However, only certain classes of these compounds are effective in protecting against tissue damage. For example, compounds CG3509 (Faden and Jacobs, 1985, Neurology 35:1331–1334) and CG3703 (Faden et al., 1988, Brain Research 448:287–293), which have substitutions for the pyroglutamyl moiety improve outcome following traumatic spinal cord injury (McIntosh et al., 1988, Am. J. Physiol. 254:R785–R792). In contrast, compound MK-771 (Faden and Jacobs, 1985 supra), which has modifications at both ends of the tripeptide, and compound RX-77368 (Faden et al., 1988, supra) which has a modification only at the prolineamide moiety, proved ineffective even at very high doses. Moreover, many of these analogues have been found to have centrally active effects such as endocrine, analeptic and autonomic effects (Faden, 1989, Brain Res. 486:228–235; Faden et al., 1993, J. Neurotrauma 10(2): 101–108).

Faden, 1989, Brain Research 486:228–235 describes a peptidase-resistant TRH analogue called YM-14673, in which the pyroglutamyl portion of TRH is replaced with a 2-azetidinone moiety. The structure of YM-14673 is shown below:

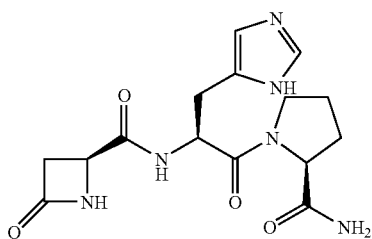

Analogue YM-14673 is longer acting (8–36 times) and has substantially greater potency (10–100 times) with regard to central facilitating activity than TRH (Faden et al., 1989, supra). Treatment with YM-14673 also improved chronic neurological recovery in rats following trauma (Faden, 1989, supra).

U.S. Pat. No. 5,686,420 to Faden describes peptidase-resistant TRH analogues in which the imidazole ring of the histidyl moiety has been replaced with an imidazole substituted with one or more trifluoromethyl, nitro or halogen groups and/or in which the pyroglutamyl moiety has been replaced with a different ring structure, such as a 2-azetidinone moiety. An exemplary compound is an analogue of YM-14673 in which the imidazole ring is di-substituted at the 2 and 4 carbons with iodo groups. The structure of this diiodo analogue of YM-14673 is shown below:

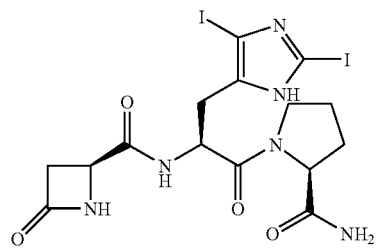

Additional TRH analogues in which the pyroglutamyl moiety has been replaced with a 2-azetidinone moiety are described in European Patent EP 0 123 444. However, while effective, these 2-azetidinone TRH analogues exhibit undesirable autonomic and endocrine side-effects.

Thus, there remains a need in the art for compounds that are effective in treating neurological disorders, especially TRH analogues that are effective in reducing secondary brain and spinal cord injury in patients suffering from CNS injuries, that do not affect nociception, that are not rapidly metabolized by protases in vivo, and that have less endocrine and/or autonomic effects than TRH. There is also a need for compounds that improve cognitive function, especially following acute or chronic brain injuries. Accordingly, these are objects of the present invention.

4. SUMMARY OF THE INVENTION

These and other objects are furnished by the present invention, which in one aspect provides novel classes of compounds that are resistant to proteases and which exhibit strong central nervous system (CNS) activity. Due in part to this CNS activity, the compounds are useful for enhancing cognitive function, particularly memory function following acute or chronic brain injuries, and/or for treating CNS injuries, neurodegenerative disorders such as Alzheimer's disease, or neurological disorders caused by trauma or ischemia to the central nervous system.

The first class of compounds of the invention includes cyclic dipeptides [also known as bicyclic 2,5-dioxopiperazines; bicyclic 2,5-diketopiperazines; cyclo(dipeptides); or dipeptide anhydrides] having the structural formula (Ia):

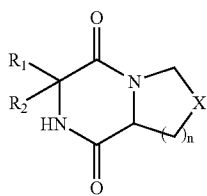

(Ia)

wherein:
n is an integer from 0 to 3;
X is selected from the group consisting of —S—, —O—, —NR— and —CH$_2$—;
R$_1$ and R$_2$ are each independently selected from the group consisting of —H, —OR, —SR, —NRR, —NO$_2$, —CN, —C(O)OR, —C(O)NRR, —C(NR)NRR, trihalomethyl, halogen, (C$_1$–C$_6$) alkyl, substituted (C$_1$–C$_6$) alkyl, (C$_2$–C$_6$) alkenyl, substituted (C$_2$–C$_6$) alkenyl, (C$_1$–C$_6$) alkynyl, substituted (C$_2$–C$_6$) alkynyl, (C$_5$–C$_{20}$) aryl, (C$_5$–C$_{20}$) substituted aryl, 5–20 membered heteroaryl, substituted 5–20 membered heteroaryl, (C$_6$–C$_{26}$) arylalkyl, substituted (C$_6$–C$_{26}$) arylalkyl, 6–26 membered heteroarylalkyl and substituted 6–26 membered heteroarylalkyl,
or R$_1$ and R$_2$ taken together are —CH$_2$—(CH$_2$)$_m$—CH$_2$—, where m is an integer from 0 to 6;
each alkyl, alkenyl, alkynyl, aryl, arylalkyl, heteroaryl and heteroarylalkyl substituent is independently selected from the group consisting of —R, —OR, —SR, —NRR, —CN, —NO$_2$, —C(O)OR, —C(O)NRR, —C(S)NRR, —C(NR)NRR, —NR—C(NR)—R, —NR—C(NR)—OR, —NR—C(NR)—SR, —NR—C(NR)—NRR, halogen and trihalomethyl; and
each R is independently selected from the group consisting of —H, (C$_1$–C$_6$) alkyl, (C$_2$–C$_6$) alkenyl, (C$_2$–C$_6$) alkynyl, (C$_5$–C$_{20}$) aryl, (C$_6$–C$_{26}$) arylalkyl, 5–20 membered heteroaryl and 6–26 membered heteroarylalkyl.

In another embodiment of the invention, the cyclic dipeptides are compounds according to the above-described structure (Ia) wherein at least one of R$_1$ and R$_2$ is a moiety which acts as a free radical trap or an inhibitor of the enzyme nitric oxide synthase (NOS).

A second class of compounds of the invention includes TRH analogues that differ from TRH at one, two, or all three portions of the TRH molecule. However, the most significant differences are at the pyroglutamyl and histidyl portions. In the TRH analogues of the invention, a 2-azetidinone moiety replaces the pyroglutamyl moiety and the imidazole ring of the histidyl moiety is replaced with another substituent. Moreover, the prolineamide portion of the TRH analogues of the invention moiety may contain heteroatoms such as O, N or S and/or from 4 to 7 ring atoms. Thus, in one embodiment of the invention, the TRH analogues are 2-azetidinone compounds having the structural formula (Ib):

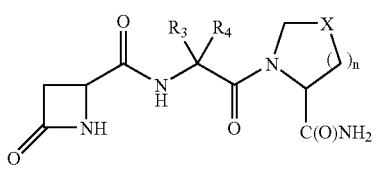

(Ib)

wherein:
n is as previously defined for structure (Ia);
X is as previously defined for structure (Ia);
R$_3$ and R$_4$ are each independently selected from the group consisting of —H, —CN, —C(O)OR', —C(O)NR'R', —C(NR')NR'R', trihalomethyl, (C$_1$–C$_6$) alkyl, substituted (C$_1$–C$_6$) alkyl, (C$_2$–C$_6$) alkenyl, substituted (C$_2$–C$_6$) alkenyl, (C$_2$–C$_6$) alkynyl, substituted (C$_2$–C$_6$) alkynyl, (C$_5$–C$_{20}$) aryl, (C$_5$–C$_{20}$) substituted aryl, 5–20 membered heteroaryl, substituted 5–20 membered heteroaryl, (C$_6$–C$_{26}$) arylalkyl, substituted (C$_6$–C$_{26}$) arylalkyl, 6–26 membered heteroarylalkyl and substituted 6–26 membered heteroarylalkyl,
or R$_3$ and R$_4$ taken together are —CH$_2$—(CH$_2$)$_p$—CH$_2$—, where p is an integer from 0 to 6;
each alkyl, alkenyl, alkynyl, aryl, arylalkyl, heteroaryl and heteroarylalkyl substituent is independently selected from the group consisting of —R', —OR', —SR', —NR'R', —CN, —NO$_2$, —C(O)OR', —C(O)NR'R', —C(S)NR'R', —C(NR')NR'R', —NR'—C(NR')—R', —NR'—C(NR')—OR', —NR'—C(NR')—SR', —NR'—C(NR')—NR'R', halogen and trihalomethyl; and
each R1 is independently selected from the group consisting of —H, (C$_1$–C$_6$) alkyl, (C$_2$–C$_6$) alkenyl, (C$_2$–C$_6$) alkynyl, (C$_5$–C$_{20}$) aryl, (C$_6$–C$_{26}$) arylalkyl, 5–20 membered heteroaryl and 6–26 membered heteroarylalkyl.

In one embodiment of the invention, the TRH analogues are compounds according to the above-described structure (Ib), with the proviso that:

(i) when n is 1; X is —CH$_2$—; and one of R$_3$ or R$_4$ is —H; then the other of R$_3$ or R$_4$ is not:

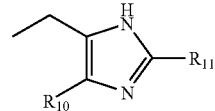

where R$_{10}$ is —CF$_3$, —NO$_2$ or a halogen and R$_{11}$ is —H, or R$_{10}$ is —H and R$_{11}$ is —CF$_3$, or R$_{10}$ and R$_{11}$ are each independently a halogen; and/or (ii) when n is 1, 2 or 3; X is —CH$_2$—; and one of R$_3$ or R$_4$ is —H, (C$_1$–C$_6$) alkyl, (C$_2$–C$_6$) alkenyl or (C$_2$–C$_6$) alkynyl; then the other of R$_3$ or R$_4$ is not —(CH$_2$)$_a$—R″, where a is 0, 1, 2 or 3 and R″ is selected from the group consisting of imidazolyl, imidazol-5-yl, imidazolyl independently substituted with one or more —CF$_3$, trihalomethyl, —NO$_2$ or halogen groups, imidazol-5-yl independently substituted with one or more —CF$_3$, trihalomethyl, —NO$_2$ or halogen groups, 2,4-dihalo-[1H]-imidazol-5-yl and 2,4-diiodo-[1H]-imidazol-5-yl.

In another embodiment of the invention, the TRH analogues are compounds according to the above-described structure (Ib) wherein at least one of R$_3$ and R$_4$ is a moiety which acts as a free-radical trap or an inhibitor of the enzyme nitric oxide synthase (NOS).

A third class of compounds of the present invention includes disulfide-bridged dimers having the structural formula (Ic):

(Ic)

wherein:
—S—S— represents a disulfide bridge;
each r is independently an integer from 1 to 6; and
A and B are each independently selected from the group consisting of:

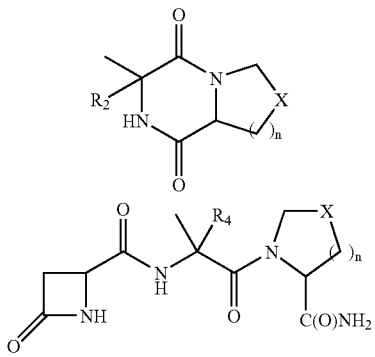

wherein:
each n, which may be the same or different, is as previously defined for structure (Ia);
each X, which may be the same or different, is as previously defined for structure (Ia);
each $R_2$, which may be the same or different, is as previously defined for structure (Ia); and
each $R_4$, which may be the same or different, is as previously defined for structure (Ib). The dimers may be homodimers, where A and B are each diketopiperazines or TRH analogues, or may be heterodimes where one of A or B is a diketopiperazine and the other is a TRH analogue.

In another aspect, the present invention provides pharmaceutical compositions comprising one or more compounds according to the invention and a pharmaceutically acceptable carrier, excipient or diluent. Such a preparation can be administered in the methods of the invention.

In still another aspect, the invention provides a method for the treatment of neurological disorders, particularly neurological disorders caused by brain and/or spinal cord trauma or stroke. The method involves administering to an animal subject, including humans, an amount of at least one compound according to the invention, or a pharmaceutical composition thereof, effective to treat the neurological disease. Neurological diseases which can be treated according to the methods of the invention include, but are not limited to, brain and spinal cord trauma, stroke and neurodegenerative disorders such as Alzheimer's disease.

In a final aspect, the invention provides a method for enhancing the cognitive function of animals, including humans. The method involves administering to an animal subject an amount of at least one compound according to the invention, or a pharmaceutical composition thereof, effective to enhance cognition of the subject. The method is particularly useful for enhancing both learning and working memory function, especially following acute or chronic brain injuries.

4.1 Definitions

As used herein, the following terms shall have the following meanings:

"Alkyl:" refers to a saturated branched, straight chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In preferred embodiments, the alkyl groups are $(C_1-C_6)$ alkyl, with $(C_1-C_3)$ being particularly preferred.

"Alkenyl:" refers to an unsaturated branched, straight chain or cyclic hydrocarbon radical having at least one carbon—carbon double bond. The radical may be in either the cis or trans conformation about the double bond(s). Typical alkenyl groups include, but are not limited to, ethenyl, propenyl, isopropenyl, butenyl, isobutenyl, methallyl, cyclobutenyl, pentenyl, isopentenyl, cyclopentenyl, hexenyl, cyclohexenyl, vinylidene, propylidene, isopropenyl, isopropylidene, butenylidene, tert-butenyl and the like. In preferred embodiments, the alkenyl group is $(C_2-C_6)$ alkenyl, with $(C_2-C_3)$ being particularly preferred.

"Alkynyl:" refers to an unsaturated branched, straight chain or cyclic hydrocarbon radical having at least one carbon—carbon triple bond. Typical alkynyl groups include, but are not limited to, ethynyl, propynyl, butynyl, isobutynyl, pentynyl, hexynyl and the like. In preferred embodiments, the alkynyl group is $(C_2-C_6)$ alkynyl, with $(C_2-C_3)$ being particularly preferred.

"Substituted Alkyl Alkenyl or Alkynyl:" refers to an alkyl, alkenyl or alkynyl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

"Aryl:" refers to an unsaturated cyclic hydrocarbon radical having a conjugated π electron system. Typical aryl groups include, but are not limited to, penta-2,4-diene, phenyl, naphthyl, acenaphthyl, anthracyl, azulenyl, chrysenyl, indacenyl, perylenyl, phenanthrenyl, picenyl, pyrenyl, pyranthrenyl, rubicenyl and the like. In preferred embodiments, the aryl group is $(C_5-C_{20})$ aryl, with $(C_5-C_{10})$ being particularly preferred.

"Substituted Aryl:" refers to an aryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl where each R is independently —H, alkyl, alkenyl, alkynyl, aryl, arylalkyl, heteroaryl or heteroarylalkyl, as defined herein.

"Heteroaryl:" refers to an aryl moiety wherein one or more carbon atoms are replaced with another atom, such as N, P, O, S, As, Se, Si, Te, etc. Typical heteroaryl groups include, but are not limited to, radicals derived from acridine, carbazole, β-carboline, chromene, cinnoline, furan, imidazole, indazole, indole, indolizine, isobenzofuran, isochromene, isoindole, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, acridarsine, arsanthridine, arsindole, isoarsinoline, isophosphoindole, isophosphinoline, phosphoindole, phosphinoline, selenophene, tellurophene and xanthene. In preferred embodiments, the heteroaryl group is a 5–20 membered heteroaryl, with 5–10 membered heteroaryl being particularly preferred.

"Substituted Heteroaryl:" refers to a heteroaryl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl where each R is independently —H, alkyl, alkenyl, alkynl, aryl, arylalkyl, heteroaryl or heteroarylalkyl as defined herein.

"Arylalkyl:" refers to a straight-chain alkyl, alkenyl or alkynyl group wherein one of the hydrogen atoms bonded to the terminal carbon is replaced with an aryl moiety. Typical arylalkyl groups include, but are not limited to, benzyl, naphthylmethyl, naphthobenzyl, benzylidene, benzylidyne, benzenobenzyl, napthalenobenzyl and the like. In preferred embodiments, the arylalkyl group is ($C_6$–$C_{26}$) arylalkyl, i.e., the alkyl, alkenyl or alkynyl moiety of the arylalkyl group is ($C_1$–$C_6$) and the aryl moiety is ($C_5$–$C_{20}$). In particularly preferred embodiments the arylalkyl group is ($C_6$–$C_{13}$), i.e., the alkyl, alkenyl or alkynyl moiety of the arylalkyl group is ($C_1$–$C_3$) and the aryl moiety is ($C_5$–$C_{10}$).

"Substituted Arylalkyl:" refers to an arylalkyl radical wherein one or more hydrogen atoms on the aryl moiety are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

"Heteroarylalkyl:" refers to a straight-chain alkyl, alkenyl or alkynyl group where one of the hydrogen atoms bonded to a terminal carbon atom is replaced with a heteroaryl moiety. In preferred embodiments, the alkheteroaryl group is a 6–26 membered heteroarylalkyl, i.e., the alkyl, alkenyl or alkynyl moiety of the heteroarylalkyl is ($C_1$–$C_6$) and the heteroaryl moiety is a 5–20-membered heteroaryl (other than imidazole). In particularly preferred embodiments, the heteroarylalkyl is a 6–13 membered heteroarylalkyl, i.e., the alkyl, alkenyl or alkynyl moiety is ($C_1$–$C_3$) and the heteroaryl moiety is a 5–10 membered heteroaryl.

"Substituted Heteroarylalkyl:" refers to an heteroarylalkyl radical wherein one or more hydrogens on the heteroaryl moiety are each independently replaced with another substituent. Typical substituents include, but are not limited to, —R, —OR, —SR, —NRR, —CN, —NO$_2$, —C(O)R, —C(O)OR, —C(O)NRR, —C(S)NRR, —C(NR)NRR, —NR—C(NR)—R, —NR—C(NR)—OR, —NR—C(NR)—SR, —NR—C(NR)—NRR, -halogen and -trihalomethyl, where each R is independently —H, alkyl, alkenyl, alkynyl, aryl, arylalkyl, heteroaryl or heteroarylalkyl, as defined herein.

5. BRIEF DESCRIPTION OF THE FIGURES

FIG. 1 provides a graph illustrating the recovery of neurological function in rats treated with normal saline (□) or 1 mg/kg Compound 2a (▨) at 30 min. following moderate fluid percussion injury. Bars (□ or ▨) represent the median value for all animals in that treatment group. Dots (●) represent values for individual animals. * indicates $p < 0.05$ with respect to saline-treated control; ** indicates $p < 0.01$ with respect to saline-treated controls.

FIG. 2 provides a graph illustrating the recovery of neurological function in rats treated with normal saline (□), 1 mg/kg Compound 1a (▨) or 1 mg/kg Compound 4a (▩) at 30 min. following moderate fluid percussion injury. Bars (□, ▨ or ▩) represent the median value for all animals in that treatment group. Dots (●) represent values for individual animals.

FIG. 3 provides a graph illustrating the beam walking performance of uninjured control mice (◇) and mice treated with normal saline (○) or 1.0 mg/kg Compound 2a (□) at 30 min. following controlled cortical injury (CCI). Results are expressed as daily mean±SEM number of right hindlimb footfaults (maximum 50) per treatment group. # indicates $p < 0.05$ with respect to injured controls (CCI+saline); ## indicates $p < 0.01$ with respect to injured controls (CCI+saline); *** indicates $p < 0.001$ with respect to uninjured controls (sham+saline).

FIG. 4 provides a graph illustrating the beam-walking performance of uninjured control mice (+) and mice treated with 0.1 mg/kg (□), 1.0 mg/kg (Δ) or 10.0 mg/kg (◇) Compound 2a at 60 minutes following controlled cortical injury. Results are expressed as daily mean±SEM number of right hindlimb footfaults (maximum 50) per treatment group.

FIG. 5 provides a graph illustrating the latency of finding a hidden platform in a place learning version of the Morris watermaze for uninjured control mice (▤) and mice treated with normal saline (□) or 1.0 mg/kg Compound 2a (▨) at 30 min. following controlled cortical injury (CCI). Results are expressed as daily means±SEM for each group over four trials. * indicates $p < 0.05$ with respect to uninjured controls (sham+saline);  indicates $p < 0.01$ with respect to uninjured controls (sham+saline); * indicates $p < 0.001$ with respect to uninjured controls (sham+saline); and # indicates $p < 0.01$ with respect to injured controls (CCI+saline).

FIGS. 6A and 6B provide graphs illustrating the latency of finding a hidden platform in a place learning version of the Morris watermaze for uninjured control mice (■) and mice treated with normal saline (▨) or 0.1 mg/kg (▩), 1.0 mg/kg (▦) or 10.0 mg/kg (▧) Compound 2a at 60 min. following controlled cortical injury. In FIG. 6A, the control group contained 6 animals and each treatment group contained 8 animals. In FIG. 6B, the control group contained 12 animals and each treatment group contained 8 animals.

FIG. 7 provides a graph illustrating the latency of finding a hidden platform in a working memory version of the Morris watermaze for uninjured control mice (sham+saline) and mice treated with normal saline (CCI+saline) or 1.0 mg/kg Compound 2a (CCI+Compound 2a) at 30 min. following controlled cortical injury (CCI). Filled bars (■) represent the first of two consecutive trials; unfilled bars (▨) represent the second of two consecutive trials. Results are expressed as daily means±SEM for each group over four trial pairs. * indicates $p < 0.05$ with respect to uninjured controls (sham+saline); # indicates $p < 0.05$ with respect to injured saline-treated controls (CCI+saline).

FIG. 8 provides a graph illustrating the mean number of footfalls in a beam walking task in mice treated with saline (○), 1 mg/kg Compound 10b (Δ) or 1 mg/kg Compound 11b (□) following controlled cortical impact (CCI) injury.

FIG. 9 provides a graph illustrating the recovery of neurological function in rats treated with normal saline (□), 1 mg/kg diiodo-YM-14673 (▨) or 1 mg/kg Compound 14c (▧) at 30 min. following moderate fluid percussion injury. Bars represent the median value for all animals in that treatment group; * indicates $p < 0.05$ with respect to saline-treated controls; and ** indicates $p < 0.01$ with respect to saline-treated controls.

FIG. 10 provides a graph illustrating the effect of saline vehicle and TRH analogues on core body temperature in lightly anesthetized rats. Open dots (□) represent normal saline; filled dots (●) represent 1 mg/kg YM-14673; (□) represents diiodo-YM-14673, and open triangles (Δ) represent 1 mg/kg Compound 14c.

FIG. 11 provides a graph illustrating the effect of saline vehicle and TRH analogues on latency to recover righting reflex in rats following light anesthesia. Rats were treated intravenously with either normal saline (□); YM-14673; diiodo-YM-14673; or Compound 14c (▨) at doses of 1 mg/kg and 10 mg/kg.

FIG. 12 provides a graph illustrating the mean arterial blood pressure (MAP) at various times following intravenous administration of normal saline (○), 1 mg/kg YM-14637 (●), 1 mg/kg diiodo-YM-14673 (□), or 1 mg/kg Compound 14c (Δ) to fully conscious and unrestrained rats.

FIG. 13 provides a graph illustrating performance at sham-operated and controlled cortical impact (CCI)-injured mice in a beam walking task measuring fine motor coordination. Results are expressed as daily mean+/−SEM number or light handlimb footfalls (maximum 50) per treatment group. # indicates p<0.05 with respect to uninjured controls (sham+saline); ## indicates p<0.01 with respect to uninjured controls (sham+saline); *** indicates p<0.001 with respect to uninjured controls (sham+saline).

6. DETAILED DESCRIPTION OF THE INVENTION

As discussed in the Background section, a major drawback of TRH as a compound to treat CNS trauma is its short plasma half-life (4–5 min.), which is thought to be due to rapid degradation of the peptide in vivo. Cleavage of the pyroglutamyl moiety of TRH by peptidases causes formation of the cyclic dipeptide metabolite cyclo(His-Pro). However, while cyclo(His-Pro) and other cyclic dipeptides are known to exist in nature, very few of these compounds have been tested for biological activity in mammals. Of those that have been tested, only a limited number exhibit any biological activity. In particular, none of the cyclic dipeptides are known to exhibit neuroprotective effects or to enhance working and learning memory following acute or chronic brain injury, or to treat neurological diseases such as brain or spinal cord trauma, stroke or neurodengerative disorders such as Alzheimer's disease (for a review of known cyclic dipeptides and their respective activities, see, Prasad, 1995, Peptides 16(1):151–164; see also, DD 246767, DD 153208 and GB 2127807).

Peptidase-resistant TRH analogues which exhibit significant CNS activity have been synthesized. However, to date most modifications have been limited to the pyroglutamyl and prolineamide portions of the TRH molecule. Among the most neuroprotective of these analogues is compound YM-14673, in which the pyroglutamyl moiety of TRH has been replaced with a 2-azetidinone moiety (Faden, 1989, supra). Few modifications have been made at the histidyl portion of the molecule, the most significant being substitutions at various positions of the imidazole ring with trifluoromethyl, nitro and/or halogen groups (see, U.S. Pat. No. 5,686,420). The most active of these various TRH analogues is the diiodo analogue of YM-14673. The structure of TRH analogue YM-14673 and its diiodo analogue (called 2-ARA-53a) are shown below:

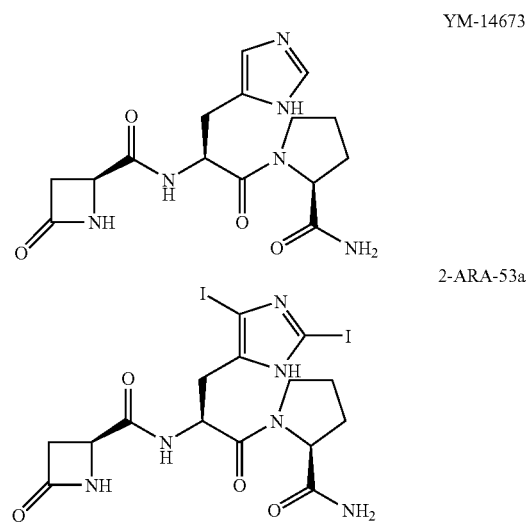

Quite surprisingly, it has now been discovered that certain cyclic dipeptide compounds (also known as bicyclic 2,5-dioxopiperazines; bicyclic 2,5-diketopiperazines; cyclo (dipeptides); or dipeptide anhydrides) exhibit strong central nervous system (CNS) activity. It has further been discovered that the imidazole moiety of 2-azetidinone TRH analogues such as YM-14673 and 2-ARA-53a is not required for CNS activity. As a consequence, it has been discovered that 2-azetidinone TRH analogues which contain significant modifications at the histidyl portion of the molecule exhibit strong central nervous system activity. It has further been discovered that cyclic dipeptide compounds containing a sulfanyl group can form disulfide-bridged dimers that exhibit strong CNS activity. Similarly, 2-azetidinone analogues containing a sulfanyl group can form disulfide-bridged dimers that exhibit strong CNS activity. Further, heterodimers wherein one monomer is a cyclic dipeptide compound of the present invention, and the other monomer is a 2-azetidinone TRH analogue of the present invention possess strong CNS activity.

Because of the strong CNS activity that was unexpectedly exhibited by the various classes of compounds described herein, all of these compounds can be used to enhance cognitive function, particularly working and learning memory function following acute or chronic brain or spinal cord injury. They may also be used to treat neurological disorders, particularly neurological disorders that are caused by trauma to the CNS, including brain trauma and spinal cord trauma, as well as stroke and neurodegenerative disorders such as Alzheimer's disease.

The compounds of the invention provide myriad advantages over TRH and its known analogues. For example, the compounds of the invention exhibit better neuroprotective effects than YM-14673 in direct comparison tests; show little in the way of systemic effects; and exhibit fewer analeptic and/or autonomic effects than YM-14673. Moreover, since the compounds of the invention are not susceptible to cleavage by proteases present in the body, they have a significantly longer in vivo half-life than TRH. As a consequence, the TRH analogues of the invention can be administered at lower dosages than TRH, and, unlike TRH which requires continuous infusion to be effective, they can be administered efficaciously in a single bolus injection, thereby providing consequential therapeutic benefits in clinical settings.

6.1 The Compounds The compounds that are useful as neuroprotectants (i.e. for treating CNS injuries or neurological diseases and/or enhancing memory function) according to the invention generally comprise three classes of compounds: bicyclic 2,5-diketopiperazines; 2-azetidinone TRH analogues; and various disulfide-bridged homo and heterodimers thereof. The bicyclic 2,5-diketopiperazines are generally compounds having the formula (Ia):

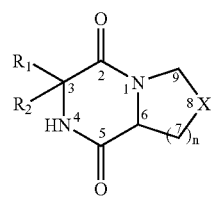

wherein:

n is an integer from 0 to 3;

X is selected from the group consisting of —S—, —O—, —NR— and —CH$_2$—;

R$_1$ and R$_2$ are each independently selected from the group consisting of —H, —OR, —SR, —NRR, NO$_2$, —CN, —C(O)OR, —C(O)NRR, —C(NR)NRR, halogen, trihalomethyl, (C$_1$–C$_6$) alkyl, substituted (C$_1$–C$_6$) alkyl, (C$_2$–C$_6$) alkenyl, substituted (C$_2$–C$_6$) alkenyl, (C$_2$–C$_6$) alkynyl, substituted (C$_2$–C$_6$) alkynyl, (C$_5$–C$_{20}$) aryl, substituted (C$_5$–C$_{20}$) aryl, 5–20 membered heteroaryl, substituted 5–20 membered heteroaryl, (C$_6$–C$_{26}$) arylalkyl, substituted (C$_6$–C$_{26}$) arylalkyl, 6–26 membered heteroarylalkyl and substituted 6–26 membered heteroarylalkyl, or R$_1$ and R$_2$ taken together are —CH$_2$—(CH$_2$)$_m$—CH$_2$—, where m is an integer from 0 to 6;

each alkyl, alkenyl, alkynyl, aryl, arylalkyl, heteroaryl or heteroarylalkyl substituent is independently selected from the group consisting of —R, —OR, —SR, —NRR, —CN, —NO$_2$, —C(O)OR, —C(O)NRR, —C(S)NRR, —C(NR)NRR, —NR—C(NR)—R, —NR—C(NR)—OR, —NR—C(NR)—SR, —NR—C(NR)—NRR, halogen and trihalomethyl; and each R is independently selected from the group consisting of —H, (C$_1$–C$_6$) alkyl, (C$_2$–C$_6$) alkenyl, (C$_2$–C$_6$) alkynyl, (C$_5$–C$_{20}$) aryl, (C$_6$–C$_{26}$) arylalkyl, 5–20 membered heteroaryl and 6–26 membered heteroarylalkyl.

In structure (Ia), the numbers inside the ring refer to the IUPAC numbering system for the parent 2,5-diketopiperazine ring. When n>1, the additional carbons inserted between the carbons at positions 7 and 8 are numbered 7A, 7B, etc., depending on the value of n.

As can be seen in structure (Ia), the parent bicyclic 2,5-diketopiperazine ring has two chiral centers: one at carbon 3 (when R$_1$ and R$_2$ are each different substituents) and one at carbon 6. In the compounds of the invention, the chirality at these two carbons may be the same or different, and may be either R or S. Thus, specifically contemplated by the present invention are compounds described by structural formulae (IIa), (IIIa), (IVa) and (Va), where R$_1$, R$_2$, X and n are as defined for structure (Ia), above:

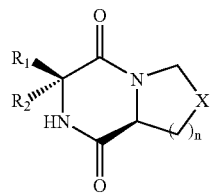

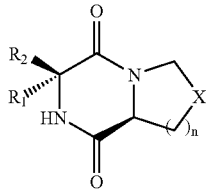

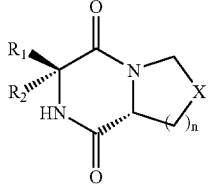

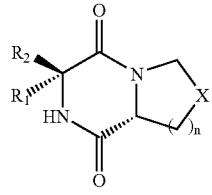

Preferably, the chirality at both of carbons 3 and 6 is S. Structural formulae (IIa) and (IIIa) are preferred.

Those of skill in the art will appreciate that substituents R$_1$ and R$_2$ may also contain chiral centers. In addition, the R$_1$ and R$_2$ substituents, as well as the parent bicyclic 2,5-diketopiperazine ring, may further exhibit the phenomena of tautomerism, conformational isomerism, or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The 2-azetidinone TRH analogues of the invention are a generally a class of TRH compounds in which the pyroglutamyl portion of the molecule has been replaced with a 2-azetidinone moiety and in which the histidyl portion of the molecule has also been modified. Significantly, the TRH analogues of the invention do not contain an imidazole or substituted imidazole ring at the histidyl portion of the molecule. Additionally, the prolinamide may contain heteroatoms such as O, N or S, and/or may contain from 4 to 7 ring atoms. Thus, the 2-azetidinone TRH analogues of the invention are compounds having the following structural formula (Ib):

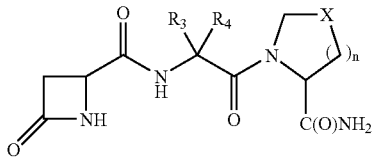

wherein:
- n is as previously defined for structure (Ia);
- X is as previously defined for structure (Ia);
- $R_3$ and $R_4$ are each independently selected from the group consisting of —H, —CN, —C(O)OR', —C(O)NR'R', —C(NR')NR'R', trihalomethyl, ($C_1$–$C_6$) alkyl, substituted ($C_1$–$C_6$) alkyl, ($C_2$–$C_6$) alkenyl, substituted ($C_2$–$C_6$) alkenyl, ($C_2$–$C_6$) alkynyl, substituted ($C_2$–$C_6$) alkynyl, ($C_5$–$C_{20}$) aryl, substituted ($C_5$–$C_{20}$) aryl, 5–20 membered heteroaryl, substituted 5–20 membered heteroaryl, ($C_6$–$C_{26}$) arylalkyl, substituted ($C_6$–$C_{26}$) arylalkyl, 6–26 membered heteroarylalkyl and substituted 6–26 membered heteroarylalkyl,
- or $R_3$ and $R_4$ taken together are —$CH_2$—$(CH_2)_p$—$CH_2$—, where p is an integer from 0 to 6;
- each alkyl, alkenyl, alkynyl, aryl, arylalkyl, heteroaryl or heteroarylalkyl substituent is independently selected from the group consisting of —R', —OR', —SR', —NR'R', —CN, —$NO_2$, —C(O)OR', —C(O)NR'R', —C(S)NR'R', —C(NR')NR'R', —NR'—C(NR')—R', —NR'—C(NR')—OR', —NR'—C(NR')—SR', —NR'—C(NR')—NR'R', halogen and trihalomethyl; and
- each R' is independently selected from the group consisting of —H, ($C_1$–$C_6$) alkyl, ($C_2$–$C_6$) alkenyl, ($C_2$–$C_6$) alkynyl, ($C_5$–$C_{20}$) aryl, ($C_6$–$C_{26}$) arylalkyl, 5–20 membered heteroaryl and 6–26 membered heteroarylalkyl, with the provisos that:
(i) when n is 1; X is —$CH_2$—; and one of $R_3$ or $R_4$ is —H; then the other of $R_3$ or $R_4$ is not:

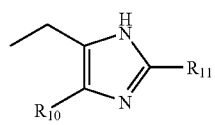

where $R_{10}$ is —$CF_3$, —$NO_2$ or a halogen and $R_{11}$ is —H, or $R_{10}$ is —H and $R_{11}$ is —$CF_3$, or $R_{10}$ and $R_{11}$ are each independently a halogen; and/or (ii) when n is 1, 2 or 3; X is —$CH_2$—; and one of $R_3$ or $R_4$ is —H, ($C_1$–$C_6$) alkyl, ($C_2$–$C_6$) alkenyl or ($C_2$–$C_6$) alkynyl; then the other of $R_3$ or $R_4$ is not —$(CH_2)_a$—R", where a is 0, 1, 2 or 3 and R" is selected from the group consisting of imidazolyl, imidazol-5-yl, imidazolyl independently substituted with one or more —$CF_3$, trihalomethyl, —$NO_2$ or halogen groups, imidazol-5-yl independently substituted with one or more —$CF_3$, trihalomethyl, —$NO_2$ or halogen groups, 2,4-dihalo-[1H]-imidazol-5-yl and 2,4-diiodo-[1H]-imidazol-5-yl.

As can be seen in structure (Ib), the parent molecule has three chiral centers: one at carbon 4 of the azetidinone moiety; one at the "backbone" α-carbon substituted with $R_3$ and $R_4$ (when $R_3$ and $R_4$ are different); and one at carbon 2 of the prolineamide-like moiety. In the TRH analogues of the invention, the chirality at these three carbons may be the same or different, and may be either R or S. Thus, specifically contemplated by the present invention are compounds according to structural formulae (IIb), (IIIb), (IVb), (Vb), (VIb), (VIIb), (VIIIb) and (IXb) where $R_3$, $R_4$, X and n are as previously defined for structure (Ib):

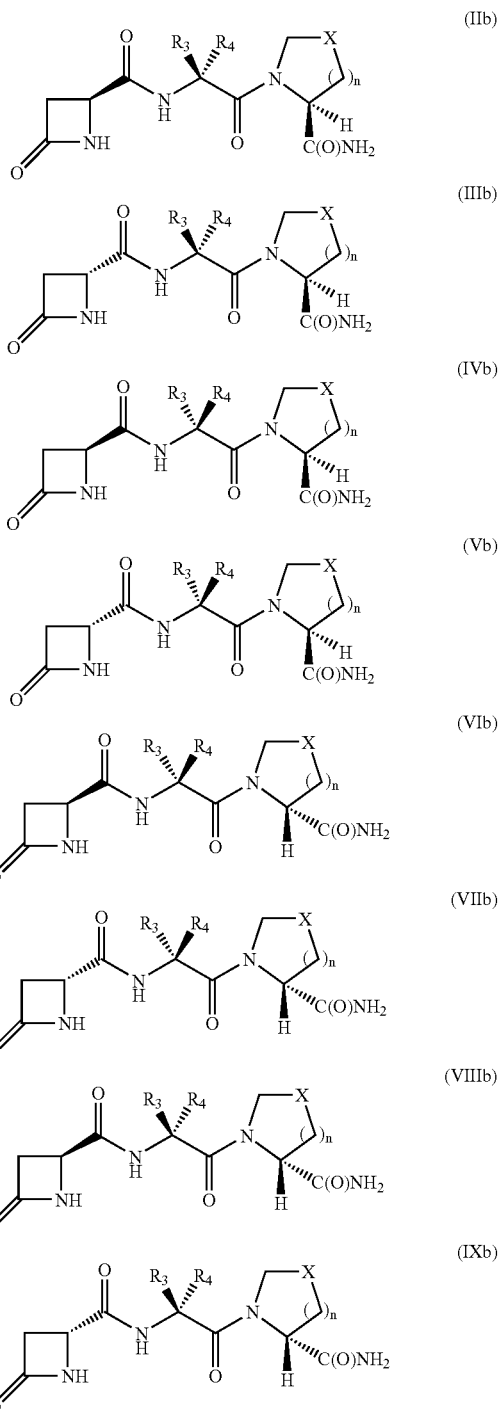

In all of the various embodiments of TRH analogues described herein, those according to structures (IIb) and (IVb) are preferred.

Those of skill in the art will appreciate that substituents $R_3$ and $R_4$ may also contain chiral centers. In addition, the $R_3$ and $R_4$ substituents, as well as the parent molecule, may further exhibit the phenomena of tautomerism, conformational isomerism, or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

Those of skill in the art will recognize that compounds of structural formulae (Ia)–(Va) and (Ib)–(IXb) in which either one or both $R_1$ and $R_2$ substituents and/or either one or both $R_3$ and $R_4$ substituents, respectively, contain a sulfanyl (—SH) group can form disulfide-bridged dimers. Such dimers may be heterodimers in which one monomer is a diketopiperazine compound selected from structural formulae (Ia)–(Va) and the other monomer is a 2-azetidinone TRH analogue selected from structural formulae (Ib)–(IXb). Alternatively, the dimer could be a homodimer in which both monomers are diketopiperazine compounds independently selected from formulae (Ia)–(Va) or TRH analogues independently selected from formulae (Ib)–(IXb). When such disulfide-bridged dimers are administered in vivo, they may become reduced to the monomeric form. Conversely, when sulfanyl-containing monomers are administered in vivo, they may become oxidized to the disulfide-bridged dimeric form. As both monomeric and dimeric forms have considerable activity, both monomeric and dimeric forms of these compounds are within the scope of the invention.

The dimers of the current invention can be represented by structural formula (Ic):

A—$(CH_2)_r$—S—S—$(CH_2)_r$—B     (Ic)

wherein:

—S—S— represents a disulfide bridge;

each r is independently an integer from 1 to 6; and

A and B are each independently selected from the group consisting of:

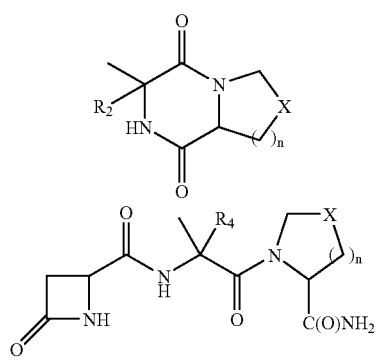

wherein:

each n, which may be the same or different, is as previously defined for structure (Ia);

each X, which may be the same or different, is as previously defined for structure (Ia);

each $R_2$, which may be the same or different, is as previously defined for structure (Ia); and each $R_4$, which may be the same or different, is as previously defined for structure (Ib).

Each monomer unit composing the dimer of formula (Ic) may have the same or different stereochemistry and may have the specific stereochemistry of any one of structures (Ia)–(Va) and (Ib)–(IXb). For example, one monomer may have the stereochemistry depicted in structure (IIa), the other the stereochemistry depicted in (IIb), and so forth.

One set of preferred dimers according to structure (Ic) includes compounds selected from the group consisting of:

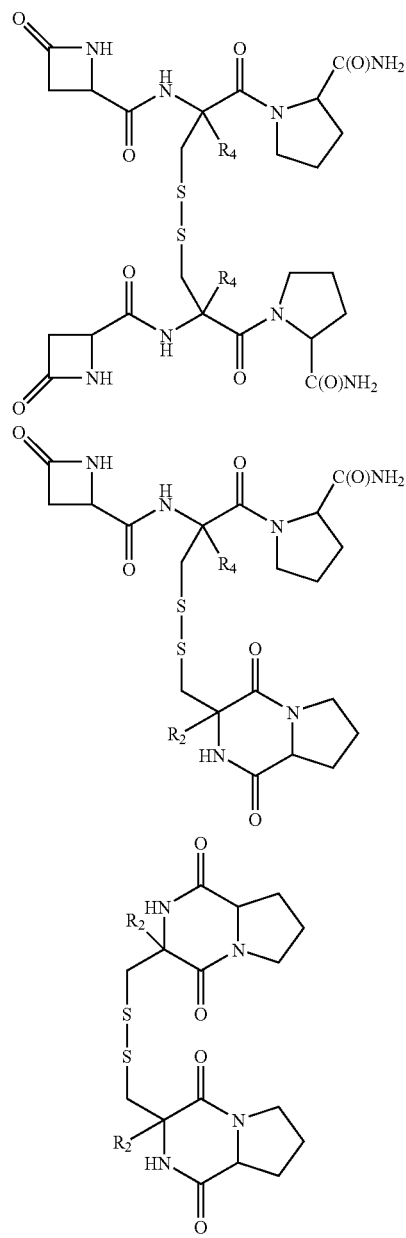

wherein:

each $R_2$, which may be the same or different, is as previously defined structure (Ia); and each $R_4$, which may be the same or different, is as previously defined for structure (Ib).

Particularly preferred dimers according to structure (Ic) are Compounds 14c, 15c and 16c:

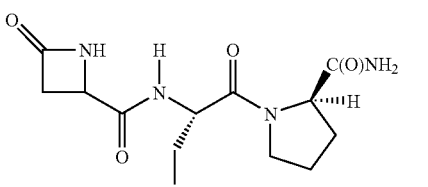
(14c)

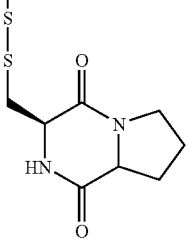
(15c)

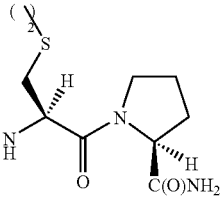
(16c)

The disulfide-bridged dimers of structure (Ic) do not show much affinity for TRH receptors per se. Thus, their mechanism of action is unlikely to involve direct interaction with these receptors. While not intending to be bound by any particular theory, it is believed that the compounds of structural formula (Ic), which contain a chemically reactive disulfide bridge, are converted in vivo to the sulfanyl-containing monomeric forms. By analogy to the mechanism of action of glutathione (Matsugo, 1995, Current Medicinal Chemistry 2:763–790), it is believed that the neuroprotective properties of compounds according to structure (Ic) may be associated with their free-radical scavenging properties.

Free-radical mediated oxidation of cellular macromolecules (such as lipids, proteins, nucleic acids, etc.) has been implicated in a number of disease states, including stroke and head trauma (Kontos, 1989, Chem-Biol. Int. 72:229–255). Reactive oxygen intermediates which can induce free-radical mediated oxidation include superoxide radical anion, hydrogen peroxide and the very aggressive hydroxyl radical. These radicals, acting mainly through initiation of chain reactions, can cause extensive damage to unsaturated lipids found in neural membranes, resulting in neuronal cell death and consequent neurological impairment.

The free-radical nitric oxide has also been implicated in disease pathways. Under normal conditions of brain activity, nitric oxide produced by the neuronal enzyme nitric oxide synthase (NOS) is believed to play a role as a neurotransmitter. However, since the inducible form of NOS plays a role in host defense mechanisms, it is also likely that excess production of the free-radical nitric oxide can destroy functional tissue in cases of chronic inflammation (Moncada et al., 1991, Pharmacol. Rev. 43:12231–12234). As a consequence, considerable attention has been given to the discovery of inhibitors of both the constitutive (brain and vascular endothelium) and inducible (macrophages) forms of NOS. The majority of these structures are analogues of L-arginine (Moore et al., 1994, J. Med. Chem. 37:3886–3888).

Due in part to the surmised mechanism of action of dimers according to structural formula (Ic) and the surmised role of certain free-radicals and enzymes in disease pathways, an important aspect of the invention is compounds according to structural formula (Ia), (Ib) and (Ic) in which at least one of $R_1$, $R_2$, $R_3$ or $R_4$ is a moiety that has free-radical scavenging properties, i.e., at least one of $R_1$, $R_2$, $R_3$ or $R_4$ is a moiety that is likely to disrupt radical damage-inducing cascades, including those cascades involving both reactive oxygen intermediates and nitric oxide.

A particularly important class of compounds according to the invention which possess radical-scavenging properties includes those compounds according to structural formulae (Ia)–(Va) and (Ib)–(IXb) in which at least one of $R_1$, $R_2$, $R_3$ or $R_4$ is a moiety which acts as an oxygen-radical trap or an inhibitor of NOS. Molecules which act as oxygen radical traps (antioxidants) or NOS inhibitors are well-known in the art. For example, glutathione, thioredoxin and vitamins E and C act as oxygen-radical scavenging antioxidants (Matsugo et al., 1995, supra). Compounds which act as NOS inhibitors include, for example, the L-arginine analogues described in Moore et al., 1994, supra. Other known or later-discovered radical-scavenging compounds or NOS inhibitors are also useful as $R_1$, $R_2$, $R_3$ or $R_4$ substituents. It is well within the capabilities of those having skill in the art to identify those portions of known or later discovered antioxidants and NOS inhibitors responsible for effecting activity that can be used as $R_1$, $R_2$, $R_3$ or $R_4$ substituents to make TRH analogues and/or 2-5,-diketo-piperazines within the scope of the invention. Such moieties may be covalently attached directly to the backbone structures depicted in structural formulae (Ia)–(Va) and (Ib)–(IXb), or may alternatively be covalently attached by way of a "linker", such as a ($C_1$–$C_6$) alkyl chain.

The compounds of the invention can be further defined by reference to additional preferred embodiments, which are described below.

In one set of preferred embodiments, the compounds are those of structural formulae (Ia)–(Va), wherein:

n is an integer from 0 to 3;

X is selected from the group consisting of —S—, —O—, —NR— and —CH$_2$—;

R$_1$ and R$_2$ are each independently selected from the group consisting of —H, —OR, —SR, —NRR, —NO$_2$, —CN, —C(O)OR, —C(O)NRR, —C(NR)NRR, trihalomethyl, halogen, (C$_1$–C$_6$) alkyl, substituted (C$_1$–C$_6$) alkyl, (C$_2$–C$_6$) alkenyl, substituted (C$_2$–C$_6$) alkenyl, (C$_2$–C$_6$) alkynyl, substituted (C$_2$–C$_6$) alkynyl, (C$_5$–C$_{20}$) aryl, substituted (C$_5$–C$_{20}$) aryl, 5–20 membered heteroaryl, substituted 5–20 membered heteroaryl, (C$_6$–C$_{26}$) alkaryl, substituted (C$_6$–C$_{26}$) alkaryl, 6–26 membered alk-heteroaryl and substituted 6–26 membered alk-heteroaryl, or R$_1$ and R$_2$ taken together are —CH$_2$—(CH$_2$)$_k$—CH$_2$—, where k is an integer from 0 to 6;

each alkyl, alkenyl, alkynyl, aryl, alkaryl, heteroaryl or alk-heteroaryl substituent is independently selected from the group consisting of —OR, —SR, —NRR, —CN, —NO$_2$, —C(O)OR, —C(O)NRR, —C(S)NRR, —C(NR)NRR, halogen and trihalomethyl; and each R is independently selected from the group consisting of —H, (C$_1$–C$_6$) alkyl, (C$_2$–C$_6$) alkenyl, (C$_2$–C$_6$) alkynyl, (C$_5$–C$_{20}$) aryl, 5–20 membered heteroaryl, (C$_6$–C$_{26}$) alkaryl and 6–26 membered alk-heteroaryl, with the provisos that (i) when n is 1 or 2 and X is —CH$_2$—, R$_1$ and R$_2$ taken together are other than —CH$_2$—CH$_2$—CH$_2$—CH$_2$—; and/or (ii) when n is 1 or 2 and X is —CH$_2$—, R$_1$ and R$_2$ taken together are other than —CH$_2$—(CH$_2$)$_z$—CH$_2$—, where z is an integer from 1 to 3; and/or (iii) when n is 1, X is —CH$_2$— and one of R$_1$ or R$_2$ is H, the other of R$_1$ or R$_2$ is other than (C$_1$–C$_6$) alkyl, (C$_1$–C$_6$) alkyl mono-substituted with —NH$_2$ (preferably —(CH$_2$)$_4$—NH$_2$), (C$_1$–C$_6$) alkyl mono-substituted with —C(O)OH (preferably —CH$_2$—C(O)OH), (C$_1$–C$_6$) alkyl mono-substituted with —NH—C(NH)NH$_2$ (preferably —(CH$_2$)$_3$—NH—C(NH)NH$_2$), (C$_5$–C$_{20}$) aryl (preferably phenyl), 5–20 membered alk-heteroaryl (preferably where the alkyl moiety is —CH$_2$— and the heteroaryl moiety is imidazol-2-yl or indol-3-yl), (C$_6$–C$_{26}$) alkaryl (preferably benzyl) or 6–26 membered alkaryl mono-substituted with —OH or (C$_1$–C$_6$) alkoxy (preferably p-hydroxybenzyl); and/or (iv) the compound is not cyclo(Pro-Ala), cyclo(Pro-Val), cyclo(Pro-Leu), cyclo(Pro-homoLeu), cyclo(Pro-Ile), cyclo(Pro-His), cyclo(Pro-Phe), cyclo(Pro-D-Phe), cyclo(D-Pro-Phe), cyclo(Pro-Tyr), cyclo(Pro-Trp), cyclo(Pro-Lys), cyclo(Pro-Arg) or cyclo(Pro-Asp), where all amino acids are in the L-configuration unless otherwise specified.

In another set of preferred embodiments, the compounds are those of structural formulae (Ia)–(Va), more preferably structure (IIIa), wherein X is —CH$_2$— and/or n is 1, and R$_1$ and R$_2$ are as previously defined for structure (Ia).

In another set of preferred embodiments, the compounds are those of structural formulae (Ia)–(Va), more preferably structure (IIIa), where R$_1$ is H and X, n and R$_2$ are as previously defined for structure (Ia).

In another set of preferred embodiments, the compounds are those of structural formulae (Ia)–(Va), wherein:

X is —S—, —O—, —NH— or —CH$_2$—;

n is 1, 2 or 3;

R$_1$ is —H;

R$_2$ is —CH$_2$—R$_5$, —CH$_2$—CH$_2$—R$_5$ or —CH$_2$—CH$_2$—CH$_2$—R$_5$;

R$_5$ is phenyl, imidazolyl (preferably other than imidazol-2-yl), indolyl (preferably other than indol-3-yl), —SR$_6$, —OR$_6$ or —NHR$_6$; and R$_6$ is —H, (C$_1$–C$_6$) alkyl (preferably t-butyl), (C$_2$–C$_6$) alkenyl, (C$_2$–C$_6$) alkynyl, —C(NH)NH$_2$ or —C(S)NH$_2$.

Particularly preferred compounds according to this aspect of the invention are those of structural formulae (IIa) and (IIIa) wherein X is —CH$_2$— and R$_5$ is —SR$_6$.

In another set of preferred embodiments, the compounds are those of structural formulae (Ia)–(Va), wherein:

n is an integer from 1 to 3;

X is —S—, —O—, —NH— or —CH$_2$—;

R$_1$ is —H;

R$_2$ is —H, (C$_1$–C$_6$) alkyl, (C$_2$–C$_6$) alkenyl, (C$_2$–C$_6$) alkynyl or —(CH$_2$)$_g$—CH$_2$—R$_7$;

g is an integer from 0 to 5;

R$_7$ is —OR$_8$, —SR$_8$, —NR$_8$R$_8$, —CH(OR$_8$)—CH$_3$, —C(O)R$_8$, —C(O)OR$_8$, —C(O)NR$_8$R$_8$, —S—C(NH)NH$_2$, —NH—C(NH)NH$_2$, —NH—C(S)NH$_2$, phenyl, hydroxyphenyl, imidazolyl, indolyl; and R$_8$ is —H, (C$_1$–C$_6$) alkyl, (C$_2$–C$_6$) alkenyl, (C$_2$–C$_6$) alkynyl. Particularly preferred compounds according to this aspect of the invention are those of structural formulae (IIa) or (IIIa) wherein X is —CH$_2$— and/or n is 1.

In another set of preferred embodiments, the compounds of the invention are those of structural formulae (Ia)–(Va), wherein:

X is —S—, —O—, —NH— or —CH$_2$—;

n is an integer from 1 to 3; and

R$_1$ and R$_2$ taken together are —CH$_2$—(CH$_2$)$_b$—CH$_2$—, where b is an integer from 0 to 6. Particularly preferred compounds according to this aspect of the invention are those of structural formulae (IIa) or (IIIa) wherein X is —CH$_2$— and/or n is 1.

In another set of preferred embodiments, the compounds of the invention are selected from Compounds (1a)–(10a), below:

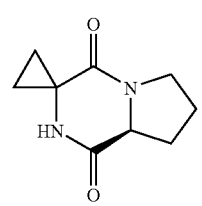

(1a)

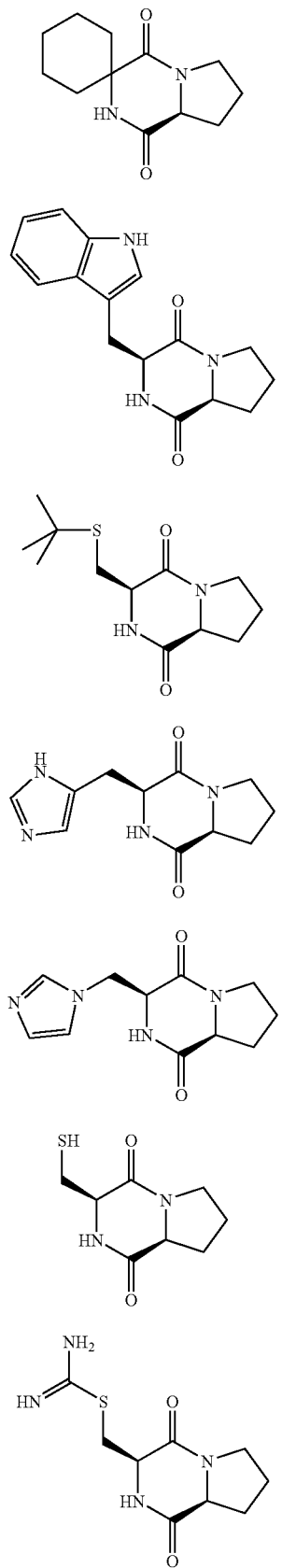

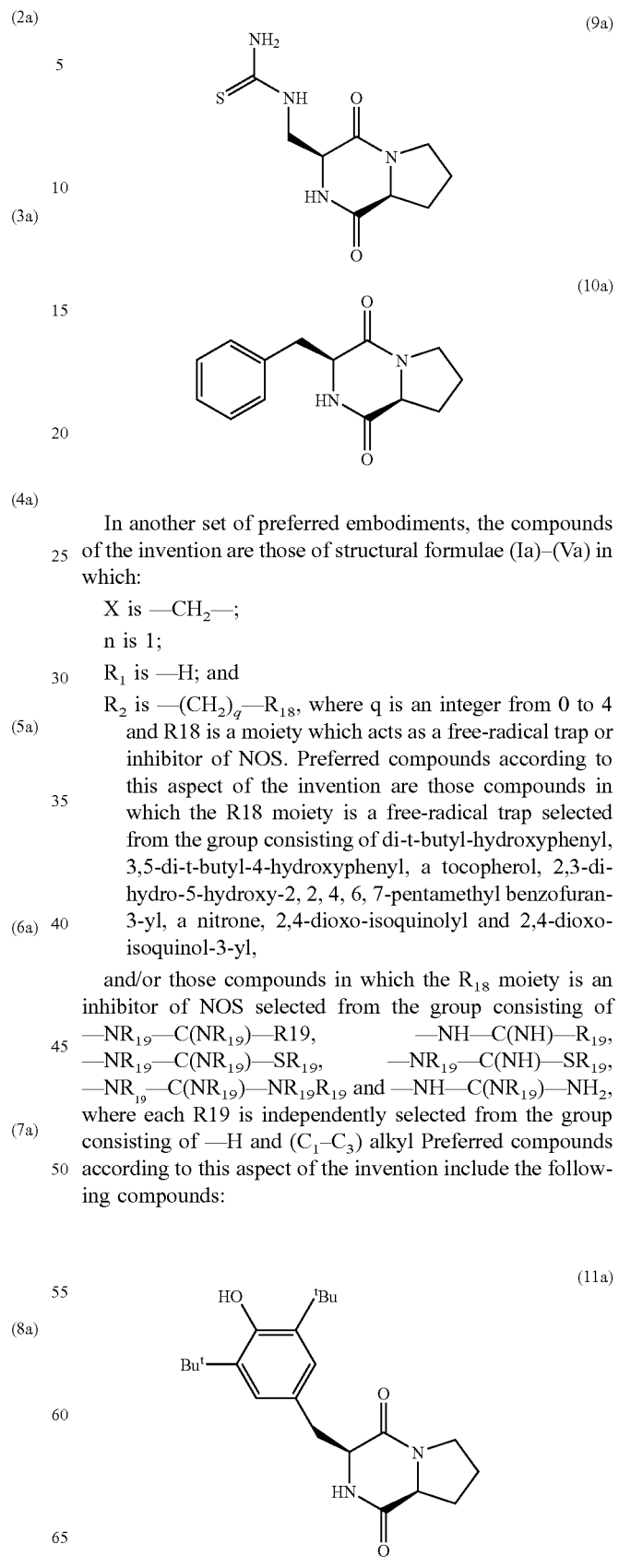

In another set of preferred embodiments, the compounds of the invention are those of structural formulae (Ia)–(Va) in which:

X is —CH$_2$—;

n is 1;

R$_1$ is —H; and

R$_2$ is —(CH$_2$)$_q$—R$_{18}$, where q is an integer from 0 to 4 and R18 is a moiety which acts as a free-radical trap or inhibitor of NOS. Preferred compounds according to this aspect of the invention are those compounds in which the R18 moiety is a free-radical trap selected from the group consisting of di-t-butyl-hydroxyphenyl, 3,5-di-t-butyl-4-hydroxyphenyl, a tocopherol, 2,3-dihydro-5-hydroxy-2, 2, 4, 6, 7-pentamethyl benzofuran-3-yl, a nitrone, 2,4-dioxo-isoquinolyl and 2,4-dioxo-isoquinol-3-yl, and/or those compounds in which the R$_{18}$ moiety is an inhibitor of NOS selected from the group consisting of —NR$_{19}$—C(NR$_{19}$)—R19, —NH—C(NH)—R$_{19}$, —NR$_{19}$—C(NR$_{19}$)—SR$_{19}$, —NR$_{19}$—C(NH)—SR$_{19}$, —NR$_{19}$—C(NR$_{19}$)—NR$_{19}$R$_{19}$ and —NH—C(NR$_{19}$)—NH$_2$, where each R19 is independently selected from the group consisting of —H and (C$_1$–C$_3$) alkyl Preferred compounds according to this aspect of the invention include the following compounds:

(12a)
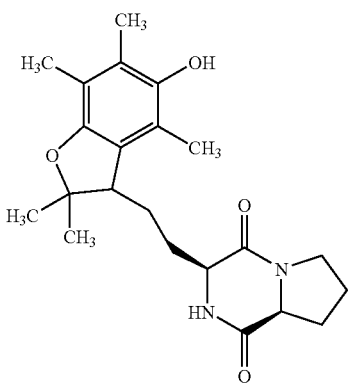

(13a)
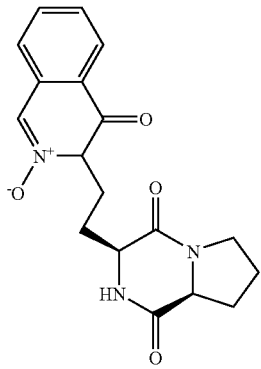

(14a)
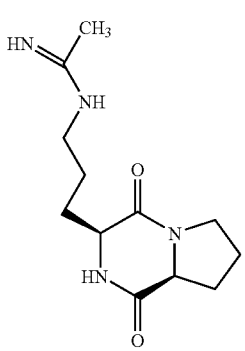

(15a)
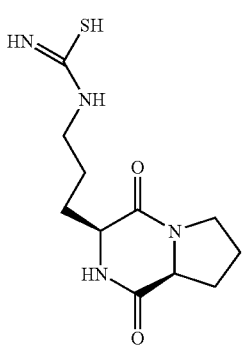

(16a)
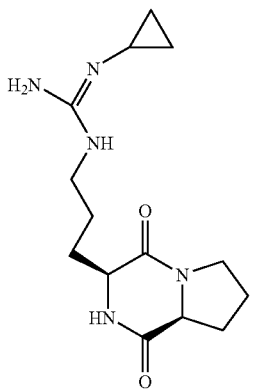

In another set of preferred embodiments, compounds of the invention are selected from compounds of formulae (Ib)–(IXb) in which n is 1 and X is —CH$_2$—.

In another set of preferred embodiments, compounds of the invention are according to structural formulae (Ib)–(IXb) in which the heteroaryl is not imidazolyl and the substituted heteroaryl is not substituted imidazolyl.

In another set of preferred embodiments, the TRH analogues are compounds according to structural formulae (Ib)–(IXb) in which R$_3$ and R$_4$, taken together, are —CH$_2$—(CH$_2$)$_p$—CH$_2$—, where p is an integer from 0 to 6.

In another set of preferred embodiments, the TRH analogues are compounds according to structural formulae (Ib)–(IXb) in which one of R$_3$ or R$_4$ is —H and the other is selected from the group consisting of —(CH$_2$)$_c$OR', —(CH$_2$)$_c$SR' and —(CH$_2$)$_c$R$_{12}$, where c is an integer from 1 to 3 (preferably 1); R' is as previously defined for structure (Ib) and R$_{12}$ is (C$_5$–C$_{20}$) aryl, substituted (C$_5$–C$_{20}$) aryl, 5–20 membered heteroaryl, substituted 5–20 membered heteroaryl, (C$_6$–C$_{26}$) arylalkyl, substituted (C$_6$–C$_{26}$) arylalkyl, 6–26 membered heteroarylalkyl and substituted 6–26 membered heteroarylalkyl, with the proviso that when n is 1; X is —CH$_2$—; and one of R$_3$ or R$_4$ is —H, (C$_1$–C$_6$) alkyl, (C$_2$–C$_6$) alkenyl or (C$_2$–C$_6$) alkynyl; then the other of R$_3$ or R$_4$ is not —(CH$_2$)$_h$—R$_{13}$, where h is 0, 1, 2 or 3 and R$_{13}$ is selected from the group consisting of imidazolyl, imidazol-5-yl, imidazolyl independently substituted with one or more —CF$_3$, trihalomethyl, —NO$_2$ or halogen groups, imidazol-5-yl independently substituted with one or more —CF$_3$, trihalomethyl, —NO$_2$ or halogen groups, 2,4-dihalo-[1H]-imidazol-5-yl and 2,4-diiodo-[1H]-imidazol-5-yl. Preferred amongst compounds according to this aspect of the invention are those compounds in which R' is —H or (C$_1$–C$_4$) alkyl (preferably methyl or t-butyl) and R$_{12}$ is pyrazolyl (preferably pyrazol-1-yl) or indolyl (preferably indol-3-yl).

In another set of preferred embodiments, the TRH analogues are compounds according to structural formulae (Ib)–(IXb) in which R$_3$ and R$_4$ are each independently selected from the group consisting of $(C_1-C_6)$ alkyl, $(C_2-C_6)$ alkenyl and $(C_2-C_6)$ alkynyl. Particularly preferred compounds according to this aspect of the invention are those in which $R_3$ and $R_4$ are each methyl.

In another set of preferred embodiments, the TRH analogues are compounds according to structural formulae (Ib)–(IXb) in which:

X is —CH$_2$—;

n is 1;

$R_3$ is —H; and $R_4$ is —(CH$_2$)$_d$—R$_{14}$, where d is an integer from 0 to 4 and $R_{14}$ is a moiety which acts as a free-radical trap or inhibitor of NOS. Preferred compounds according to this aspect of the invention are those compounds in which the $R_{14}$ moiety is a free-radical trap selected from the group consisting of di-t-butyl-hydroxyphenyl, 3,5-di-t-butyl-4-hydroxyphenyl, a tocopherol 2,3-dihydro-5-hydroxy-2,2,4,6,7-pentamethyl benzofuran-3-yl, a nitrone, 2,4-dioxo-isoquinolyl and 2,4-dioxo-isoquinol-3-yl, and/or those compounds in which the $R_{14}$ moiety is an inhibitor of NOS selected from the group consisting of —NR$_{15}$—C(NR$_{15}$)—R$_{15}$, —NH—C(NH)—R$_{15}$, —NR$_{15}$—C(NR$_{15}$)—SR$_{15}$, —NR$_{15}$—C(NH)—SR$_{15}$, —NR$_{15}$—C(NR$_{15}$)—NR$_{15}$R$_{15}$ and —NH—C(NR$_{15}$)—NH$_2$, where each $R_{15}$ is independently selected from the group consisting of —H and $(C_1-C_3)$ alkyl. Preferred compounds according to this aspect of the invention include the following compounds:

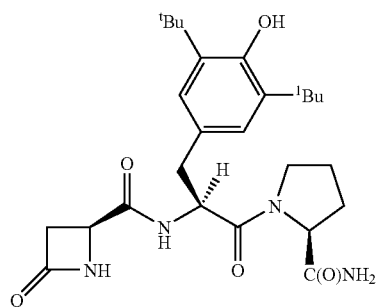
(1b)

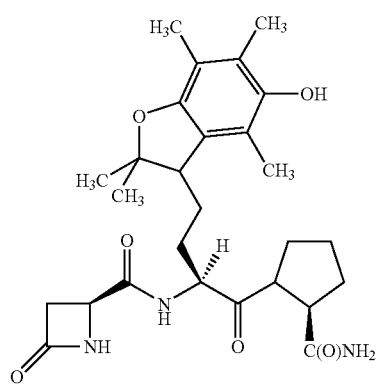
(2b)

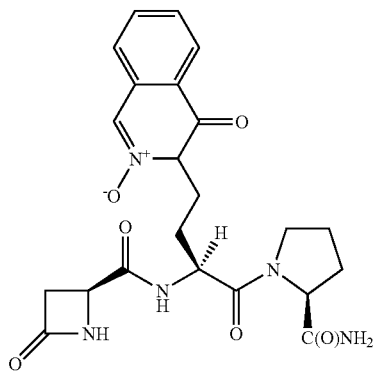
(3b)

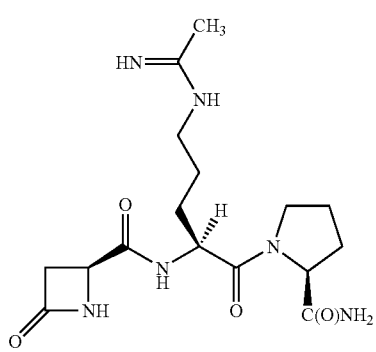
(4b)

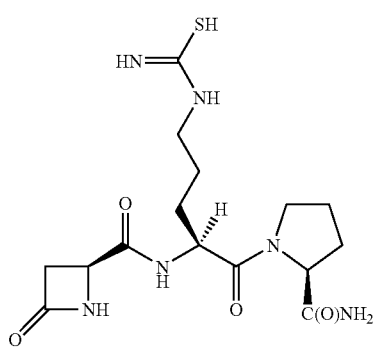
(5b)

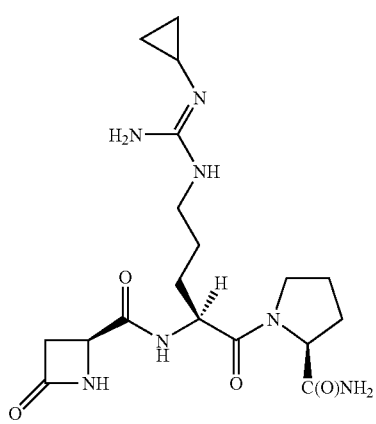
(6b)

In another set of preferred embodiments, the TRH analogues of the invention are compounds according to structural formulae (Ib)–(IXb) in which X is —CH$_2$—;

n is 1;

R$_3$ is —H; and

R$_4$ is selected from the group consisting of —(CH$_2$)$_e$—OR$_{16}$, —(CH$_2$)$_e$—SR$_{16}$, and —(CH$_2$)$_e$—R$_{17}$, where e is an integer from 1 to 3 (preferably 1), R$_{16}$ is —H or (C$_1$–C$_4$) alkyl (especially —H or t-butyl) and R$_{17}$ is (C$_5$–C$_{10}$) heteroaryl, pyrazolyl (especially pyrazol-1-yl) or indolyl (especially indol-3-yl), with the proviso that the heteroaryl is not imidazolyl or imidazol-5-yl.

Preferred compounds according to this aspect of the invention include the following:

(7b)

(8b)

(12b)

(13b)

In still another set of preferred embodiments, the TRH analogues of the invention are compounds according to structural formulae (Ib)–(IXb) in which:

X is —CH$_2$—;

n is 1; and

R$_3$ and R$_4$ are each independently selected from the group consisting of (C$_1$–C$_6$) alkyl, (C$_2$–C$_6$) alkenyl and (C$_2$–C$_6$) alkynyl. A particularly preferred compound according to this aspect of the invention is as follows:

(9b)

In yet another set preferred embodiments, the TRH analogues of the invention are compounds according to structural formulae (Ib)–(IXb) in which:

X is —CH$_2$—;

n is 1; and

R$_3$ and R$_4$ taken together are —CH$_2$— (CH$_2$)$_w$—CH$_2$ where w is an integer from 0 to 6. Particularly preferred compounds according to this aspect of the invention are as follows:

(10b)

(11b)

In still another set of preferred embodiments, the TRH analogues of the invention are hetero- or homo-dimers according to structural formula (Ic) in which each X is —CH$_2$— and each n is 1.

One preferred embodiment of the invention is a heterodimer as follows:

(14c)

In another set of preferred embodiments, the TRH analogues of the invention are hetero or homo dimers according to structural formula (Ic) in which:

each X is —CH$_2$—;

each n is 1;

each R$_2$ and R$_4$ is independently selected from the group consisting of —H, (C$_1$–C$_6$) alkyl, (C$_2$–C$_6$) alkenyl and (C$_2$–C$_6$) alkynyl; and each r is independently an integer from 1 to 6. A particularly preferred homodimer according to this aspect of the invention is as follows:

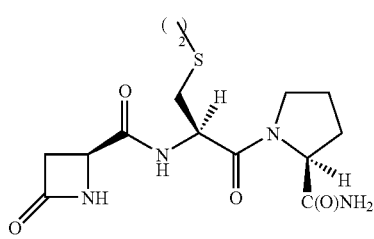

(15c)

A final preferred embodiment is a compound having structural formula:

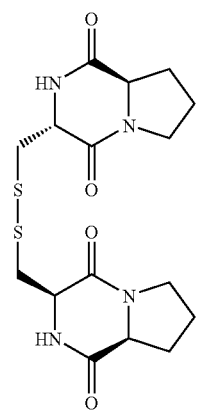

(16c)

The compounds of the invention may be in the form of free acids, free bases or pharmaceutically effective salts thereof. Such salts can be readily prepared by treating a compound with an appropriate acid. Such acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propanedioic acid, butanedioic acid, etc. Conversely, the salt can be converted into the free base form by treatment with alkali.

In addition to the above-described compounds and their pharmaceutically acceptable salts, the invention may employ, where applicable, solvated as well as unsolvated forms of the compounds (e.g. hydrated forms).

The compounds of the invention may be prepared by any processes known to be applicable to the preparation of chemical compounds. Suitable processes are well known in the art. Preferred processes are illustrated by the representative examples. Necessary starting materials may be obtained commercially or by standard procedures of organic chemistry.

By way of example, the cyclicdipeptides of the invention can be conveniently prepared by condensing an appropriate α-amino acid with an appropriate α-imino acid as illustrated in scheme (I), below:

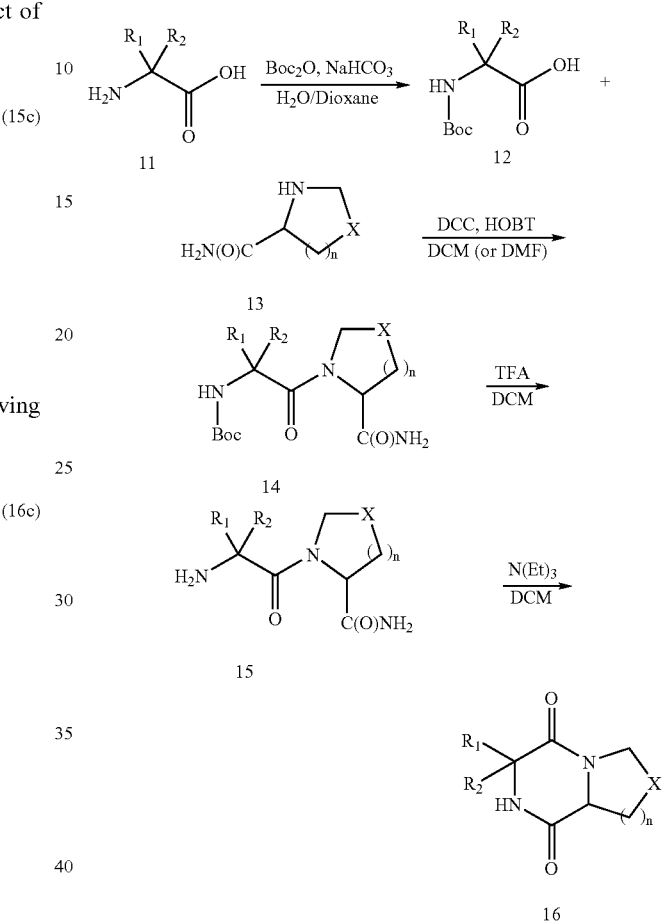

In Scheme (I), R$_1$, R$_2$, X and n are as defined for structural formula (I), supra. According to Scheme (I), an appropriate α-amino acid 11 is protected as the corresponding N-tert-butyl carbamate 12 using di-tert-dicarbonate (Boc$_2$O) and sodium bicarbonate in dioxane/water as solvent according to well-known methods (see, e.g., Williams et al., Chemical Approaches to the Synthesis of Peptides and Proteins, 1997, CRC Press, Boca Raton, Fla.; Atherton & Sheppard, Solid Phase Peptide Synthesis: A Practical Approach, 1989, IRL Press, Oxford, England, as well as the references cited therein). N-protected dipeptide 14 is prepared by condensing the N-tert butylcarbamate 12 with α-imino amide 13 using 1,3-dicyclohexylarbodiimide (DCC) and 1-hydroxy-benzotriazole (HOBT) as condensing agents in dichloromethane (DCM) or dimethylformamide (DMF) solvent. Deprotection of the N-tert-butylcarbamate 14 using 50% trifluroacetic acid (TFA) in DCM followed by treatment of the free amino intermediate 15 with a large excess of triethylamine (N(Et)$_3$) in DCM solvent leads to the formation of the desired bicyclic 2,5-diketopiperazine (cyclic dipeptide) 16.

Enantiomerically pure compounds of the invention can be conveniently prepared by using enantiomerically pure α-amino acid 11 and α-imino amide 13 starting materials.

By manipulation of the starting materials, the full range of enantiomers of structures (II), (III), (IV) and (V), as well as racemic mixtures of these structural formulae, can be readily prepared.

α-imino amide 13 where n is 1 is available commercially. α-imino amides 13 where n>1 are either available commercially or can be readily prepared using standard techniques (see, e.g., Natt et al., 1981, J. Med. Chem. 24:682–688).

By way of example, the TRH analogues can be conveniently prepared by condensing an appropriately protected α-amino acid 20 with an appropriate α-amino amide 22 and 2-oxoazetidine-4-carboxylic acid 25 as illustrated in scheme (II), below:

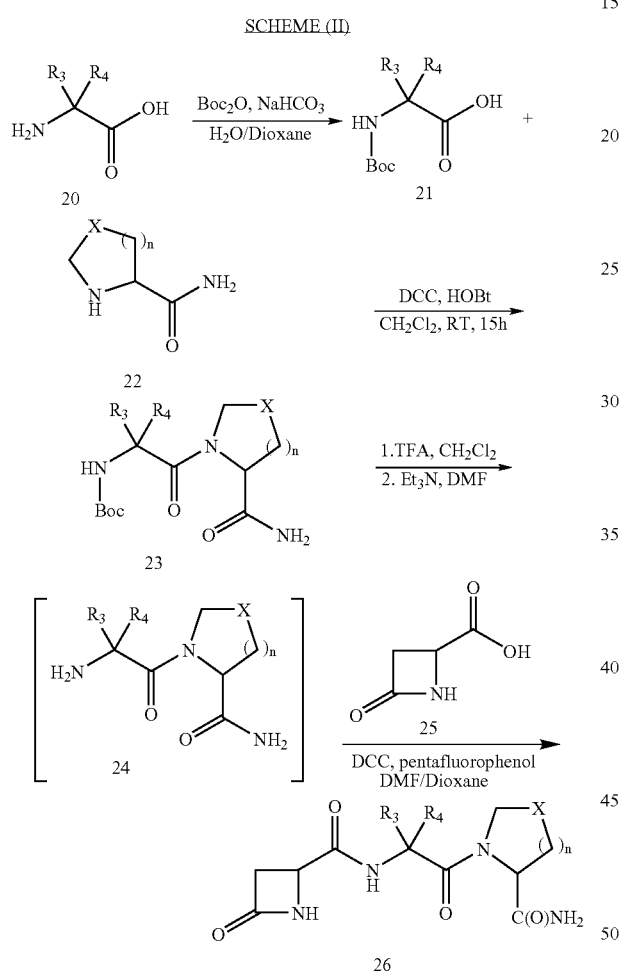

In Scheme (II), $R_3$, $R_4$, X and n are as defined for structural formula (Ib), supra. According to Scheme (II), an appropriate α-amino acid 20 is protected as the corresponding N-tert-butyl carbamate 21 using di-tert-butyl-dicarbonate ($BoC_2O$) and sodium bicarbonate in dioxane/water as solvent according to well-known methods (see, e.g., Williams et al., Chemical Approaches to the Synthesis of Peptides and Proteins, 1997, CRC Press, Boca Raton, Fla.; Atherton & Sheppard, Solid Phase Peptide Synthesis: A Practical Approach, 1989, IRL Press, Oxford, England, as well as the references cited therein). N-protected dipeptide 23 is prepared by condensing the N-tert-butylcarbamate 21 with α-amino amide 22 using 1,3-dicyclohexylarbodiimide (DCC) and 1-hydroxy benzotriazole (HOBt) as condensing agents in dichloromethane (DCM) or dimethylformamide (DMF) solvent. Deprotection of the N-tert-butylcarbamate 23 using 50% trifluoroacetic acid (TFA) in DCM followed immediately by coupling of the resulting dipeptide amide 24 with 2-oxoazetidine-4-carboxylic acid 25 using DCC/pentafluorophenol provides the desired 4-substituted 2-azetidinone TRH analogue 26, which can be purified by column chromatography.

Alternatively, the 2-azetidinone TRH analogues of the invention can be synthesized according to scheme (III).

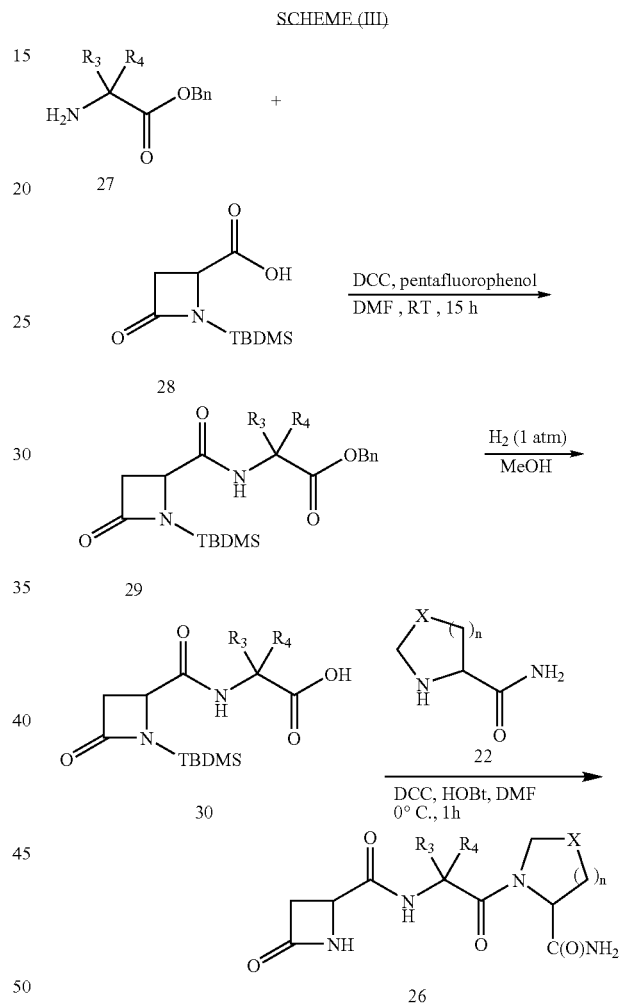

In Scheme (III), $R_3$, $R_4$, X and n are as defined for structural formula (Ib), supra. According to Scheme (III), t-butyldimethylsilyl (TBDMS) N-protected 2-oxoazetidine-4-carboxylic acid 28 is coupled at room temperature with amino acid benzyl (Bn) ester 27 using DCC/pentafluorophenol as condensing agent in DMF solvent to yield N-protected dipeptide ester 29. Catalytic hydrogenation of intermediate dipeptide 29 yields N-protected dipeptide 30, which in turn is condensed with α-amino amide 22 at 0° C. using DCC/HOBt as condensing agent in DMF solvent to yield the 2-azetidinone TRH analogue 26.

The azetidin-2-ones 25 and 28 can be synthesized according to Scheme (IV):

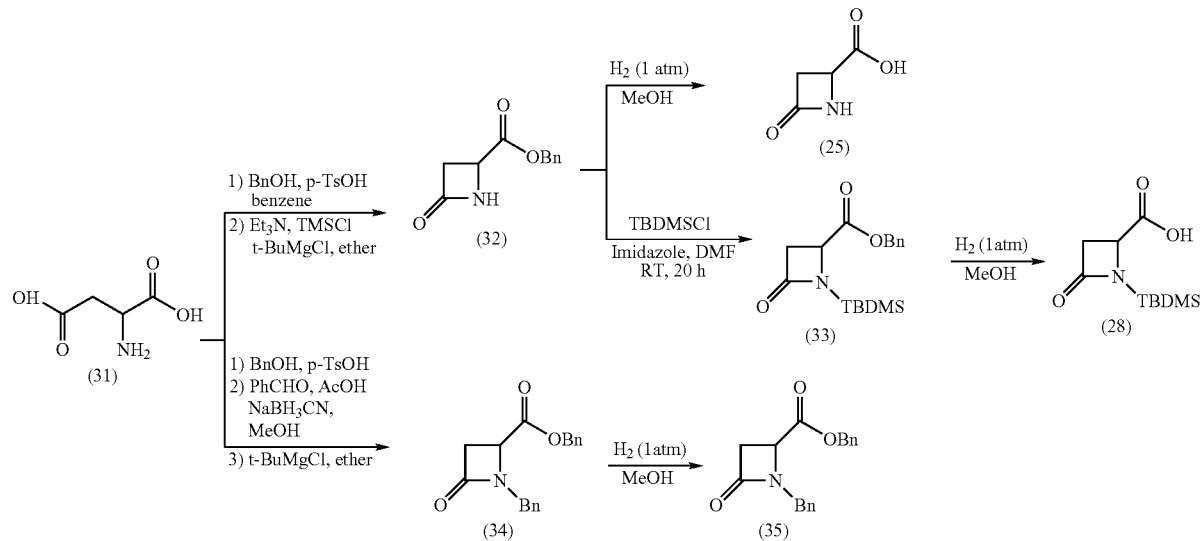

According to Scheme (IV), dibenzyl aspartate is prepared by refluxing a benzene solution of aspartate 31, benzyl alcohol (BnOH) and p-toluenesulfonic acid (TsOH) in a Dean-Stark apparatus. Reaction of this diester with triethylamine and trimethylsilyl chloride (TMSCl) followed by t-butylmagnesium chloride (t-BuMgCl) yields N-(benzyloxy-carbonyl)azetidin-2-one 32 in good yield. Catalytic hydrogenation of 32 affords 4-oxoazetidine-2-carboxylic acid 25.

The N-protected azetidin-2-one ester 33 can be prepared by silylation of N-(benzyloxycarbonyl)azetidin-2-one 32 with t-butyldimethylsilyl chloride (TBDMSCl) in the presence of imidazole in DMF solvent. Catalytic hydrogenation of ester 33 yields N-protected azetidin-2-one 28.

Preparation of N-benzyl-4-oxo-2-azetidine-3-carboxylic acid 35, which those of skill in the art can also use to synthesize the TRH analogues of the invention via slight modification of the methods described herein, can be accomplished by N-benzylation of aspartate 31 by prior imine formation followed by sodium cyanoborohydride reduction followed by cyclization with t-BuMgCl in ether solvent to yield azetidin-2-one derivative 34. Catalytic hydrogenation of derivative 34 affords N-benzyl-4-oxoazetidine-2-carboxylic acid 35.

Enantiomerically pure compounds of the invention can be conveniently prepared by using enantiomerically pure α-amino acid 20, α-amino amide 22 and aspartate 31 starting materials. By manipulation of the starting materials, the full range of stereoisomers represented by structures (IIb)–(IXb), as well as racemic mixtures of these structural formulae, can be readily prepared.

α-Amino amide 22 where n is 1 is available commercially. α-Amino amides 22 where n>1 are either available commercially or can be readily prepared using standard techniques (see, e.g., Natt et al., 1981, J. Med. Chem. 24:682–688). Enantiomerically pure α-amino acid 20 and aspartate 31 are commercially available.

Scheme V

Disulfide bridged dimers according to formula (Ic) can be prepared by mild oxidation of the appropriate sulfanyl-containing monomers according to Scheme (V).

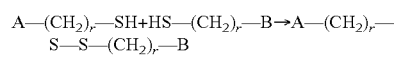

In Scheme V, A, B and r are as previously defined for structure (Ic). Mild oxidation agents include, for example, iodine. For dimers having a specified stereochemistry, enantiomerically pure starting materials may be prepared as described above. An alternative method for synthesizing heterodimer 14c is provided in the Examples.

It will be appreciated that in many instances, α-amino acid 11 or 20 may contain $R_1$ and/or $R_2$ substituents having functional groups that are reactive under the conditions used to synthesize the compounds of the invention. In such instances, the functional groups can be protected with protecting groups that are stable to the synthesis conditions. Of course, the appropriate protecting group will depend on the identity of the particular functional group requiring protection. Groups suitable for protecting a wide variety of functional groups under various synthetic conditions are well-known in the art, and can be found, for example, in Greene & Wuts, Protective Groups in Organic Synthesis, 2d Ed., 1991, John Wiley & Sons, NY. Selection of an appropriate protecting group is well within the capabilities of a skilled artisan.

An individual compound's relevant activity and potency as a neuroprotective agent, to enhance memory function and/or to treat neurological disorders may be determined using standard techniques. In general, the active compounds of the invention are those which show neuroprotective effects in standardized models of CNS injuries or neurodegenerative disorders (e.g., Alzheimer's mouse model). Neuroprotective effects can be demonstrated using cognitive or motor tasks, magnetic resonance imaging (MRI) or histological methods. Cognitive enhancing effects can be demonstrated using classical tests of spatial learning and/or working memory, e.g., Morris Water Maze, Barnes Maze, etc.

Generally, active compounds are those which exhibit less nerve cell damage on histologic tests, or which show improved behavioral outcome (i.e., improved neuroscores on motor or cognitive tasks), as compared with untreated and/or placebo- or vehicle-treated animal controls. Alternatively, active compounds are those which exhibit similar nerve cell damage on histologic tests, or similar behavioral outcome (i.e., similar neuroscores on motor or cognitive tasks), as compared with positive animal controls treated with known neuroprotective or cognition-enhancing agents. Suitable models and tests for demonstrating activity are provided in the Examples, infra.

6.1 Formulation and Routes of Administration

The compounds described herein, or pharmaceutically acceptable addition salts or hydrates thereof, can be delivered to a subject, including humans, using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

As previously discussed, a significant advantage of the compounds of the invention lies in their ability to be efficaciously administered via single bolus injection, as compared with TRH which requires continuous infusion for efficacy. Thus, while the compounds can be administered by a wide variety of routes or modes, administration by single bolus i.v. injection is preferred. They also have little autonomic or endocrine effects, making these compounds potentially safer and more capable of being used chronically as in the treatment of cognitive effects.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, the compounds of the invention can be administered in cocktails containing agents used to treat the pain and other symptoms and side effects commonly associated with neurological disorders.

The compounds can also be administered in cocktails containing other agents that are commonly used to treat neurological disorders.

The active compounds may be administered per se or in the form of a pharmaceutical composition containing the active c(s) and one or more pharmaceutically acceptable carriers, excipients or diluents. Administered compounds may be enantiomerically pure, or may be mixtures of enantiomers. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations previously described, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

6.3 Effective Dosages

Pharmaceutical compositions suitable for use with the present invention include compositions wherein the active ingredient is contained in a therapeutically effective amount, i.e., in an amount effective to achieve its intended purpose. Of course, the actual amount effective for a particular application will depend upon a variety of factors including, inter alia, the condition being treated, the age and weight of the patient and the judgment of the prescribing physician. For example, when administered as a neuroprotectant, such compositions will contain an amount of active ingredient effective to achieve this result. When administered in methods to enhance memory, such compositions will contain an amount of active ingredient effective to achieve this result. Determination of an effective amount is well within the capabilities of those skilled in the art, especially in light of the detailed disclosure herein.

For any compound described herein the therapeutically effective amount for use in humans can be readily determined from animal models. For example, a dose for humans can be formulated to achieve a circulating concentration that has been found to be effective in animals for the particular indication being treated. Useful animal models for neurological disorders that can be treated with the compounds described herein are well-known in the art, and can be found, for example, in McIntosh et al., 1989, Neuroscience 28(1):233–244; Faden, 1989, Brain Research 486:228–235; Graham et al., 1990, Neurosci. Lett. 110:124–130; Yakovlev and Faden, 1994, Mol. Chem. Neuropathy 23:179–190; Andrews et al., 1988, J. Pharmacol. Exp. Ther. 247(3): 1248–1254; Faden et al., 1989, Science 244:798–800; Faden et al., 1990, J. Pharmacal. Exp. Ther. 255(2): 451–458; Graham et al., 1993, Brain Research 632: 346–350; Soc. Neurosci. Abstr.

A therapeutically effective dose can also be determined from animal or human data for compounds which are known to exhibit similar pharmacological activities, such as TRH or, preferably, YM-14673. The applied dose can be adjusted based on the relative bioavailability, potency and in vivo half-life of the administered compound as compared with these other agents.

Adjusting the dose to achieve maximal efficacy in humans based on the methods described above and other methods that are well-known in the art is well within the capabilities of the ordinarily skilled artisan.

Of course, in the case of local administration, the systemic circulating concentration of administered compound will not be of particular importance. In such instances, the compound is administered so as to achieve a concentration at the local area effective to achieve the intended result.

For use enhancing memory and/or in treating CNS injuries (including stroke), neurodegenerative disorders such as Alzheimer's disease and neurological disorders caused by central nervous system trauma, a single i.v. bolus dose of administered compound of about 0.1 mg/kg to 10 mg/kg is considered to be effective.

Patient doses for oral administration of the compounds described herein typically range from about 0.4 mg/day to 40 mg/day, more typically from about 1 mg/day to 20 mg/day, and most typically from about 2 mg/day to 6 mg/day.

For other modes of administration, dosage amount and interval can be adjusted individually to provide plasma levels of the administered compound effective for the particular clinical indication being treated.

Typically, the compounds of the invention will be administered after spinal cord and/or brain trauma. Those of skill in the art will appreciate that in many cases, the amount of time that lapses between the trauma and compound administration may affect dosage levels. As certain benefits may be achieved by administering the compounds shortly after injury, it is preferable to administer the compounds as soon as possible following injury, regardless of the mode of administration. However, the compounds are considered to provide therapeutic benefits when administered several hours, or even several days or weeks, following injury. Moreover, when used in methods to treat neurodegenerative disorders such as, for example, Alzheimer's disease, administration even years after onset of symptoms may provide therapeutic benefits.

When used in methods to enhance cognition, particularly in methods to enhance memory function, the compounds can be administered after acute or chronic brain trauma, as discussed above. Alternatively, the compounds may be used to enhance memory in animals and humans that have not suffered brain trauma. In such instances, the compounds can be administered as part of a daily regimen, or within a few days or hours of desired improved memory performance.

Combined with the teachings provided herein, by choosing among the various active compounds and weighing factors such as potency, relative bioavailability, patient body weight, severity of adverse side-effects, preferred mode of administration, and duration between injury and treatment, an effective therapeutic treatment regimen can be planned which does not cause substantial toxicity and yet is entirely effective to treat the clinical symptoms demonstrated by the particular patient.

6.4 Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, In: *The Pharmacological Basis of Therapeutics*).

The invention having been described, the following examples are intended to illustrate, not limit, the invention.

7. EXAMPLE

Compound Syntheses

This Example demonstrates preferred methods for synthesizing certain exemplary compounds according to the invention.

Starting materials were obtained from Aldrich Chemical Co. (St. Louis, Mo.) or from other commercial suppliers. Solvents were purified as follows: diethyl ether and cyclohexane distilled from phosphorus pentoxide; THF was freshly distilled under nitrogen from sodium-benzophenone.

Infrared (IR) spectra were recorded on an ATI Mattson Genesis spectrometer. $^1$H and $^{13}$C Nuclear magnetic resonance (NMR) spectra were obtained with a Varian Unity Inova instrument at 300 and 75.46 MHz, respectively. $^1$H chemical shifts ($\delta$) are reported in ppm downfield from internal tetra-methylsilane (TMS). $^{13}$C chemical shifts are referenced to CDCl$_3$ (central peak, $\delta$=77.0 ppm), benzene-d$_6$ (central peak, $\delta$=128.0 ppm), or DMSO-d$_6$ (central peak, $\delta$=39.7 ppm).

Melting points were determined in Pyrex capillaries with a Thomas Hoover Unimelt apparatus and are uncorrected. Mass spectra were measured in the EI mode at an ionization potential of 70 eV. Thin-layer chromatography (TLC) was performed on Merck silica gel 60F$_{254}$ glass plates; column chromatography was performed using Merck silica gel (60–200 mesh). The following abbreviations are used: DMSO is dimethyl sulfoxide; ether is diethyl ether; THF is tetrahydrofuran; MeOH is methanol; EtOAc is ethyl acetate; DCM is dichloromethane, L-ProNH$_2$ is L-Prolinamide; DCC is dicyclohexylcarbodiimide; HOBt is 1-hydroxybenzotriazole; Boc$_2$O is di-tert-butyldicarbonate; Et$_3$N is triethylamine.

7.1 SYNTHESIS Of CYCLO[(1-AMINO-1-CYCLOPROPANE-CARBOXYLIC ACID)-PRO] (Compound 1a)

To a solution of 1-amino-1-cyclopropane-carboxylic acid ("ACC") (0.2 g, 1.98 mmol) in dioxane (10 mL)/water (6 mL) was added NaHCO$_3$ (0.25 g, 2.97 mmol) and Boc$_2$O (0.65 g, 2.97 mmol). The resulting mixture was stirred at 25° C. for 15 h. The solvent was evaporated and the crude residue dissolved in EtOAc (30 mL), washed with 10% HCl (30 mL), brine (30 mL), dried (Na$_2$SO$_4$) and concentrated to afford 1-(t-butoxycarbonylamino)-1-cyclopropane-carboxylic acid (N-t-Boc-ACC) (0.30 g, 75%) as a white solid: 1H NMR (CDCl$_3$+CD$_3$OD) $\delta$ 1.56 (bs, 2H), 1.45 (s, 9H), 1.52 (bs, 2H), 4.5 (bs, 1H).

To a solution of N-t-Boc-ACC (0.42 g, 2.08 mmol) in DMF (7 mL) were added DCC (0.47 g, 2.28 mmol) and HOBt (0.36 g, 2.28 mmol). The resulting mixture was stirred at 25° C. for 2 h. L-ProNH$_2$ (0.36 g, 3.13 mmol) was added and the mixture stirred at 25° C. for an additional 18 h. The white residue was filtered off and the clear solution was concentrated under reduced pressure. The residue was dissolved in EtOAc (60 mL), washed with water (2×50 mL), saturated NaHCO$_3$ (50 mL), brine (50 mL), dried (Na$_2$SO$_4$) and concentrated. Flash chromatography on silica gel (DCM/MeOH 9/1) gave N-t-Boc-ACC-L-ProNH$_2$ (0.07 g, 11%) as a white foam: $^1$H NMR (CDCl$_3$) $\delta$ 0.9–1.0 (m, 1H), 1.0–1.1 (m, 2H), 1.44 (s, 9H), 1.7–2.2 (m, 3H), 2.2–2.4 (m, 1H), 2.97 (s, 3H), 3.6–3.8 (m, 1H), 3.8–3.96 (m, 1H), 4.5–4.7 (m, 1H), 5.8 (bs, 1H), 6.3 (bs, 1H); $^{13}$C NMR (CDCl$_3$) $\delta$ 14.7, 15.5, 25.6, 28.1, 29.0, 35.9, 48.4, 61.2, 80.6, 156.7, 171.6, 175.3.

To a solution of N-t-Boc-ACC-L-ProNH$_2$ (0.06 g, 0.20 mmol) in DCM (6 mL) was added at 0° C. trifluoroacetic acid (2 mL). The resulting solution was stirred at 0° C. for 1 h then concentrated under reduced pressure. The crude residue was dissolved in DCM (10 mL) then Et$_3$N (0.5 mL) was added. This solution was stirred at 25° C. for 15 h then washed with saturated NH$_4$Cl (2×20 mL), brine (20 mL), dried (Na$_2$SO$_4$), and concentrated under reduced pressure. Flash chromatography on silica-gel (EtOAc/MeOH) gave the title compound (Compound 1a) (20 mg, 55%) as a white solid: $[\alpha]^{25}{}_D$=−155° (c=0.5, CHCl$_3$); $^1$H NMR (CDCl$_3$) $\delta$ 0.95–1.1 (m, 2H), 1.2–1.3 (m, 2H), 1.7–2.2 (m, 4H), 2.3–2.5 (m, 1H), 3.5–3.7 (m, 1H), 4.2–4.3 (m, 1H); GC-MS m/z 180 (M$^+$, 53), 124 (25), 70 (100).

7.2 SYNTHESIS OF CYCLO[(1-AMINO-1-CYCLOHEXANE-CARBOXYLIC ACID)-PRO] (Compound 2a)

To a solution of 1-(t-Boc-amino)-1-cyclohexane-carboxylic acid (0.60 g, 2.46 mmol) in DCM (10 mL) were added DCC (0.51 g, 2.46 mmol), HOBt (0.38 g, 2.46 mmol) and L-ProNH$_2$ (0.28 g, 2.46 mmol). The reaction mixture was stirred at 25° C. for 18 h. The solid was filtered and the clear eluate washed with saturated NaHCO$_3$ (50 mL), brine (50 mL), dried (Na$_2$SO$_4$) and concentrated. Flash chromatography on silica gel (DCM/MeOH 9/1) gave [1-(N-t-Boc-amino)-1-cyclohexane-carboxylic acid]-L-ProNH$_2$ (0.50 g, 60%) as a white foam: TLC (EtOAc) R$_f$ 0.3; mp 220° C.; $^1$H NMR (CDCl$_3$) δ 1.2–1.1.5 (m, 2H), 1.44 (s, 9H), 1.6–2.2 (m, 12H), 3.4–3.6 (m, 1H), 3.7–3.9 (m, 1H), 4.65 (dd, 1H, J=5.1, 8.1 Hz), 5.15 (bs, 1H), 5.22 (bs, 1H), 7.44 (bs, 1H); $^{13}$C NMR (CDCl$_3$) δ 21.1, 21.3, 24.9, 25.7, 28.3, 28.5, 31.2, 31.7, 47.9, 58.8, 62.2, 80.6, 154.8, 172.7, 175.1.

To a solution of [1-(N-t-Boc-amino)-1-cyclohexane-carboxylic acid]-L-ProNH$_2$ (0.85 g, 2.50 mmol) in DCM (10 mL) was added trifluoroacetic acid (1 mL) at 0° C. After 1 h the solution was concentrated under reduced pressure. The crude residue was dissolved in DCM (20 mL) and Et$_3$N (1.0 mL) was added. This solution was stirred at 25° C. for 15 h then washed with saturated NH$_4$Cl (2×40 mL), brine (40 mL), dried (Na$_2$SO$_4$), and concentrated under reduced pressure. Flash chromatography on silica gel (EtOAc/methanol) gave the title compound (Compound 2) (0.35 g, 63%) as a white solid: [α]$^{25}_D$=–115° (c=0.5, CHCl$_3$); $^1$H-NMR (CDCl$_3$) δ 1.2–2.1 (m, 12H), 2.25 (td, 1H, J=4.5 and 13.8 Hz), 2.36–2.2.46 (m, 1H), 3.5–3.7 (m, 2H), 4.06–4.18 (m, 1H), 6.93 (s, 1H); $^{13}$C-NMR (CDCl$_3$) δ 20.7, 20.8, 22.2, 24.6, 28.9, 31.8, 34.2, 45.6, 58.3, 59.1, 168.7, 169.5.

7.3 SYNTHESIS OF CYCLO(Trp-Pro) (Compound 3a)

To a solution of N-t-Boc-L-Trp (1.0 g, 3.29 mmol) in DCM (20 mL) were added DCC (0.79 g, 3.81 mmol), HOBt (0.55 g, 3.52 mmol) and L-ProNH$_2$ (0.41 g, 3.61 mmol). The resulting mixture was stirred at 25° C. for 18 h. The white residue was filtered off and the clear eluate concentrated under reduced pressure. The residue was diluted with EtOAc (50 mL), washed with water (2×50 mL), NaHCO$_3$ (50 mL) and brine (50 mL). The organic solution was dried (Na$_2$SO$_4$) and concentrated under reduced pressure. The crude residue was purified by flash chromatography on silica gel using DCM/MeOH (9/1) as eluant to afford N-(t-Boc)-L-Trp-L-ProNH$_2$ (0.2 g, 22%) as a white foam: $^1$H-NMR (CDCl$_3$) δ 1.46 (s, 9H), 1.8–2.3 (m, 3H), 3.1–3.3 (m, 3H), 3.55–3.70 (m, 1H), 4.45–4.55 (m, 1H), 4.8–4.9 (m, 1H), 5.3–5.5.4 (m, 1H), 5.9 (bs, 1H), 6.09 (bs, 1H), 6.9–7.4 (m, 5H), 7.6–7.7 (m, 1H), 8.54 (bs, 1H).

To a solution of N-(t-Boc)-L-Trp-L-ProNH$_2$ (0.60 g, 1.50 mmol) in DCM (10 mL) was added trifluoroacetic acid (5 mL) at 0° C. After 1 h the solution was concentrated under reduced pressure. The crude residue was dissolved in DCM (10 mL) and Et$_3$N (0.5 mL) was added. This solution was stirred at 25° C. for 15 h then washed with saturated NH$_4$Cl (2×20 mL), brine (20 mL), dried (Na$_2$SO$_4$), and concentrated under reduced pressure. Flash chromatography on silica gel (EtOAc/MeOH) gave the title compound (Compound 3) (20 mg, 55%) as a white solid: $^1$H NMR (CDCl$_3$) d 1.8–2.1 (m, 3H), 2.28–2.4 (m, 1H), 2.97 (dd, 1H, J=10.8, 15.0 Hz), 3.5–3.7 (m, 2H), 3.75 (dd, 1H, J=3.3, 15.0 Hz), 4.07 (bt, 1H, J=7.2 Hz), 4.3–4.45 (m, 1H), 5.79 (bs, 1H), 7.0–7.3 (m, 3H), 7.39 (d, 1H, J=8.1 Hz), 7.59 (d, 1H, J=7.8 Hz), 8.47 (bs, 1H); $^{13}$C NMR (CDCl$_3$) δ 22.6, 26.8, 28.3, 45.4, 54.5, 59.2, 109.8, 111.6, 118.4, 119.9, 122.7, 123.4, 126.7, 136.6, 165.5, 169.3; GC-MS m/z 283 (M+, 5), 186 (6), 154 (7), 130 (100).

7.4 SYNTHESIS OF CYCLO(t-Butyl-Cys-Pro) (Compound 4a)

To a solution of N-FMOC-L-t-butyl-cysteine (0.50 g, 1.25 mmol) in DCM (20 mL) were added DCC (0.26 g, 1.25 mmol), HOBt (0.196 g, 1.25 mmol) and L-ProNH$_2$ (0.143 g, 1.25 mmol). The resulting mixture was stirred at 25° C. for 18 h. The white residue was filtered off and the clear solution washed with saturated NaHCO$_3$ (2×50 mL), brine (50 mL), dried (Na$_2$SO$_4$), and concentrated under reduced pressure. The crude residue was purified by flash chromatography on silica gel using DCM/MeOH (9/1) as eluant to afford N-FMOC-L-t-butyl-cysteine-L-ProNH$_2$ (0.55 g, 89%) as a white foam: $^1$H-NMR (CDCl$_3$) δ 1.32 (s, 9H), 1.9–2.1 (m, 3H), 2.3–2.4 (m, 1H), 2.8–3.0 (m, 2H), 3.7–3.8 (m, 2H), 4.15–4.25 (m, 2H), 4.6–4.8 (m, 2H), 5.7 (bs, 1H), 5.90 (d, 1H, J=8.4 Hz), 6.9 (bs, 1H), 7.31 (t, 2H, J=6.6 Hz), 7.40 (t, 2H, J=7.5 Hz), 7.59 (d, 2H, J=7.5 Hz), 7.76 (d, 2H, J=7.8 Hz); $^{13}$C NMR (CDCl$_3$) δ 24.5, 28.3, 30.8, 31.3, 43.3, 47.0, 47.8, 51.7, 60.1, 67.2, 120.0, 125.0, 125.1, 127.0, 127.7, 141.2, 143.7, 155.6, 170.7, 173.4.

N-FMOC-L-t-Butyl-cysteine-L-ProNH$_2$ (0.40 g, 0.807 mmol) was dissolved in piperidine (5 mL). This solution was stirred at 25° C. for 10 h then concentrated under vacuum. Flash chromatography on silica gel (EtOAc/MeOH 9/1) gave the title compound (Compound 4a) (0.20 g, 97%) as a white foam: $^1$H NMR (CDCl$_3$) δ 1.36 (s, 9H), 1.8–2.2 (m, 3H), 2.3–2.5 (m, 1H), 2.66 (dd, 1H, J=10.8, 13.2 Hz), 3.4–3.7 (m, 3H), 4.0–4.2 (m, 2H), 6.52 (bs, 1H); $^{13}$C NMR (CDCl$_3$) d 22.5, 28.2, 29.5, 30.9, 43.1, 45.454.2, 59.2, 164.5, 169.1; GC-MS m/z 256 (M+, 8), 200 (11), 154 (35), 57 (100).

7.5 SYNTHESIS OF DIBENZYL L-ASPARTATE

A mixture of L-aspartic acid (12.5 g, 0.095 mol), benzyl alcohol (30 mL), p-toluenesulfonic acid monohydrate (19 g, 0.1 mol), and benzene (150 mL) was refluxed for 8 h under a Dean-Stark apparatus. After cooling, ether (150 mL) was added with stirring, and a white precipitate was filtered off and washed with ether. The collected white salt was mixed with H$_2$O (200 mL) and treated with a saturated solution of NaHCO$_3$ (200 mL), and the mixture was extracted with CHCl$_3$ (3×200 mL). The collected organic phases were dried over sodium sulfate, filtered and concentrated under reduced pressure to afford the title compound (24.8 g, 83.2%) as a colorless oil: $^1$H NMR (CDCl$_3$) δ 2.77 (dd, 1H, J=7.2 and 16.5 Hz), 2.86 (dd, 1H, J=4.8 and 16.5 Hz), 3.87 (dd, 1H, J=4.8 and 6.9 Hz), 5.10 (s, 2H), 5.13 (s, 2H), 7.22–7.41 (m, 10H).

7.6 SYNTHESIS OF DIBENZYL N-BENZYL-L-ASPARTATE

To a solution of dibenzyl-L-aspartate (0.95 g, 3.03 mmol) in MeOH (10 mL) were added benzaldehyde (0.39 g, 3.33 mmol, 1.1 equiv.), acetic acid (0.21 mL, 3.64 mmol, 1.2 equiv.), and sodium cyanoborohydride (0.38 mg, 6.06 mmol, 2.0 equiv.). The resulting solution was stirred at RT for 1 h, then concentrated under reduced pressure. The crude residue was diluted with EtOAc (50 mL), washed with a saturated solution of NaHCO$_3$ (2×50 mL), dried over sodium sulfate and concentrated under reduced pressure. The oily residue was purified by silica gel column chromatography (EtOAc/hexane 1/9) to afford the title compound (1.2 g, 98%) as a colorless oil: R$_f$ 0.6 (EtOAc/hexane 2/8); $^1$H NMR (CDCl$_3$) δ 2.72 (dd, 1H, J=7.0 and 15.8 Hz), 2.80 (dd, 1H, J=5.7 and 15.8 Hz), 3.69 (d, 1H, J=13.2 Hz), 3.73

(dd, 1H, J=6.2 and 7.0 Hz), 3.85 (d, 1H, J=12.8 Hz); 5.07 (br d, 2H, J=2.0 Hz), 5.13 (s, 2H), 7.20–7.40 (m, 15H).

7.7 SYNTHESIS OF BENZYL (S)-N-BENZYL-4OXOAZETIDINE-2-CARBOXYLATE (Compound 34)

A solution of dibenzyl N-benzyl-L-aspartate (0.3 g, 0.74 mmol) in ether (10 mL) was cooled to −5° C. and an ethereal solution of $^t$BuMgCl (0.74 mL, 2.0 M in ether, 2 equiv) was added dropwise. The resulting mixture was stirred for 2 h at 0° C. then at RT for an additional 1 h. The reaction was quenched with 5 mL of 2 N aqueous HCl (saturated with NH$_4$Cl). After separation of the ethereal layer, the aqueous layer was extracted with EtOAc (2×20 mL). The combined organic phases were washed with brine (50 mL), dried and concentrated under reduced pressure. The oily residue was purified by silica gel column chromatography (EtOAc/hexane 2/6) to provide the title compound (0.22 g, 95%) as a colorless oil: $[\alpha]^{25}_D$ −65° (c 0.7, MeOH); R$_f$ 0.7 (EtOAc/hexane 3/4); $^1$H NMR (CDCl$_3$) δ 3.03 (dd, 1H, J=2.6 and 14.5 Hz), 3.20 (dd, 1H, J=5.3 and 14.5 Hz), 3.95 (dd, 1H, J=2.6 and 5.3 Hz), 4.13 (d, 1H, J=15.4 Hz), 4.76 (d, 1H, J=14.9 Hz), 5.12 (s, 2H), 7.15–7.42 (m, 10H).

7.8 SYNTHESIS OF BENZYL (S)-4-OXOAZETIDINE-2-CARBOXYLATE (Compound 32)

To a solution of dibenzyl L-aspartate (3.23 g, 10.3 mmol) in ether (40 mL) cooled at 0° C. was added dropwise Et$_3$N (1.72 mL, 12.4 mmol, 1.2 equiv) followed by TMSCl (1.44 mL, 11.34 mmol, 1.1 equiv). The resulting mixture was stirred for 1 h at 0° C., then cooled to −5° C., and an ethereal solution of $^t$BuMgCl (31.8 mL, 2.0 M in ether, 2 equiv) was added dropwise. The resulting mixture was stirred for 2 h at 0° C. and quenched with 15 mL of 2 N aqueous HCl (saturated with NH$_4$Cl). After separation of the ethereal layer, the aqueous layer was extracted with EtOAc (2×40 mL). The combined organic phases were washed with brine (50 mL), dried and concentrated under reduced pressure. To the oily residue was added 10 mL of EtOAc, and crystals were collected by filtration to provide the title compound (1.0 g, 47%) as a white solid. In addition, the mother liquor was concentrated and purified by silica gel column chromatography (EtOAc/hexane 6/4) to provide another 0.51 g of the desired product: mp 138–139° C. (EtOAc) (lit: mp 140° C.; Weis, C. D. *J. Org. Chem.* 1986, 51, 558–561); $[\alpha]^{25}_D$ −50.4° (c 1.5, CHCl$_3$) (lit.: $[\alpha]^{25}_D$ −41.80 (CHCl$_3$); Weis, C. D. *J. Org. Chem.* 1986, 51, 558–561); R$_f$ 0.6 (EtOAc/hexane 8/2); $^1$H NMR (DMSO-d$_6$) δ 2.91 (dt, 1H, J=1.5 and 14.4 Hz), 3.25 (ddd, 1H, J=1.5, 6.0 and 14.7 Hz), 4.21 (dd, 1H, J=2.4 and 5.7 Hz), 7.30–7.48 (m, 5H), 8.42 (br s, NH).

To a solution of the preceding intermediate (0.50 g, 2.43 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the title compound (0.26 g, 93%) as a viscous oil: $^1$H NMR (methanol-d$_4$) δ 2.49 (dd, 1H, J=2.1 and 14.4 Hz), 2.84 (dd, 1H, J=5.7 and 14.7 Hz), 3.70 (dd, 1H, J=2.1 and 5.7 Hz).

7.9 SYNTHESIS OF (S)-1-BENZYL-4-OXOAZETIDINE-2-CARBOXYLIC ACID (Compound 35)

To a solution of Compound 34 (0.35 g, 1.19 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the title compound (0.24 g, 95%) as a viscous oil: $^1$H NMR (CDCl$_3$) δ 3.10 (dd, 1H, J=2.2 and 14.4 Hz), 3.28 (dd, 1H, J=5.7 and 14.5 Hz), 3.98 (dd, 1H, J=2.2 and 5.7 Hz), 4.15 (d, 1H, J=14.9 Hz), 4.85 (d, 1H, J=15.0 Hz), 7.20–7.40 (m, 5H), 10.02 (br s, 1H).

7.10 SYNTHESIS OF BENZYL (S)-N-(tert-BUTYLDIMETHYLSILYL)-4-OXOAZETIDINE-2-CARBOXYLATE (Compound 33)

A mixture of Compound 32 (0.5 g, 2.44 mmol), DMF (5 mL), imidazole (0.25 g, 3.65 mmol, 1.5 equiv), and tert-butyldimethylsilyl chloride (0.55 g, 3.65 mmol, 1.5 equiv) was stirred at RT for 20 h. The reaction mixture was stirred with ether (50 mL), washed with a saturated solution of NH$_4$Cl (2×50 mL), and brine (50 mL), dried over sodium sulfate, and concentrated under reduced pressure. The crude mixture was purified by silica gel column chromatography (EtOAc/hexane 3/7) to afford the title compound (0.65 g, 84%) as a colorless oil: R$_f$ 0.8 (EtOAc/hexane 1/1); $^1$H NMR (CDCl$_3$) δ 0.06 (s, 3H), 0.25 (s, 3H), 0.92 (s, 9H), 3.07 (dd, 1H, J=3.1 and 15.4 Hz), 3.33 (dd, 1H, J=6.2 and 15.4 Hz), 4.07 (dd, 1H, J=3.1 and 6.2 Hz), 5.19 (s, 2H), 7.37 (br 1, 5H).

7.11 SYNTHESIS OF (S)-N-(tert-BUTYLDIMETHYLSILYL)-4-OXO-AZETIDIN-2 CARBOXYLIC ACID (Compound 28)

To a solution of Compound 33 (0.64 g, 2.0 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the title compound (0.37 g, 80%): $[\alpha]^{25}_D$ −92° (c 1.0, CHCl$_3$); mp 135–136° C.; $^1$H NMR (CDCl$_3$) δ 0.16 (s, 3H), 0.31 (s, 3H), 0.97 (s, 9H), 3.14 (dd, 1H, J=2.6 and 15.4 Hz), 3.42 (dd, 1H, J=6.2 and 15.4 Hz), 4.09 (dd, 1H, J=2.6 and 6.2 Hz).

7.12 Synthesis of Compound 14c

7.12.1 N,N'-BIS(TERT-BUTOXYCARBONYL)-L-CYSTINE

L-Cystine (2.0 g, 8.32 mmol) was dissolved in a mixture of dioxane (30.0 mL) and 0.5 M NaOH (30.0 mL). To this solution was added di-tert-butyl dicarbonate (3.6 g, 16.6 mmol, 2.0 equiv.) and the resulting mixture stirred at RT for 15 h. The reaction mixture was concentrated under reduced pressure and diluted with EtOAc (50 mL) and 1 M HCl (30 mL). The aqueous solution was extracted with EtOAc (2×50 mL), and the combined organic phases were washed with brine (100 mL), dried over sodium sulfate, and concentrated under reduced pressure to afford the title compound (3.1 g, 83%) as a white solid: $^1$H NMR (CDCl$_3$+methanol-d$_4$) δ 1.45 (s, 18H), 3.20 (dd, 2H, J=6.0 and 13.8 Hz), 3.25 (dd, 2H, J=4.8 and 13.8 Hz), 3.78 (br s, 2NH), 4.50–4.60 (m, 2H).

7.12.2 N$^1$,N'-[N,N'-Bis(tert-butoxycarbonyl)-L-cystyl]di-L-prolinamide

To a solution of N,N'-[bis(tert-butoxycarbonyl)]-cystine (1.0 g, 2.27 mmol) in EtOAc (15 mL) and DMF (5 mL) were added DCC (1.03 g, 5.0 mmol, 1.1 equiv) and HOBt (0.78 g, 5.0 mmol, 1.1 equiv). The resulting mixture was stirred at 25° C. for 2 h. L-ProNH$_2$ (0.53 g, 4.65 mmol, 1.03 equiv) was added and the mixture stirred at 25° C. for an additional 18 h. The white residue was filtered off and the clear solution concentrated under reduced pressure. The residue was dissolved in CHCl$_3$ (60 mL), and the solution was washed with, saturated NaHCO$_3$ (50 mL) and brine (50 mL), dried (Na$_2$SO$_4$), and concentrated under reduced pressure. The crude oil was purified by silica gel column chromatography (DCM/MeOH 9/1) to afford the title compound (1.2 g, 83%) as a white solid: R$_f$ 0.4 (CH$_2$Cl$_2$/MeOH 9/1); mp 128–131° C.; $^1$H NMR (CDCl$_3$) δ 1.44 (s, 18H), 1.90–2.40 (m, 8H), 3.01 (dd, 2H, J=6.0 and 13.2 Hz), 3.16 (dd, 2H, J=6.3 and 13.5 Hz), 3.70–3.82 (m, 4H), 4.50–4.65 (m, 2H), 4.70–4.82 (m, 2H), 5.75 (br d, 2H, J=8.7 Hz), 6.37 (br s, 2H), 6.78 (br s, 2H).

7.12.3 (Compound 14c)

The preceding compound (1.25 g, 1.97 mmol) was dissolved in CH$_2$Cl$_2$ (20 mL) and the solution cooled to 0° C. Trifluoroacetic acid (15 mL) was added and the resulting solution stirred at 0° C. for 2 h. Concentration at RT under reduced pressure yielded a crude residue that was triturated with ether (40 mL) to afford the trifluoroacetate salt of L-cystyldi-L-prolinamide as a white solid. The product was dried and used for the subsequent reaction as it was. It was dissolved in DMF (6 mL), the solution was cooled at 0° C., and Et$_3$N (0.30 mL, 2.2 mmol, 1.1 equiv) was added dropwise.

In a mixture of dioxane (10 mL) and DMF (3.4 mL) were dissolved at 0° C. (S)-4-oxo-azetidine-2-carboxylic acid (0.51 g, 4.44 mmol, 1.1 equiv), DCC (0.97 g, 4.44 mmol, 1.1 equiv), and pentafluorophenol (0.87 g, 4.44 mmol, 1.1 equiv). The resulting mixture was stirred at 0° C. for 1.5 h then the above solution of the free amine was added and the mixture stirred an additional 2 h at 0° C. Insoluble matters were filtered off and the filtrate was concentrated under reduced pressure. The crude residue was purified by silica gel column chromatography (CHCl$_3$/MeOH/NH$_3$ aq. 40/10/1) to afford the title compound (0.50 g, 41%) as a white solid: R$_f$ 0.3 (CHCl$_3$/MeOH/NH$_3$aq 40/10/1); $^1$H NMR (methanol-d$_4$) δ 1.80–2.40 (m, 8H), 2.80–2.98 (m, 4H), 3.20–3.30 (m, 2H), 3.46–3.66 (m, 6H), 3.75–3.90 (m, 4H), 4.18 (dd, 2H, J=2.4 and 5.4 Hz), 4.24–4.34 (m, 4H), 4.41 (dd, 2H, J=4.5 and 8.4 Hz), 4.50–4.58 (m, 2H), 5.03 (dd, 2H, J=4.5 and 9.6 Hz).

7.13 Synthesis of YM-14637

7.13.1 N$^α$-(tert-BUTOXYCARBONYL)-L-HISTIDYL-L-PROLINAMIDE

To a solution of N$^α$-(tert-butoxycarbonyl)-L-histidine (0.5 g, 1.96 mmol) in DMF (10 mL) were added DCC (0.44 g, 2.15 mmol, 1.1 equiv) and HOBt (0.34 g, 2.15 mmol, 1.1 equiv). The resulting mixture was stirred at 25° C. for 2 h. L-ProNH$_2$ (0.23 g, 2.01 mmol, 1.03 equiv) was added and the mixture stirred at 25° C. for an additional 18 h. The white residue was filtered off and the clear solution concentrated under reduced pressure. The crude residue was purified by silica gel column chromatography (CHCl$_3$/MeOH/NH$_3$ 40/10/1) to afford the title compound (0.70 g, 73%) as a white solid: mp 97–101° C.; $^1$H NMR (CDCl$_3$) δ 1.44 (s, 9H), 1.86–2.08 (m, 2H), 2.09–2.26 (m, 2H), 3.00–3.16 (m, 2H), 3.20–3.38 (m, 1H), 3.60–3.70 (m, 1H), 4.51 (t, 1H, J=6.6 Hz), 4.57–4.70 (m, 1H), 5.59 (br s, 1H), 6.20 (br s, 1H), 6.84 (s, 1H), 7.42 (s, 1H).

7.13.2 N$^α$-[(S)-4-OXO-AZETIDINE-2-CARBONYL]-L-HISTIDYL-L-PROLINAMIDE (YM-14673)

N$^α$-(tert-butoxycarbonyl)-L-histidyl-L-prolinamide (4.0 g, 8.80 mmol) was dissolved in CH$_2$Cl$_2$ (30 mL) and the solution cooled to 0° C. Trifluoroacetic acid (25 mL) was added and the resulting solution stirred at 0° C. for 1 h. Concentration at RT under reduced pressure yielded a crude residue that was triturated with ether (40 mL) to afford the trifluoroacetate salt of L-histidyl-L-prolinamide as a white solid. The product was dried and used for the subsequent reaction as it was. It was dissolved in DMF (6 mL), and the solution was cooled to 0° C.; then Et$_3$N (0.53 mL, 3.82 mmol, 1.05 equiv) was added dropwise.

In a mixture of dioxane (20 mL) and DMF (7 mL) were dissolved at 0° C. (S)-4-OXO azetidine-2-carboxylic acid (1.02 g, 8.80 mmol, 1.0 equiv), DCC (2.01 g, 9.74 mmol, 1.1 equiv), and pentafluorophenol (1.38 g, 9.74 mmol, 1.1 equiv). The resulting mixture was stirred at 0° C. for 1.5 h then the above solution of the free amine was added and the mixture stirred an additional 2 h at 0° C. Insoluble matters were filtered off and the filtrate was concentrate under reduced pressure. The crude residue was purified by silica gel column chromatography (CHCl$_3$/MeOH/NH$_3$ 40/10/1) to afford the title compound (2.66 g, 87%) as a white solid: $^1$H NMR (DMSO-d$_6$) δ 1.74–1.90 (m, 3H), 1.92–2.10 (m, 1H), 2.65 (d, 1H, J=14.4 Hz), 2.83 (dd, 1H, J=5.7 and 14.7 Hz), 2.96 (dd, 1H, J=7.8 and 14.4 Hz), 3.09 (dd, 1H, J=5.1 and 14.1 Hz), 3.20–3.46 (m, 2H), 3.50–3.3.64 (m, 1H), 4.02 (dd, 1H, J=2.1 and 5.1 Hz), 4.18–4.25 (m, 1H), 4.66 (dd, 1H, J=7.2 and 13.5 Hz), 6.93 (s, 1H), 6.98 (br s, 1H), 7.57 (s, 1H), 8.03 (br s, 1H), 8.14 (br s, 1H), 8.38 (d, 1H, J=7.2 Hz).

7.14 SYNTHESIS OF N$^α$-[(S)-4-OXO-AZETIDINE-2-CARBONYL]-L-(3',5'-DIIODO HISTIDYL-L-PROLINAMIDE

N$^α$-[(S)-4-oxo-azetidine-4-carbonyl]-L-histidyl-L-prolinamide (0.40 g, 1.15 mmol) and NaI (0.17 g, 1.15 mmol, 1.0 equiv) were stirred in a pH 7.5 Na$_2$HPO$_4$—NaH$_2$PO$_4$ buffer (19 mL, 0.1 M) at RT. Chloramine-T (N-chloro-p-toluenesulfonamide sodium salt trihydrate) (0.26 g, 1.15 mmol, 1.0 equiv) dissolved in H$_2$O (1 mL) was added. After 20 min, the reaction was terminated by adding Na$_2$S$_2$O$_5$ (0.18 g, 1.15 mmol, 1.0 equiv). TLC analysis of the product mixture showed the formation of the diiodo derivative together with the 3-monoiodohistidine derivative. The mixture was lyophilized and the resultant residue purified by silica gel column chromatography(CHCl$_3$/MeOH/NH$_3$ 40/10/1) to afford the two iodo derivatives.

N$^\alpha$-[(S)-4-oxo-azetidine-2-carbonyl]-L-(3',5'-diiodo histidyl)-L-prolinamide (0.10 g, 15%): $^1$H NMR (methanol-d$_4$) δ 1.90–2.10 (m, 3H), 2.20–2.37 (m, 1H), 2.85 (dd, 1H, J=2.4 and 14.7 Hz), 2.90–3.15 (m, 3H), 3.22 (dd, 1H, J=5.4 and 14.7 Hz), 3.65–3.80 (m, 1H), 4.15 (dd, 1H, J=2.4 and 5.4 Hz), 4.44 (dd, 1H, J=5.1 and 8.4 Hz), 4.70–4.80 (m, 1H). N$^\alpha$-[(S)-4-OXO-azetidine-2-carbonyl]-L-(3'-iodo histidyl-L-prolinamide (0.14 g, 26%): $^1$H NMR (methanol-d$_4$) δ 2.40–2.70 (m, 3H), 2.70–2.90 (m, 1H), 2.86 (dd, 1H, J=2.4 and 14.7 Hz), 3.00–3.12 (m, 1H), 3.12 (dd, 1H, J=6.9 and 15.9 Hz), 3.22 (dd, 1H, J=5.4 and 14.7 Hz), 3.38–3.48 (m, 1H), 3.70–3.85 (m, 1H), 4.16 (dd, 1H, J=2.4 and 5.7 Hz), 4.46 (dd, 1H, J=5.7 and 8.4 Hz), 7.70 (s, 1H).

7.15 SYNTHESIS OF N-[2-[N-[(S)-4-OXO-AZETIDINE-2-CARBONYL]AMINO]ISOBUTYRYL]-L-PROLINAMIDE (Compound 9b)

7.15.1 2-(tert-BUTOXYCARBONYLAMINO) ISOBUTYRIC ACID

α-Aminoisobutyric acid (1.0 g, 9.70 mmol) was dissolved in a mixture of dioxane (15.0 mL) and 0.5 M NaOH (15.0 mL). To this solution was added di-tert-butyl dicarbonate (2.5 g, 11.64 mmol, 1.2 equiv.) and the resulting mixture stirred at RT for 15 h. The reaction mixture was concentrated under reduced pressure and diluted with EtOAc (50 mL) and 1 M HCl (30 mL). The aqueous solution was extracted with EtOAc (2×30 mL) and the combined organic phases were washed with brine (40 mL), dried over sodium sulfate, and concentrated under reduced pressure to afford the title compound (1.3 g, 67%) as a white solid: mp 122–123° C.; $^1$H NMR (CDCl$_3$+methanol-d$_4$) δ 1.44 (s, 9H), 1.51 (s, 6H), 3.99 (br s, NH).

7.15.2 SYNTHESIS OF N$^1$-[2-[N-(tert-BUTOXYCARBONYL)AMINO]ISOBUTYRYL-L-PROLINAMIDE To a solution of (tert-butoxycarbonylamino) isobutyric acid (0.68 g, 3.33 mmol) in EtOAc (15 mL) and DMF (5 mL) were added DCC (0.76 g, 3.66 mmol, 1.1 equiv) and HOBt (0.57 g, 3.66 mmol, 1.1 equiv). The resulting mixture was stirred at 25° C. for 2 h. L-ProNH$_2$ (0.40 g, 3.50 mmol, 1.05 equiv) was added and the mixture stirred at 25° C. for an additional 18 h. The white residue was filtered off and the clear solution concentrated under reduced pressure. The residue was dissolved in EtOAc (60 mL), and the solution was washed with water (2×50 mL), saturated NaHCO$_3$ (50 mL), and brine (50 mL), dried (Na$_2$SO$_4$), and concentrated under reduced pressure. Flash chromatography on silica gel (DCM/MeOH 9/1) gave the title compound (0.4 g, 40%) as a white solid: $^1$H NMR (methanol-d$_4$) δ 1.36 (s, 3H), 1.45 (br s, 12H), 1.80–2.03 (m, 3H), 2.18–2.32 (m, 1H), 3.52–3.64 (m, 1H), 3.84–3.96 (m, 1H), 4.44 (dd, 1H, J=5.7 and 9.0 Hz), 4.60 (br s, NH).

7.15.3 N-[2-[N-[(S)-4-OXO-AZETIDINE-2-CARBONYL]AMINO]ISOBUTYRYL]-L-PROLINAMIDE (Compound 9b)

The preceding was converted to the title compound using the method described in Section 6.10.2, supra. $^1$H NMR (DMSO-d$_6$) δ 1.48 (s, 3H), 1.51 (s, 3H), 1.80–2.05 (m, 3H), 2.12–2.26 (m, 1H), 2.94 (dd, 1H, J=7.9 and 17.6 Hz), 3.10 (dd, 1H, J=4.4 and 17.6 Hz), 3.45–3.57 (m, 1H), 3.62–3.74 (m, 1H), 4.26 (dd, 1H, J=4.4 and 7.9 Hz), 4.41 (dd, 1H, J=5.3 and 8.8 Hz), 4.89 (br s, 4H).

7.16 SYTHESIS OF N$^1$-[1-[N-[(S)-4-OXO-AZETIDINE-2-CARBONYL]AMINO]CYCLOPROPANE-CARBONYL]PROLINAMIDE (Compound 10b)

7.16.1 BENZYL 1-(tert-BUTOXYCARBONYLAMINO)-CYCLOPROPANE CARBOXYLIC ACID 1-amino cyclopropanecarboxylic acid (0.3 g, 2.96 mmol) was dissolved in a mixture of dioxane (7.0 mL) and NaOH 0.5M (7.0 mL). To this solution was added di-tert-butyl dicarbonate (1.0 g, 4.44 mmol, 1.5 equiv.) and the resulting mixture stirred at RT for 15 h. The reaction mixture was concentrated under reduced pressure and diluted with EtOAc (50 mL) and 1 M HCl (30 mL). The aqueous solution was extracted with EtOAc (2×30 mL), and the combined organic phases were washed with brine (40 mL), dried over sodium sulfate, and concentrated under reduced pressure to afford the title compound (0.5 g, 84%) as a white solid: $^1$H NMR (CDCl$_3$+methanol-d$_4$) δ 1.10–1.20 (m, 2H), 1.45 (s, 9H), 1.46–1.60 (m, 2H), 3.90 (br s, NH).

7.16.2 BENZYL 1-(tert-BUTOXYCARBONYLAMINO) CYCLOPROPANECARBOXYLATE

To a solution of 1-(t-butoxycarbonylamino) cyclopropanecarboxylic acid (0.5 g, 2.48 mmol) in DMF (10 mL) were added Et$_3$N (0.83 mL, 5.95 mmol, 2.4 equiv.) and benzyl bromide (0.71 mL, 5.95 mmol, 2.4 equiv.) The resulting solution was stirred at RT for 15 h, then diluted with ether (50 mL), washed with a saturated solution of NH$_4$Cl (50 mL) and brine (50 mL), dried (Na$_2$SO$_4$), and concentrated under reduced pressure. The crude mixture was purified by silica gel column chromatography (EtOAc/hexane 1/9) to afford the title compound (0.5 g, 69%) as a white solid: mp 118–120° C.; R$_f$ 0.8 (EtOAc/hexane 2/5); $^1$H NMR (CDCl$_3$) δ 1.15–1.22 (m, 2H0, 1.42 (s, 9H), 1.50–1.62 (m, 2H), 5.14 (s, 2H), 7.30–7.44 (m, 5H).

7.16.3 BENZYL 1-AMINOCYCLOPROPANECARBOXYLATE

Benzyl 1-(t-butoxycarbonylaminocyclopropane-carboxylate (0.49 g, 1.68 mmol) was dissolved in CH$_2$Cl$_2$ (5 mL) and the solution cooled to 0° C. Trifluoroacetic acid (5 mL) was added and the resulting solution stirred at 0° C. for 1 h. Concentration at RT under reduced pressure yielded a crude residue that was diluted with CHCl$_3$ (30 mL), and the solution was washed with a saturated solution of NaHCO$_3$ (30 mL) and brine (30 mL), dried (Na$_2$SO$_4$), and concentrated under reduced pressure to afford the title compound (0.31 g, 96%) as a colorless oil which was used as it is in the next step: $^1$H NMR (CDCl$_3$) δ 1.00–1.12 (m, 2H), 1.25–1.40 (m, 2H), 2.01 (br s, NH$_2$), 5.12 (s, 2H), 7.25–7.40 (m, 5H)

7.16.4 BENZYL [(S)1-[N-tert-BUTYLDIMETHYLSILYL)-4-OXO-AZETIDINE-2-CARBONYL]AMINO]-CYCLOPROPANECARBOXYLATE To a solution of the (S)-N-(tert-butyldimethylsilyl)-4-oxo-azetidine-carboxylic acid 22 (0.26 g, 1.15 mmol) in EtOAc (10 mL) were added DCC (0.26 g, 1.26 mmol, 1.1 equiv) and HOBt (0.20 g, 1.1 mmol, 1.1 equiv). The resulting mixture was stirred at 25° C. for 2 h. Benzyl 1-aminocyclopropane-carboxylate (0.53 g, 4.65 mmol, 1.03 equiv) was added and the mixture stirred at 25° C. for an additional 18 h. The white residue was filtered off and the clear solution concentrated under reduced pressure. The residue was dissolved in CHCl$_3$ (40 mL), and the solution was washed with saturated NaHCO$_3$ (40 mL) and brine (40 mL), dried (Na$_2$SO$_4$), and concentrated under reduced pressure. The crude oil was purified by silica gel column chromatography (EtOAc/hexane 1/1) to afford the title compound (0.46 g, 98%) as a white foam: R$_f$ 0.4 (EtOAc/hexane 4/2); $^1$H NMR (CDCl$_3$) δ 0.09 (s, 3H), 0.27 (s, 3H), 0.95 (s, 9H), 1.10–1.30 (m, 2H), 1.56–1.74 (m, 2H), 2.90 (dd, 1H, J=2.6 and 15.4 Hz), 3.28 (dd, 1H, J=6.2 and 15.8 Hz), 3.92 (dd, 1H, J=2.6 and 6.2 Hz), 5.07 (d, 1H, J=12.3 Hz), 5.13 (d, 1H, J=12.3 Hz), 6.58 (br s, NH), 7.20–7.40 (m, 5H).

7.16.5 [(S)-1-[N-tert-BUTYLDIMETHYLSILYL)4-OXO-AZETIDINE-2-CARBONYL]AMINO]CYCLOPROPANECARBOXYLIC ACID To a solution of the preceding intermediate (0.45 g, 1.12 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the title compound (0.26 g, 75%) as a white solid: $^1$H NMR (CDCl$_3$+methanol-d$_4$) δ 0.13 (s, 3H), 0.31 (s, 3H), 0.96 (s, 9H), 1.10–1.15 (m, 2H), 1.55–1.64 (m, 2H), 3.06 (dd, 1H, J=2.6 and 15.4 Hz), 3.32 (dd, 1H, J=5.7 and 14.9 Hz), 3.97 (dd, 1H, J=2.6 and 5.7 Hz).

7.16.6 N$^1$-[1-[N-[(S)-4-OXO-AZETIDINE-2-CARBONYL]AMINO]CYCLOPROPANE-CARBONYL]-L-PROLINAMIDE (Compound 10b)

In DMF (4 mL) at 0° C. were dissolved the preceding intermediate (0.15 g, 0.48 mmol), DCC (0.12 g, 0.47 mmol, 1.1 equiv.) and pentafluorophenol (0.13 g, 0.63 mmol, 1.5 equiv.). The resulting mixture was stirred at 0° C. for 1.5 h, then L-prolinamide (66 mg, 0.46 mmol, 1.1 equiv.) was added and the mixture stirred an additional 2 h at RT. Insoluble matters were filtered off and the filtrate was concentrate under reduced pressure. The crude residue was purified by silica gel column chromatography (CHCl$_3$/MeOH 9/1) to afford the title compound (0.06 g, 42%) as a white solid: mp 162° C. dec.; $^1$H NMR (D$_2$O) δ 1.08–1.30 (m, 3H), 1.36–1.50 (m, 1H), 1.70–1.96 (m, 1H), 2.10–2.26 (m, 1H), 2.86 (br d, 1H, J=15.3 Hz), 3.25 (dd, 1H, J=5.4 and 15.3 Hz), 3.40–3.70 (m, 2H), 4.12–4.22 (m, 1H), 4.24 (t, 1H, J=7.5 Hz).

7.17 SYNTHESIS OF N$^1$-[1-[N-[(S)-4-OXO-AZETIDINE-2-CARBONYL]AMINO]-CYCLOHEXANECARBONYL-L-PROLINAMIDE (Compound 11b)

7.17.1 BENZYL 1-AMINOCYCLOHEXANECARBOXYLATE

A mixture of 1-aminocyclohexanecarboxylic acid (3.00 g, 21.0 mmol), benzyl alcohol (6.7 mL), p-toluenesulfonic acid monohydrate (4.4 g, 23.0 mmol, 1.1 equiv.), and benzene (70 mL) was refluxed for 10 h under a Dean-Stark apparatus. After cooling, ether (150 mL) was added with stirring, and a white precipitate was filtered off and washed with ether. The collected white salt was mixed with H$_2$O (80 mL) and treated with a saturated solution of NaHCO$_3$ (80 mL), and the solution was extracted with CHCl$_3$ (3×80 mL). The combined organic phases were dried over sodium sulfate, filtered and concentrated under reduced pressure to afford the title compound (1.10 g, 23%) as a colorless oil: R$_f$ 0.4 (EtOAc/hexane 4/2); $^1$H NMR (CDCl$_3$) δ 1.40–1.52 (m. 5H), 1.55–1.70 (m, 4H), 1.90–2.00 (m, 1H), 5.15 (s, 2H), 7.35 (br s, 5H).

7.17.2 BENZYL [(S)-1-[N-tert-BUTYLDIMETHYLSILYL-4-OXO-AZETIDINE-2-CARBONYL]AMINO]CYCLOHEXANECARBOXYLATE To a solution of N-(tert-butyldimethylsilyl)-4-oxo-azetidin-2-carboxylic acid (0.40 g, 1.74 mmol) in EtOAc (15 mL) were added DCC (0.43 g, 2.09 mmol, 1.2 equiv.) and HOBt (0.30 g, 1.91 mmol, 1.1 equiv). The resulting mixture was stirred at 25° C. for 2 h. Benzyl 1-aminocyclohexane carboxylate (0.43 g, 1.83 mmol, 1.05 equiv.) was added and the mixture stirred at 25° C. for an additional 18 h. The white residue was filtered off and the clear solution concentrated under reduced pressure. The residue was dissolved in CHCl$_3$ (40 mL), and the solution was washed with saturated NaHCO$_3$ (40 mL) and brine (40 mL), dried (Na$_2$SO$_4$), and concentrated under reduced pressure. The crude oil was purified by silica gel column chromatography (EtOAc/hexane 1/1) to afford the title compound (0.53 g, 68%) as a white foam: R$_f$ 0.7 (EtOAc/hexane 4/2); $^1$H NMR (CDCl$_3$) δ 0.12 (s, 3H), 0.30 (s, 3H), 0.97 (s, 9H), 1.30–1.45 (m, 3H), 1.55–1.74 (m, 3H), 1.84–2.10 (m, 4H), 2.86 (dd, 1H, J=2.6 and 15.4 Hz), 3.30 (dd, 1H, J=6.6 and 15.8 Hz), 3.90 (dd, 1H, J=2.6 and 6.6 Hz), 5.09 (d, 1H, J=12.3 Hz), 5.15 (d, 1H, J=12.3 Hz), 6.16 (br s, NH), 7.20–7.40 (m, 5H).

7.17.3 [(S)-1-[N-(tert-BUTYLDIMETHYLSILYL)-4-OXO-AZETIDINE-2-CARBONYL]AMINO]-CYCLOHEXANECARBOXYLIC ACID To a solution of the preceding intermediate (0.50 g, 1.12 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the title compound (0.38 g, 96%) as a white solid: [α]$^{25}_D$–75° (c 0.3, EtOH); mp 173–175° C.; $^1$H NMR (DMSO-d$_6$) δ 0.06 (s, 3H), 0.18 (s, 3H), 0.90 (s, 9H), 1.10–2.10 (m, 10H), 2.65 (dd, 1H, J=2.6 and 14.9 Hz), 3.24 (dd, 1H, J=5.7 and 14.9 Hz), 4.15 (dd, 1H, J=2.6 and 5.7 Hz).

7.17.4 N¹-[1-[N-[(S)-4-OXO-AZETIDINE-2-CARBONYL]AMINO]-CYCLOHEXANECARBONYL-L-PROLINAMIDE (Compound 11b)

In DMF (4 mL) at 0° C. were dissolved the preceding intermediate (0.15 g, 0.42 mmol), DCC (0.10 g, 0.47 mmol, 1.1 equiv.), and pentafluorophenol (0.12 g, 0.63 mmol, 1.5 equiv.). The resulting mixture was stirred at 0° C. for 1.5 h, then L-prolinamide (53 mg, 0.46 mmol, 1.1 equiv.) was added and the mixture stirred an additional 2 h at RT. Insoluble matters were filtered off and the filtrate was concentrate under reduced pressure. The crude residue was purified by silica gel column chromatography (CHCl$_3$/MeOH 9/1) to afford the title compound (0.11 g, 80%) as a white solid: $[\alpha]^{25}_D$ +2° (c 0.3, EtOH); mp 160° C. dec.; ¹H NMR (methanol-d$_4$) δ 1.30–2.30 (m, 13H), 2.92 (dd, 1H, J=2.2 and 14.5 Hz), 3.25 (dd, 1H, J=5.3 and 14.5 Hz), 3.26–3.32 (m, 1H), 3.34–3.44 (m, 1H), 3.60–3.80 (m, 1H), 4.26 (dd, 1H, J=2.2 and 5.3 Hz), 4.41 (dd, 1H, J=6.2 and 9.2 Hz).

7.18 SYNTHESIS OF N¹-[Nα-[(S)-4-OXO-AZETIDINE-2-CARBONYL]-L-TRYPTOPHYL-L-PROLINAMIDE (Compound 12b)

7.18.1 Nα-[(S)-N-(tert-BUTYLDIMETHYLSILYL)-4-OXO-AZETIDINE-2-CARBONYL]-L-TRYPTOPHAN BENZYL ESTER To a solution of N-(tert-butyldimethylsilyl)-4-oxo-azetidin-2-carboxylic acid (0.30 g, 1.31 mmol) in EtOAc (10 mL) were added DCC (0.30 g, 1.44 mmol, 1.1 equiv.) and pentafluorophenol (0.27 g, 1.44 mmol, 1.1 equiv). The resulting mixture was stirred at 0° C. for 1 h. L-Tryptophan benzylester (0.46 g, 1.57 mmol, 1.2 equiv.) was added and the mixture stirred at 25° C. for an additional 2 h. The white residue was filtered off and the clear solution concentrated under reduced pressure. The residue was dissolved in CHCl$_3$ (40 mL), and the solution was washed with saturated NaHCO$_3$ (40 mL) and brine (40 mL), dried (Na$_2$SO$_4$), and concentrated under reduced pressure. The crude oil was purified by silica gel column chromatography (EtOAc/hexane 2/8) to afford the title compound (0.49 g, 74%) as a white foam: $[\alpha]^{25}_D$ –70° (c 0.6, EtOH); mp 60–65° C.; ¹H NMR (CDCl$_3$) δ 0.02 (s, 3H), 0.10 (s, 3H), 0.87 (s, 9H), 2.69 (dd, 1H, J=3.08 and 15.8 Hz), 3.20–3.42 (m, 3H), 3.88 (dd, 1H, J=2.6 and 6.2 Hz), 5.02 (dt, 1H, J=6.0 and 8.4 Hz), 5.11 (s, 2H), 6.49 (br d, 1H, J=8.4 Hz), 6.78 (d, 1H, J=2.2 Hz), 7.05–7.40 (m, 5H), 7.50 (d, 1H, J=7.9 Hz), 8.17 (br s, 1H).

7.18.2 N¹-[Nα-[(S)-4-OXO-AZETIDINE-2-CARBONYL]-L-TRYPTOPHYL-L-PROLINAMIDE

To a solution of the preceding intermediate (0.30 g, 0.59 mmol) in methanol (10 mL) was added a catalytic amount of 10% Pd/C. This heterogeneous mixture was hydrogenated at 1 atm and 25° C. for 30 min. Then, after filtration through a celite pad, the resulting solution was concentrated under reduced pressure to afford the free acid (0.24 g, 98%) as a white solid which was used as it is in the next step.

The above acid intermediate was dissolved in DMF (4 mL) at 0° C., then DCC (0.13 g, 0.65 mmol, 1.1 equiv.) and pentafluorophenol (0.12 g, 0.65 mmol, 1.1 equiv.) were added. The resulting mixture was stirred at 0° C. for 1.5 h, then L-prolinamide (74 mg, 0.65 mmol, 1.1 equiv.) was added and the mixture stirred an additional 2 h at RT. Insoluble matters were filtered off and the filtrate was concentrate under reduced pressure. The crude residue was purified by silica gel column chromatography (CHCl$_3$/MeOH 9/1) to afford the title compound (0.17 g, 72%) as a white solid: ¹H NMR (D$_2$O) δ 1.60–1.80 (m, 3H), 1.90–2.10 (m, 1H), 2.70–3.30 (m, 6H), 3.98 (t, 1H, J=5.7 Hz), 4.10–4.20 (m, 1H), 4.86 (t, 1H, J=7.5 Hz), 6.90–7.10 (m, 3H), 7.32 (d, 1H, J=7.5 Hz), 7.54 (d, 1H, J=7.5 Hz).

7.19 SYNTHESIS OF N¹-[2-[(S)-4-OXO-AZETIDINE-2-CARBONYL]AMINO]-3-(1-PYRAZOLYLPROPANOYL-L-PROLINAMIDE (Compound 13b)

7.19.1 BENZYL 2-[(S—)N-(tert-BUTYLDIMETHYLSILYL)-4-OXO-AZETIDINE-2-CARBONYL]AMINO]-3-(1-PYRAZOLYL)PROPANOATE To a solution of (S-)N-(tert-butyldimethylsilyl)-4-oxo-azetidine-2-carboxylic acid (0.15 g, 0.65 mmol) in EtOAc (10 mL) were added DCC (0.15 g, 0.72 mmol, 1.1 equiv) and pentafluorophenol (0.18 g, 0.98 mmol, 1.5 equiv.). The resulting mixture was stirred at 0° C. for 1 h. Benzyl 2-amino-3-(1-pyrazolyl)propanoate¹ (0.18 g, 0.72 mmol, 1.1 equiv) was added and the mixture stirred at 25° C. for 2 h. The white residue was filtered off and the clear solution concentrated under reduced pressure. The residue was dissolved in CHCl$_3$ (40 mL), and the solution was washed with saturated NaHCO$_3$ (40 mL) and brine (40 mL), dried (Na$_2$SO$_4$), and concentrated under reduced pressure. The crude oil was purified by silica gel column chromatography (EtOAc/hexane 1/1) to afford the title compound (0.13 g, 45%) as a colorless oil: R$_f$ 0.4 (EtOAc/hexane 6/4); ¹H NMR (CDCl$_3$) δ 0.07 (s, 3H), 0.32 (s, 3H), 0.95 (s, 9H), 3.00 (dd, 1H, J=2.6 and 15.4 Hz), 3.37 (dd, 1H, J=6.2 and 15.4 Hz), 3.99 (dd, 1H, J=2.6 and 6.2 Hz), 4.48 (dd, 1H, J=3.5 and 14.1 Hz), 4.66 (dd, 1H, J=4.0 and 14.1 Hz), 5.00 (dt, 1H, J=4.0 and 7.9 Hz), 5.10 (d, 1H, J=11.9 Hz), 5.17 (d, 1H, J=12.0 Hz), 6.17 (t, 1H, J=2.2 Hz), 7.11 (d, 1H, J=1.8 Hz), 7.25–7.50 (m, 7H).

7.19.2 2-[(S)-2-AZETIDINONE-4-CARBONYLAMINO]-3-(1-PYRAZOLYL)PROPANOATE-L-PROLINAMIDE

To a solution of the preceding intermediate (0.13 g, 0.29 mmol) in methanol (10 mL) was added a catalytic amount of 10%. Pd/C. This heterogeneous mixture was hydrogenated at 1 atm and 25° C. for 30 min. Then, after filtration through a celite pad, the resulting solution was concentrated under reduced pressure to afford the free carboxylic acid (0.26 g, 75%) as a white solid used in the next step without further purification.

The above acid intermediate was dissolved in DMF (4 mL) at 0° C., then DCC (0.07 g, 0.31 mmol, 1.1 equiv.) and pentafluorophenol (0.08 g, 0.43 mmol, 1.5 equiv.) were added. The resulting mixture was stirred at 0° C. for 1.5 h, then L-prolinamide (36 mg, 0.31 mmol, 1.1 equiv.) was added and the mixture stirred an additional 2 h at RT. Insoluble matters were filtered off and the filtrate was concentrate under reduced pressure. The crude residue was purified by silica gel column chromatography (CHCl$_3$/MeOH 9/1) to afford the title compound (0.06 g, 60%) as a white solid: ¹H NMR (CDCl$_3$) δ 1.80–2.00 (m, 3H), 2.08–2.20 (m, 1H), 2.82–2.96 (m, 1H), 3.00 (dd, 1H, J=2.2 and 14.5 Hz), 3.22–3.36 (m, 1H), 3.51–3.65 (m, 1H), 4.17 (dd, 1H, J=2.2 and 5.3 Hz), 4.40–4.65 (m, 2H), 4.95–5.08 (m, 1H), 6.28 (t, 1H, J=1.8 Hz), 6.55 (br s, 1H), 7.47 (d, 1H, J=1.8 Hz), 7.55–7.66 (m, 2H), 8.01 (br s, 1H), 8.17 (d, 1H, J=7.5 Hz).

7.20 Other Compounds

Other compounds of the invention can be synthesized by routine modification of the above-described syntheses (7.1–7.19), or by other methods that are well known in the art. Appropriate starting materials are commercially available or can be synthesized using routine methods.

8.0 EXAMPLE

In Vivo Studies in Mice

This Example demonstrates the significant neuroprotective and cognitive enhancing effects of certain compounds of the invention using motor and cognitive outcome scores.

8.1 Experimental Protocol 8.1.1 Animals

Male $C_{57}Bl/6$ mice (20–25 g) were obtained from Taconic Farms (Germantown, N.Y.) and housed in an area directly adjoining surgical and behavioral rooms for at least 1 week prior to any procedures. All mice were maintained at a constant temperature (22±2° C.) and a 12 hr light/dark cycle, with lights on at 6 am and all behavioral testing performed during the light cycle. Food and water were available ad libitum.

8.1.2 Controlled Cortical Impact Device

The injury device consisted of a microprocessor-controlled pneumatic impactor with a 3.5 mm diameter tip. The impactor is vertically mounted on a mill table (Sherline, USA) which allows for precise adjustment in the vertical plane above the mouse head, which itself is secured to a stereotaxic apparatus (David Kopf Instruments, CA) attached to the instrument. The core rod of a linear voltage differential transducer (LVDT, Serotec, USA) is attached to the lower end of the impactor to allow measurement of velocities between 3.0 and 9.0 m/s. Velocity of the impactor is controlled by fine tuning both positive and negative (back) air pressures. An oscilloscope (Tektronix, USA) records the time/displacement curve produced by the downward force on the LVDT, allowing precise measurement of the impactor velocity.

8.1.3 Surgery

Surgical anesthesia was induced and maintained with 4% and 2% isoflurane respectively, using a flow rate of 1.0–1.5 l oxygen per minute. Depth of anesthesia was assessed by monitoring respiration rate and palpebral and pedal-withdrawal reflexes. The animal was then placed onto a heated pad and core body temperature was monitored and maintained at 38+/−0.2° C. The head was mounted in a stereotaxic frame and the surgical site clipped and prepared with a series of three Nolvasan scrubs followed by sterile saline rinses. A 10 mm mid-line incision was made over the skull, the skin and fascia reflected, and a 4 mm craniotomy made on the central aspect of the left parietal bone with a tissue punch (Roboz, USA). Great care was taken with the removal of the parietal bone to avoid injury to the underlying dura mater which was continuously bathed in sterile normal saline warmed to 37.5° C. The impounder tip of the pneumatic injury device was cleaned with a pad, soaked in absolute alcohol, positioned to the surface of the exposed dura and automatically withdrawn the 44 mm stroke distance. Following injury at a moderate (6.0 m/s velocity, 1 mm tissue deformation depth) level, the incision was closed with interrupted 6–0 silk sutures, anaesthesia was discontinued and the mouse was placed into a heated cage to maintain normothermia for 45 minutes post-injury. All animals were monitored carefully for at least 4 hours post-surgery and then daily. To minimize variation between animals due to anaesthesia during acute neurological testing, 20 minutes was allowed for surgery and 5 minutes for suturing for each animal.

8.1.4 Administration of Compounds

Conscious mice were placed in a mouse restrainer and injected via the lateral tail vein with either normal saline (injured controls; n=6), 1 mg/kg Compound 2a (n=8), Compound 10b (n=6), Compound 11b (n=6) or Compound 14c (n=6) at 30 minutes following controlled cortical impact injury (CCI). The values for n represents the number of mice in the particular treatment group. The investigator was blinded to drug treatment both at the time of surgery and for neurological and behavioral scoring.

8.1.5 Acute and Chronic Neurological Evaluation

Chronic neurological recovery was evaluated for all animals using a beam walking task, a method which is particularly good at discriminating fine motor coordination differences between injured and sham-operated animals. The device consisted of a narrow wooden beam 6 mm wide and 120 mm in length which was suspended 300 mm above a 60 mm-thick foam rubber pad. The mouse was placed on one end of the beam and the number of footfaults for the right hindlimb recorded over 50 steps counted in either direction on the beam. A basal level of competence at this task was established before surgery with an acceptance level of <10 faults per 50 steps.

8.1.6 Spatial Learning Evaluation

The Morris watermaze (Morris, 1984, J. Neurosci. Meth. 22:47–60) is employed to assess spatial learning by training mice to locate a hidden, submerged platform using extramaze visual information. The apparatus consists of a large, white circular pool (900 mm diameter, 500 mm high, water temperature 24±1° C.) with a plexiglass platform 76 mm diameter painted white and submerged 15 mm below the surface of water (225 mm high) which is rendered opaque with the addition of dilute, white, non-toxic paint. During training, the platform is hidden in one quadrant 14 cm from the side wall. The mouse is gently placed into the water facing the wall at one of four randomly-chosen locations separated by 90 degrees. The latency to find the hidden platform within a 90 second criterion time is recorded by a blinded observer. On the first trial, mice failing to find the platform within 90 seconds are assisted to the platform. Animals are allowed to remain on the platform for 15 seconds on the first trial and 10 seconds on all subsequent trials. There is an inter-trial interval of 30 minutes, during which time the mice are towel-dried and placed under a heat lamp. A series of 16 training trials administered in blocks of 4 are typically conducted on days 7, 8, 9, and 10 post-surgery.

8.1.7 Data Analysis

Continuous variables compared across groups are examined using an analysis of variance (ANOVA) followed by Bonferroni correction (acute reflexes). Continuous variables subjected to repeated measurements over a period of time (beam walking, Morris water maze) are analyzed using a repeated measurements ANOVA followed by Tukey's pairwise comparison at each time point. A p value<0.05 is considered statistically significant.

8.2 Results 8.2.1 Chronic Neurological Recovery (Beam Walking)

FIG. 3 shows the results of the beam-walking experiment. Referring to FIG. 3, the number of contralateral rear footfaults was markedly increased in all injured groups when compared with sham-operated controls, reaching a maximum two days following injury. Mice treated with Compound 2a began to show some recovery of function after 3 days and were performing considerably better on this task 2–3 weeks post-injury. This is in contrast to saline-treated injured animals, which exhibited significant deficits for the duration of the experiment. The sham-operated group maintained a baseline number of footfaults over the entire testing period. A repeated measures ANOVA yielded a significant Group effect $[F(3,27)=67.654, p<0.0001]$, Day effect $[F(6,18)=97.657, p<0.0001]$ and Group X Day interaction $[F(18,162)=11.941, p<0.0001]$. Post-hoc analysis with Tukey's pairwise comparisons detected significant differences between sham-operated and saline-treated injured animals at days 1, 2, 3, 7, 14 and 21 ($p<0.001$). However, at 14 days following injury, mice treated with Compound 2a showed a significant improvement in performance of this task when compared with saline-treated injured animals ($p<0.05$). Similarly, a continued improvement in outcome when compared with saline-treated animals was seen at 21 days post-injury in animals treated with Compound 2a ($p<0.01$).

Referring to FIG. 4, Compound 2a shows an inverted U-shaped dose-response curve, with optimal effects at 1 mg/kg treatment.

8.2.2 Spatial Learing in the Watermaze

Figure 5:
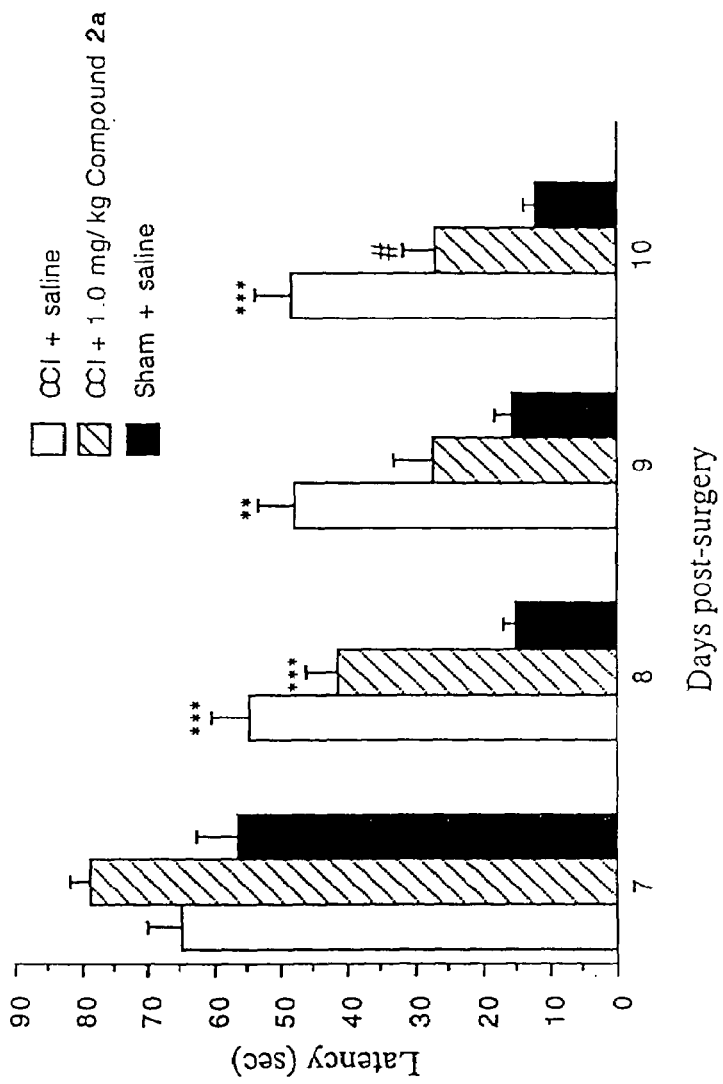

FIG. 5 shows the results of the place-learning watermaze experiment. Referring to FIG. 5, the effect of CCI on place-learning in the watermaze task was assessed by comparing the daily mean latency (±SEM) to goal location over the 4 trials for each group. A clear difference in learning ability emerged between sham-operated and saline-treated injured animals when trained at days 7–10 post-surgery, with sham animals locating the hidden goal platform on a consistently faster basis than their injured counterparts. A repeated measures ANOVA yielded a significant Group effect $[F(3,28)=15.636, p=0.0001]$, Day effect $[F(3,84)=62.723, p<0.0001]$ and Group X Day interaction $[F(9,84)=5.076, p<0.0001]$, averaged over the four days. Post-hoc analysis using Tukeyos pairwise comparison detected significant differences between sham animals and saline-treated injured controls on day 8 ($p<0.001$), day 9 ($p<0.01$) and day 10 ($p<0.001$) following injury. On day 8, injured animals given Compound 2a were also significantly different from sham-operated controls ($p<0.001$). However, after the third day of training (day 9), animals treated with Compound 2a were out-performing their saline-treated counterparts, and were no longer significantly different from sham-operated controls ($p>0.05$). On the last day of training, the drug-treated group showed significantly improved latencies to find the goal platform when compared with saline-treated injured mice ($p<0.01$).

Figure 6A:
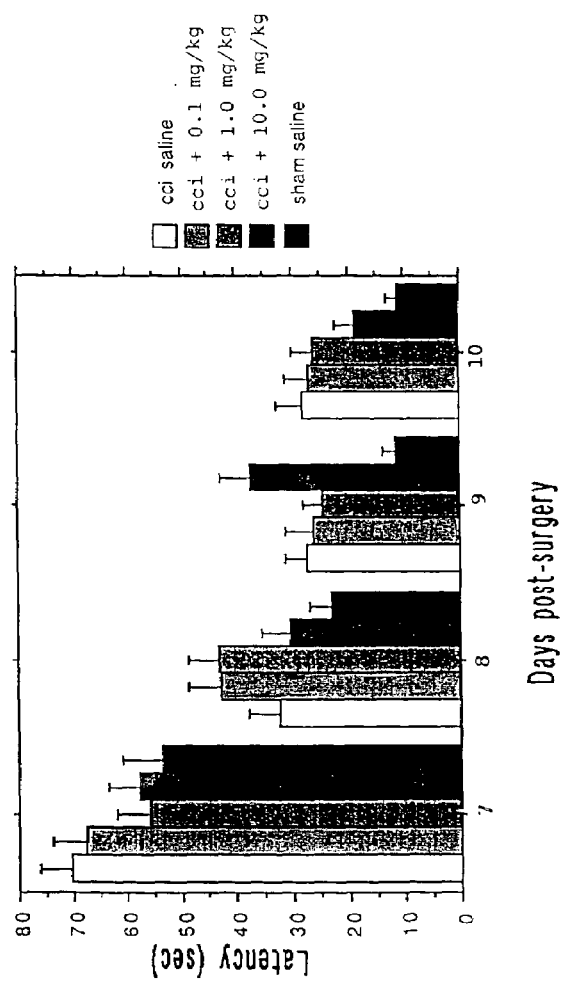
Figure 6B:
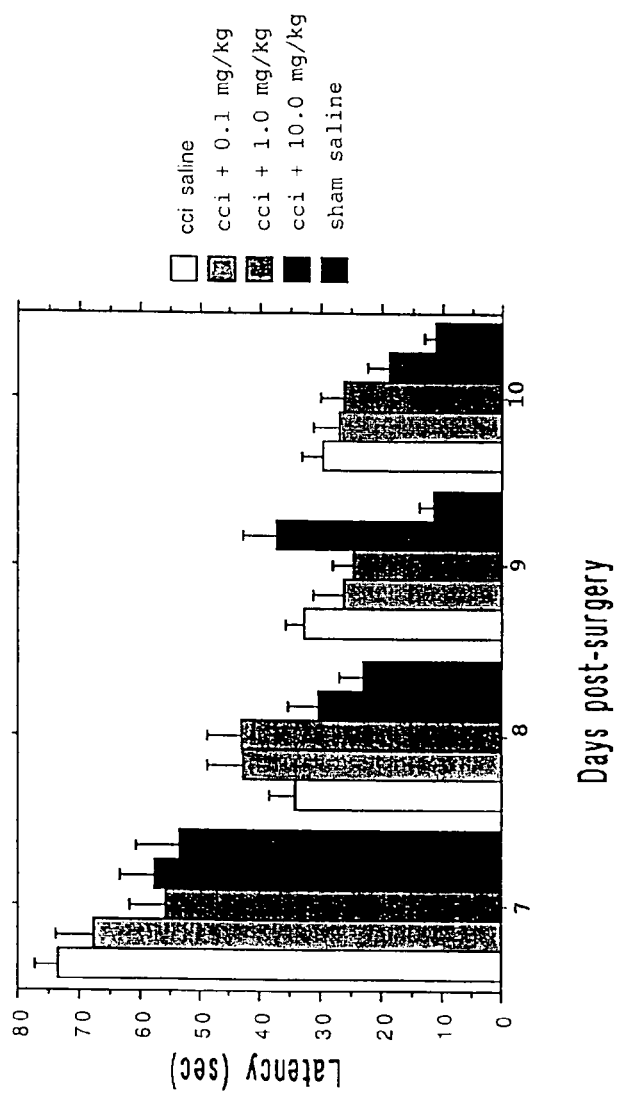

FIGS. 6A and 6B show the results of two dose-response experiments. Data presented in FIG. 6A was collected using an uninjured control sample size of n=6 and sample sizes of n=8 for each treatment group. Data presented in FIG. 6B was collected using an uninjured control sample size of n=12 and sample sizes of n=8 for each treatment group. At 10 days post-surgery, all treatment groups showed improved place-learning as compared with saline-treated controls (CCI+saline). By 10 days post-surgery, groups treated with 10 mg/kg Compound 2a exhibited the most improved learning.

8.2.3 Working Memory in the Watermaze

Figure 7:
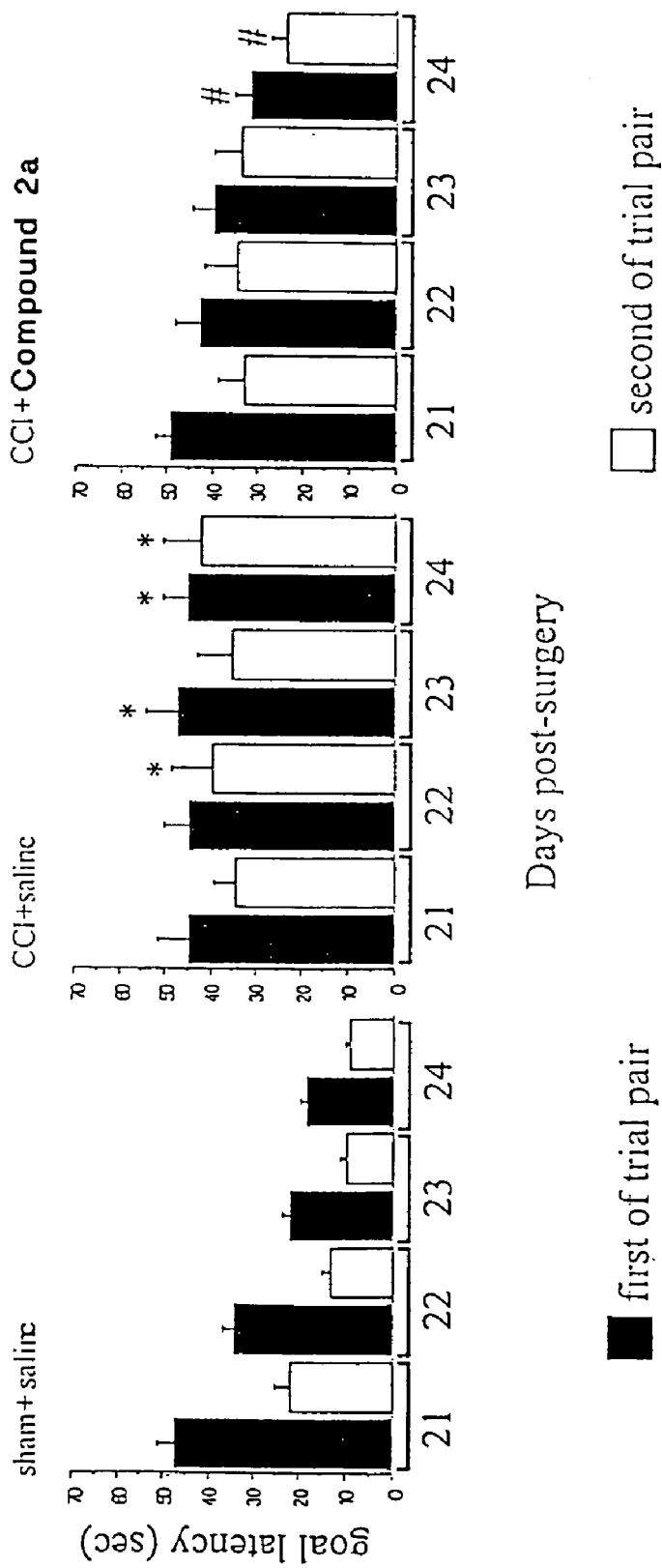
Figure 8:
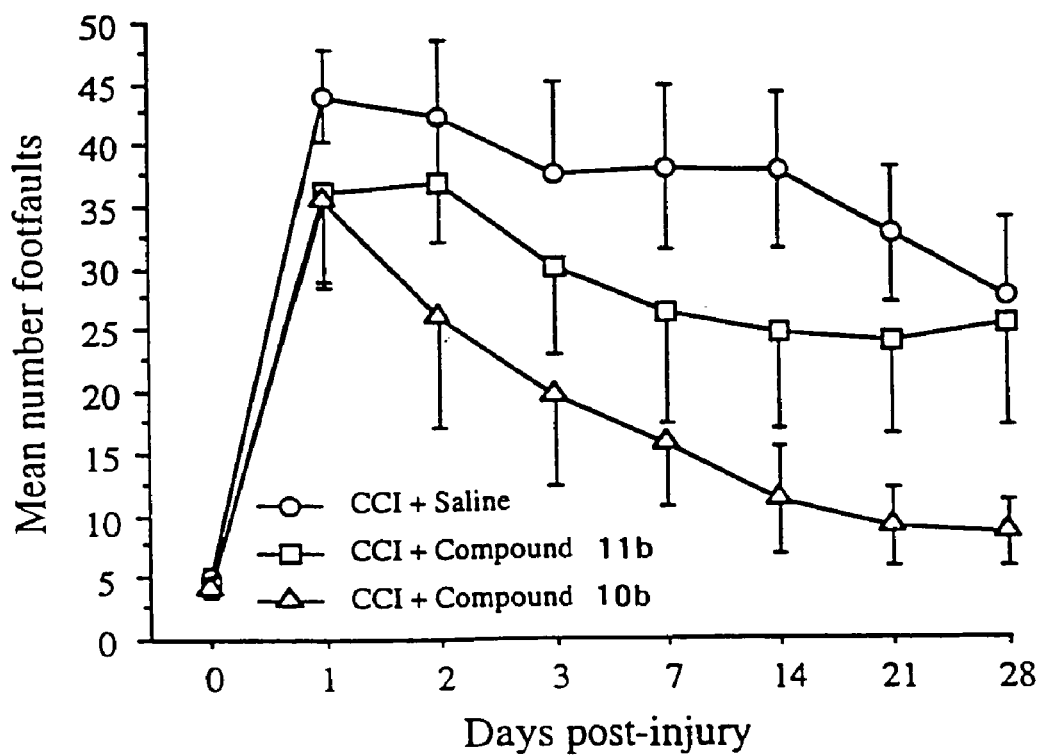
FIG. 8 shows the results of the beam-walking experiment for mice treated with saline, Compound 10b and Compound 11b following CCI injury. Despite the small group size, performance deficits in the beamwalking task were attenuated in animals treated with Compound 10b or 11b compared with those receiving only saline vehicle.

To determine the effect of CCI on working memory, the daily mean latency (±SEM) to find the goal platform on both trials was calculated for each group. A repeated measures ANOVA averaged over the four days for the first of the trial pair (filled bars in FIG. 7) yielded a significant Group effect $[F(2,20)=4.842, p=0.0193]$, indicating a difference in learning abilities between the three groups over this time period. A significant Day effect $[F(3,60)=13.742, p<0.0001]$ was also observed, indicating a significant decrease in goal latency on the first of the trial pairs. This suggests that some mice were able to retain spatial information over time better than others. This is demonstrated by the observed Group x day interaction $[F(6,60)=4.653, p=0.0006]$. Post-hoc analysis using Tukey's pairwise comparison test yielded significant differences between uninjured control (sham) animals and injured mice on days 23 and 24 ($p<0.05$) post surgery. However, the performance of injured mice treated with Compound 2a was significantly improved when compared with untreated injured animals on day 24 after trauma ($p<0.05$, Tukey's pairwise comparison), indicating significantly better reference memory function in drug-treated mice.

A repeated measures ANOVA averaged over the four days for the second of the trial pair (open bars in FIG. 7) yielded a significant Group effect $[F(2,20)=8.760, p=0.0019]$, indicating a difference in working memory between the three groups over this time period. Post-hoc analysis using Tukey's pairwise comparison test yielded significant differences between uninjured control (sham) animals and injured mice on days 22 and 24 ($p<0.05$) post surgery. However, the performance of injured mice treated with Compound 2a in this task was significantly improved when compared with untreated injured animals on day 24 after trauma ($p<0.05$, Tukey's pairwise comparison), indicating significantly better working memory function in drug-treated mice.

9. EXAMPLE

In Vivo Activity in Rats

This Example demonstrates the ability of certain exemplary compounds of the invention to treat neurotrauma in rats. The methods are generally applicable for demonstrating the in vivo activity of other compounds described herein. The protocols are generally those described in Faden, 1989, Brain Research 486:228–235 and McIntosh et al., 1989, Neuroscience 28(1):233–244.

9.1 Experimental Protocol 9.1.1 Animals

Male Sprague-Dawley rats (375–425 g) were obtained from Harlan (Frederick, Md.) and housed for at least 1 week prior to any procedures. The animals were maintained at a constant temperature (22±2° C.) and a 12 hr light/dark cycle, with lights on at 6 am and all neurological scoring performed during the light cycle. Food and water were available ad libitum.

9.1.2 Fluid-Percussion Induced Traumatic Brain Injury (TBI)

Rats were anesthetized with sodium pentobarbital (70 mg/kg i.p.), intubated, and implanted with femoral venous and arterial catheters. Brain temperature was assessed indirectly through a thermister in the temporalis muscle. Body temperature was maintained through a feedback-controlled heating blanket. Blood pressure was continuously monitored, and arterial blood gases analyzed periodically. After the animal was placed in a stereotaxic frame, the scalp and temporal muscle were reflected, and a small craniotomy (5 mm) located midway between the lambda and bregma sutures over the left parietal cortex allowed insertion of a Leur-Loc that is cemented in place. The fluid-percussion head injury device, manufactured by the Medical College of Virginia, consists of a plexiglass cylindrical reservoir filled with isotonic saline; one end includes a transducer that is mounted and connected to a 5 mm tube that attaches through a male Leur-Loc fitting to the female Leur-Loc cemented at the time of surgery. A pendulum strikes a piston at the opposite end of the device, producing a pressure pulse of approximately 22 msec duration, leading to deformation of underlying brain. The degree of injury is related to the pressure pulse, expressed in atmospheres (atm): 2.6 atm in our laboratory produces a moderate injury with regard to neurological and histological deficit. Sham (control) animals undergo anesthesia and surgery without fluid percussion brain injury.

9.1.3 Neurological Scoring

Standardized motor scoring was performed at 1, 7 and 14 days after TBI, by individuals unaware of treatment. Motor function was evaluated utilizing 3 separate tests, each of which is scored via an ordinal scale ranging from 0=severely impaired to 5=normal function. Tests include ability to maintain position on an inclined plane in the vertical and two horizontal positions for 5 sec; forelimb flexion (suspension by the tail) and forced lateral pulsion. Each of seven individual scores (vertical angle, right and left horizontal angle, right and left forelimb flexion, right and left lateral pulsion) were added to yield a composite neurological score ranging from 0 to 35. This scoring method shows high interrater reliability and is very sensitive to pharmacological manipulations (see, Faden et al., 1989, Science 244: 798–800).

9.1.4 Automatic and Analeptic Assessment

Additional groups of uninjured rats were tested for autonomic and analeptic responses immediately prior to and up to 60 min. following drug administration. For the analeptic study, rats were first anesthetized with 40 mg/kg i.p. sodium pentabarbitone and placed onto an unheated pad on the laboratory bechtop at room temperature (22±2° C.). A thermister probe was placed in the rectum to measure core body temperature. After a 10 min. period, rats were administered vehicle or drug as described below via the tail vein. Time to recovery of the righting reflex was subsequently determined while temperature was recorded at 5 min. intervals for all animals.

To assess autonomic responses to the novel TRH analogues, a separate group of rats were anesthetized with 4% isoflurane (1.5 L/min). Catheters were then placed into the right artoid artery and right jugular vein and exteriorized at the back of the neck. Rats were separated one per cage and allowed to recover from anesthesia. The exteriorized catheters were suspended above the rat to prevent biting. Mean arteriolar blood pressure (MAP) was continuously recorded via a transducer connected directly to the arterial catheter for the duration of the study. At 1 h following catheter placement, rats were administered vehicle or drug via the catheter in the jugular vein as described below.

9.1.5 Administration of 1a, 2a, and 4a

Rats were injected via the femoral vein catheter with a single bolus dose (1 mg/kg) of one of the following compounds 30 minutes following fluid percussion injury: normal saline (injured controls; n=5 or n=11), Compound 1a (n=5), Compound 2a (n=12) or Compound 4a (n=8). The value for n indicates the number of animals in the treatment group. The investigator was blinded to drug treatment both at the time of surgery and for neurological scoring.

9.1.6 Administration of 14c

Rats were injected via the femoral vein catheter with a single bolus dose (1 mg/kg) of one of the following compounds 30 minutes following fluid percussion injury: normal saline (injured controls; n=14), Compound YM-14673 (n=17) or Compound 14c (n=13). The value for n indicates the number of animals in the treatment group. The investigator was blinded to drug treatment both at the time of surgery and for neurological scoring. For autonomic and analytic studies, rats were given either normal saline (n=6), compound YM-14673 (n=6) or Compound 14c (n=6) at the times indicated above.

9.1.7 Data Analysis

Continuous variables compared across groups were examined using an analysis of variance (ANOVA) followed by Bonferroni correction (rightin reflex). Continuous variables subjected to repeated measurements over a period of time (cardiovascular and core temperature measurements) were analyzed using a repeated measurements ANOVA followed by Tukey's pairwise comparison at each time point. Ordinal measurements (composite neurological scores) were evaluated using the non-parametric Kruskal-Wallis ANOVA with individual, non-parametric Mann-Whitney U-tests. Survival differences were compared using the Chi-Square test. A p value<0.05 was considered statistically significant.

9.2 Results 9.2.1 Neurological Scoring of Compound 1a, 2a and 4a

Figure 1:
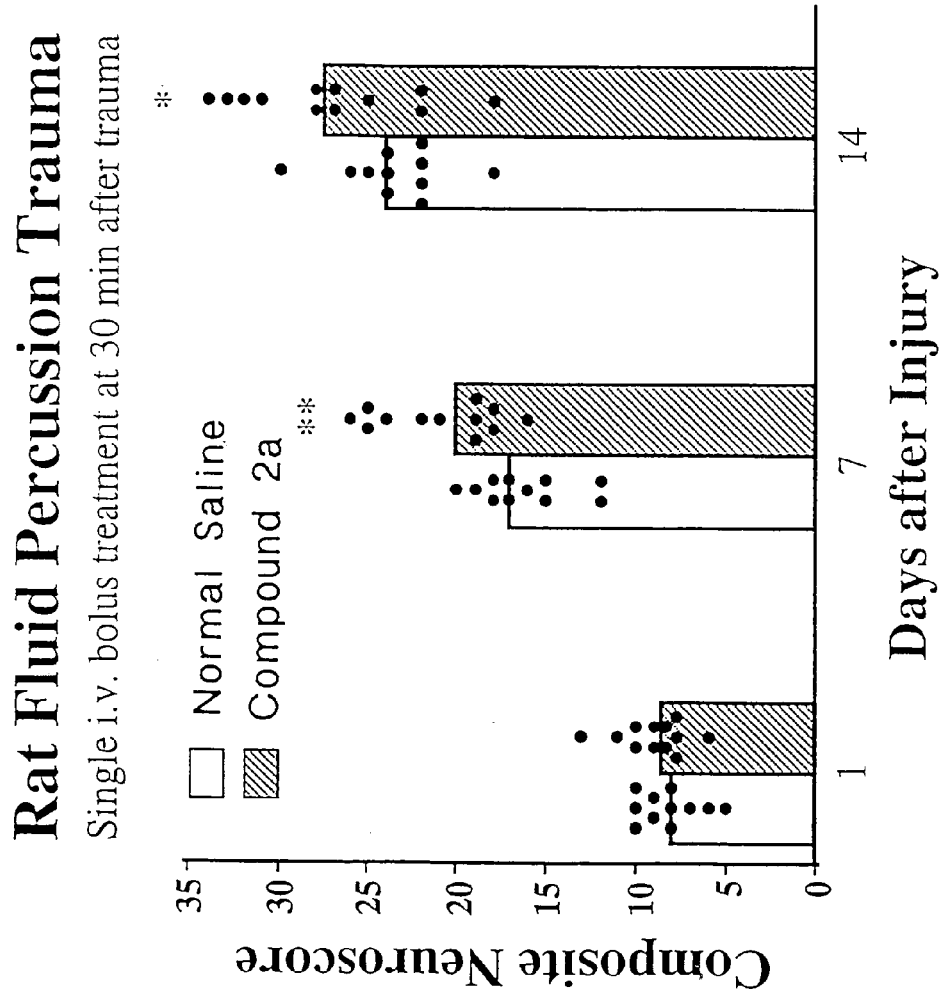
Figure 2:
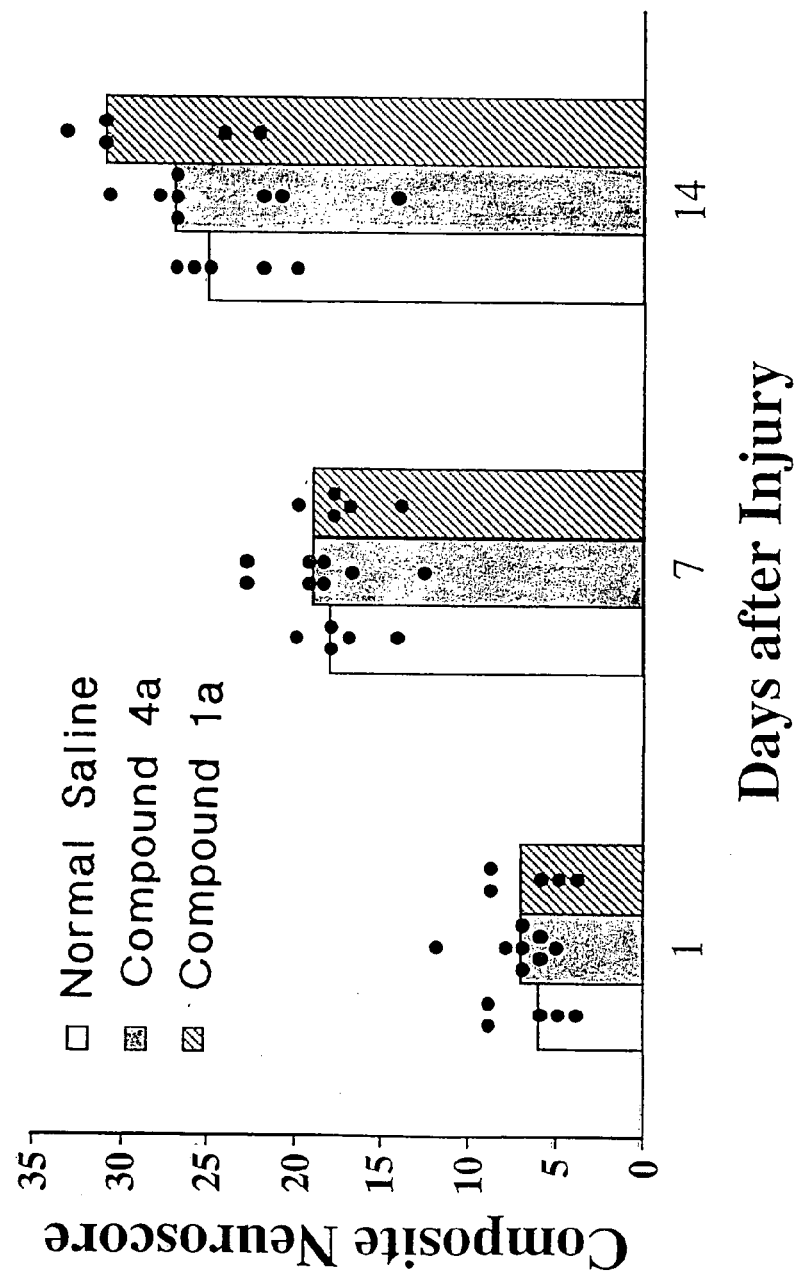
Figure 3:
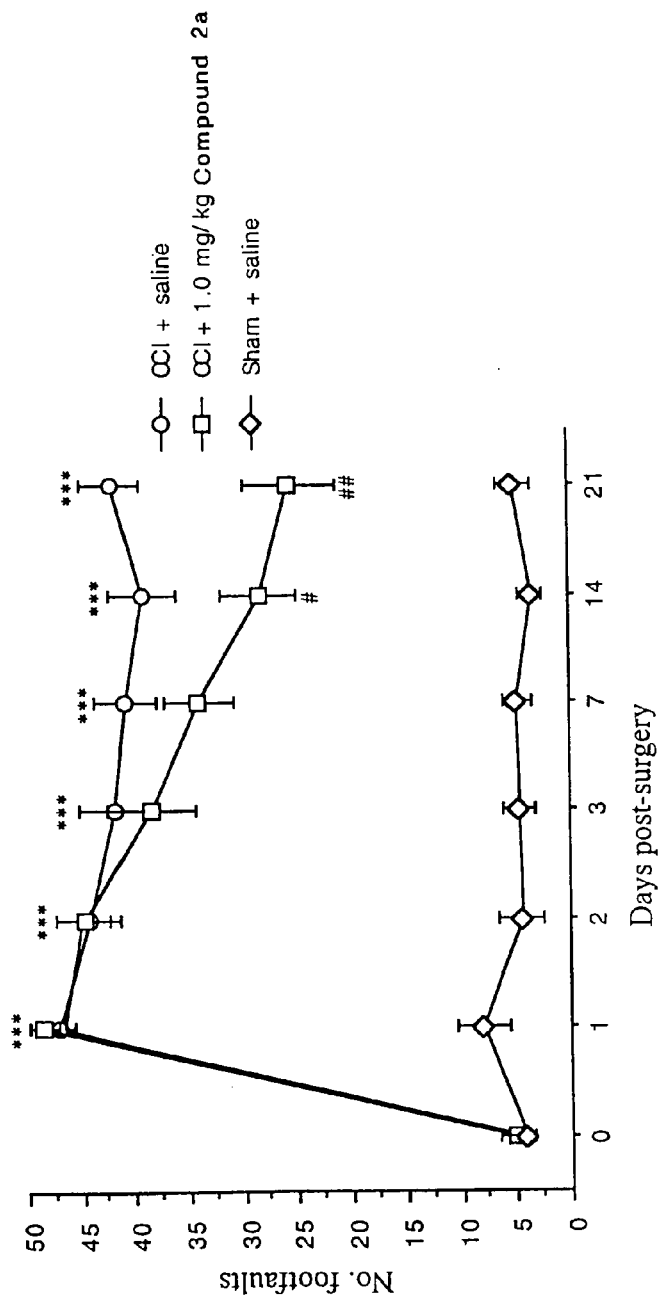
Figure 4:
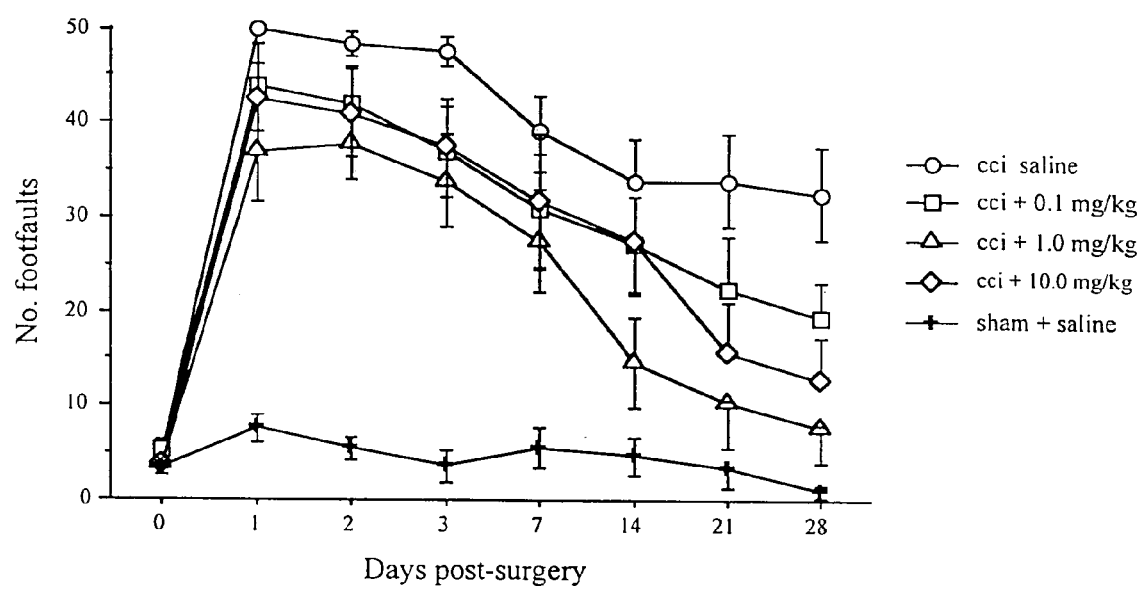
FIG. 4 shows the results of the dose-response beam-walking experiment.

Fluid percussion injury induces significant deficits of motor function in untreated rats (i.e., rats receiving normal saline) following injury, although a gradual recovery of function occurs over an extended time period of 2–3 weeks. In these studies, all animals exhibited a low neuroscore when tested 1 day after injury, and there was no appreciable difference between treatments (FIGS. 1 & 2). However, at seven and 14 days post injury, significant differences in outcome were found between groups treated with Compound 1a (Kruskal-Wallis ANOVA, p=0.2292 and p=0.2846 respectively), Compound 2a (Kruskal-Wallis ANOVA, p=0.0042 and p=0.0140, respectively) and Compound 4a (Kruskal-Wallis ANOVA, p=0.2292 and p=0.2846 respectively). At seven days, further analysis using individual Mann-Whitney U tests revealed a highly significant improvement of function in rats which received either Compound 1a (p=0.0758), Compound 2a (p=0.0026) or Compound 4a (p=0.2723) when compared with saline-treated injured controls. Similarly, after 14 days, neurological outcome continued to improve in all animals, but was significantly improved in rats treated with Compounds 1a (p=0.2101), 2a (p=0.0423) and 4a (p=0.3798) when compared with saline-treated rats.

9.2.2 Neurological Scoring of Compound 14c

Figure 9:
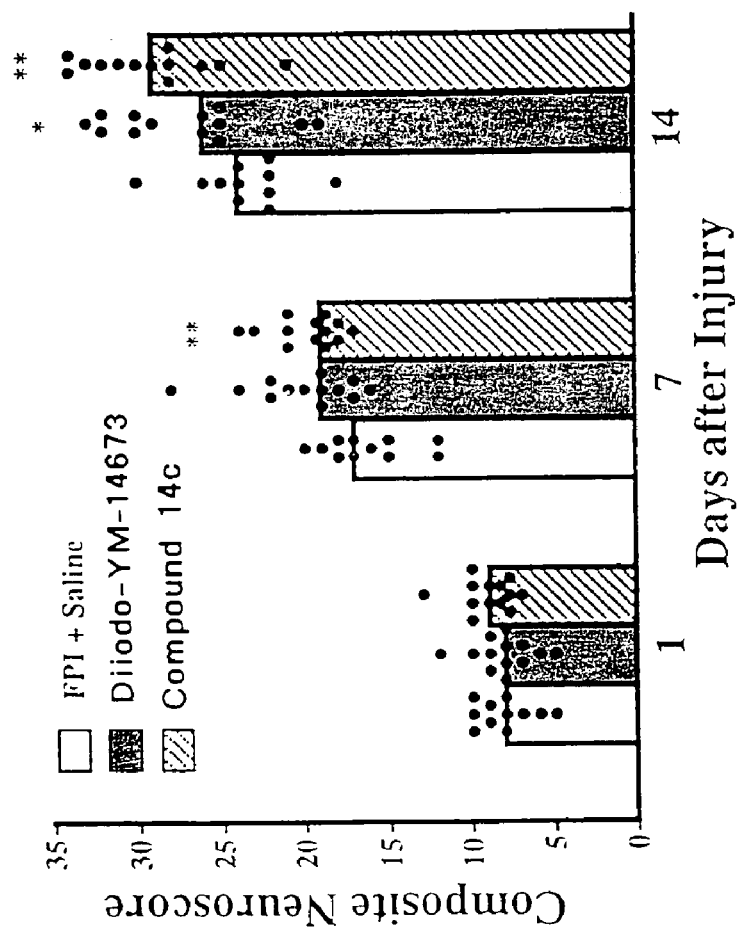

Fluid percussion injury induces significant deficits of motor function in untreated rats (i.e., rats receiving normal saline) following injury, although a gradual recovery of function occurs over an extended time period of 2–3 weeks. In these studies, all animals exhibited a low neuroscore when tested 1 day after injury, and there was no appreciable difference between treatments (FIG. 9). However, at 7 and 14 days post injury, a significant difference in outcome were found between groups (Kruskal-Wallis ANOVA, p<0.0042 and p<0.014 respectively). At seven days, further analysis using individual Mann-Whitneys revealed a highly significant improvement of function in rats which received YM-14673 (p<0.0065). After 14 days, neurological outcome continued to improve in all animals, but was significantly improved in rats treated with YM-14673 (p<0.0239) or Compound 14c (p=0.0021).

9.2.3 Mortality in 1a, 2a, and 4a Experiments

Fluid percussion injury of a moderate level is typically associated with a mortality rate of approximately 25% in untreated animals. In the study of compounds 1a, 2a, and 4a, 3 out of 14 (21.4%) (FIG. 1) and 3 out of 8 (37.5%) (FIG. 2) rats given normal saline died before the end of the study. In comparison, mortality rates of 2 out of 7 (28.6%), 4 out of 16 (25%) and 0 out of 8 (0%) were recorded for animals treated with Compounds 1a, 2a and 4a respectively. In the study of compound 14C, there were no differences in mortality across the groups.

9.2.4 Autonomic and Analeptic Studies

Figure 10:
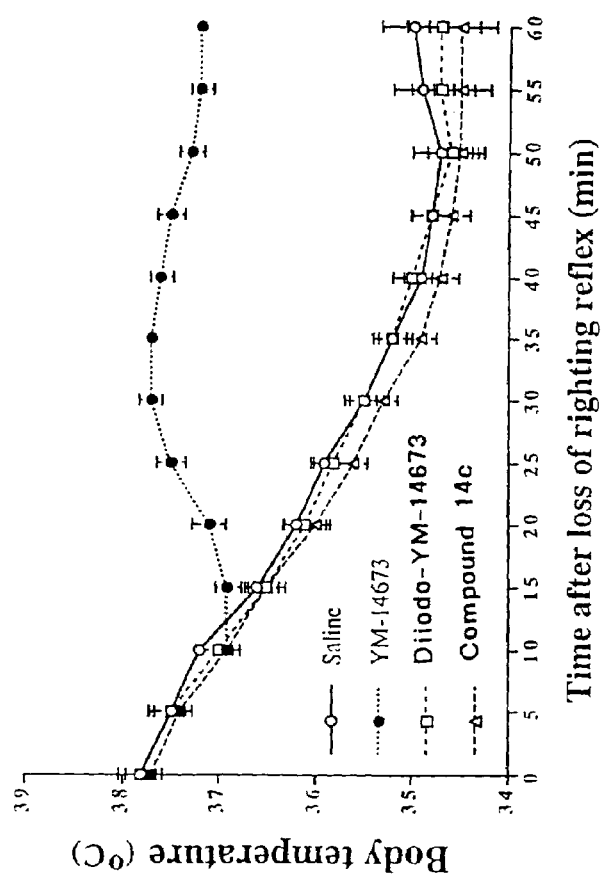

Core body temperature was similar for all treatment groups immediately following anesthesia. However, over the following 60 min., body temperature dropped by almost 3° C. for rats treated with normal saline and Compound 14c (FIG. 10). In contrast, animals treated with the positive control YM-14673 maintained a core temperature between 37–38° C. A repeated measures ANOVA yielded a significant Group effect [$F(3,20)=23.163$, $p<0.0001$], Time effect [$F(12,240)=279.967$, $p<0.0001$] and Group X Time interaction [$F(36,240)=35.989$, $p<0.0001$]. Post-hoc analysis with Tukey's pairwise comparison detected significant differences between YM-14673-treated rats and all other groups between time points 20–60 min. following loss of righting reflex ($p<0.001$).

Figure 11:
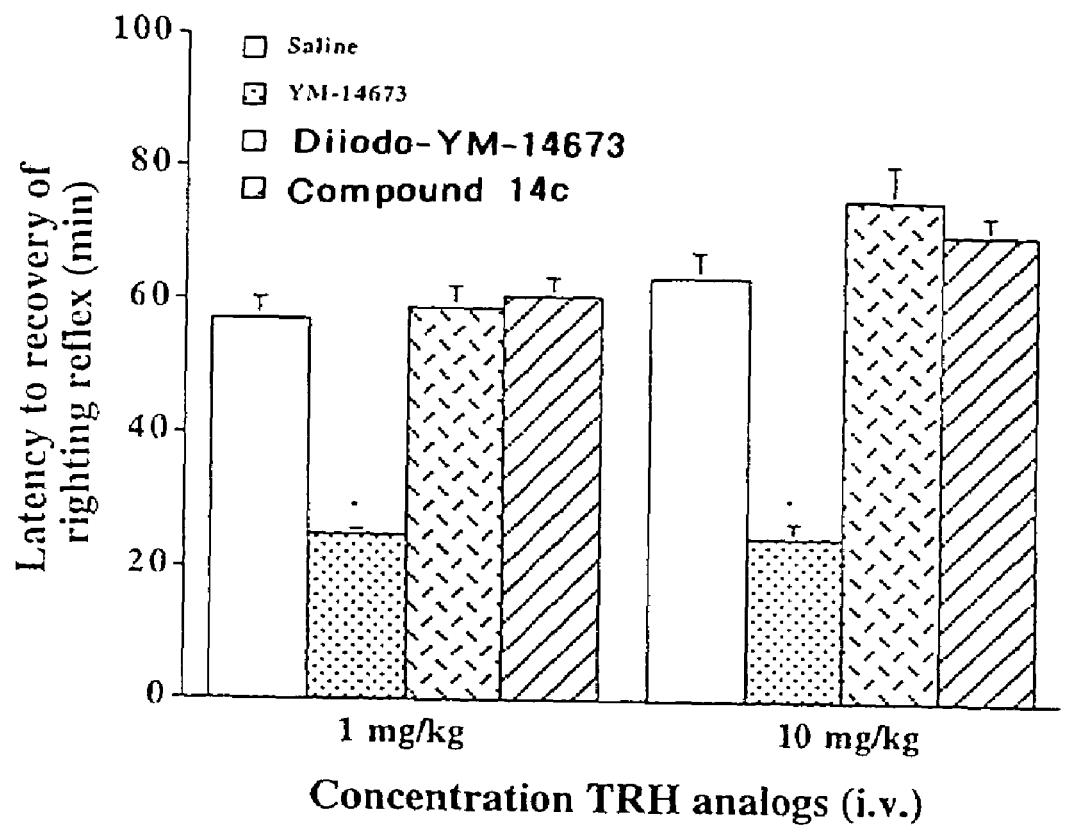
Figure 12:
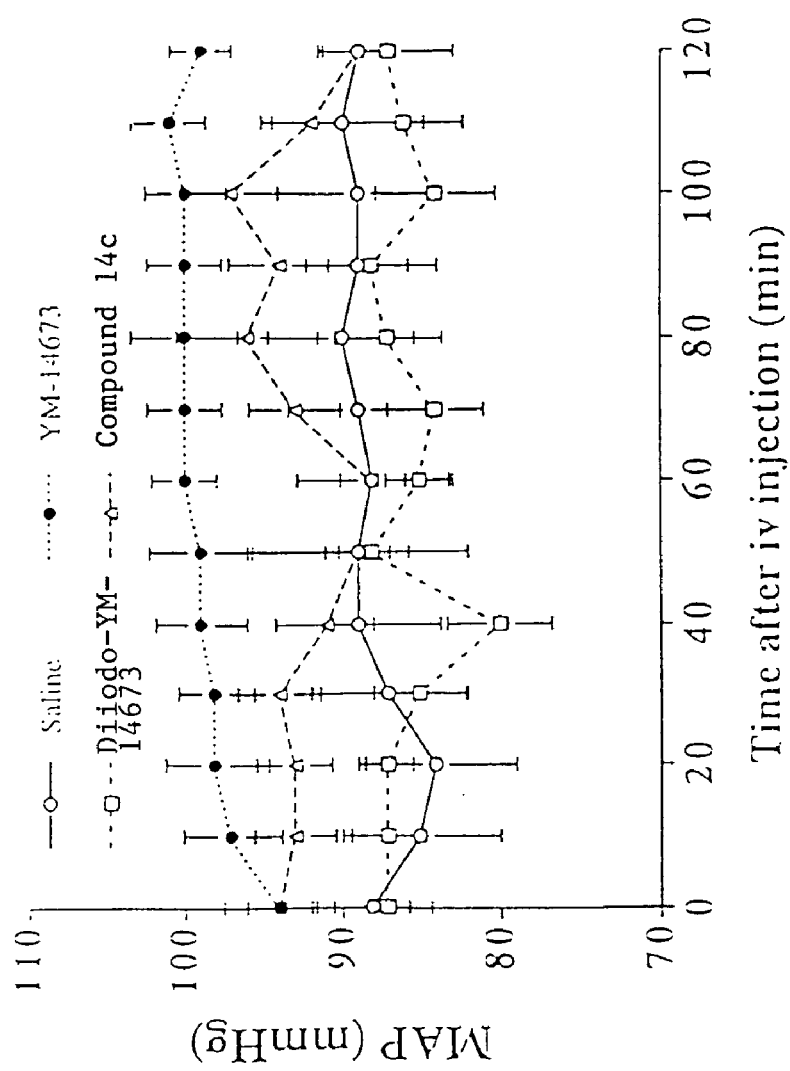
Figure 13:
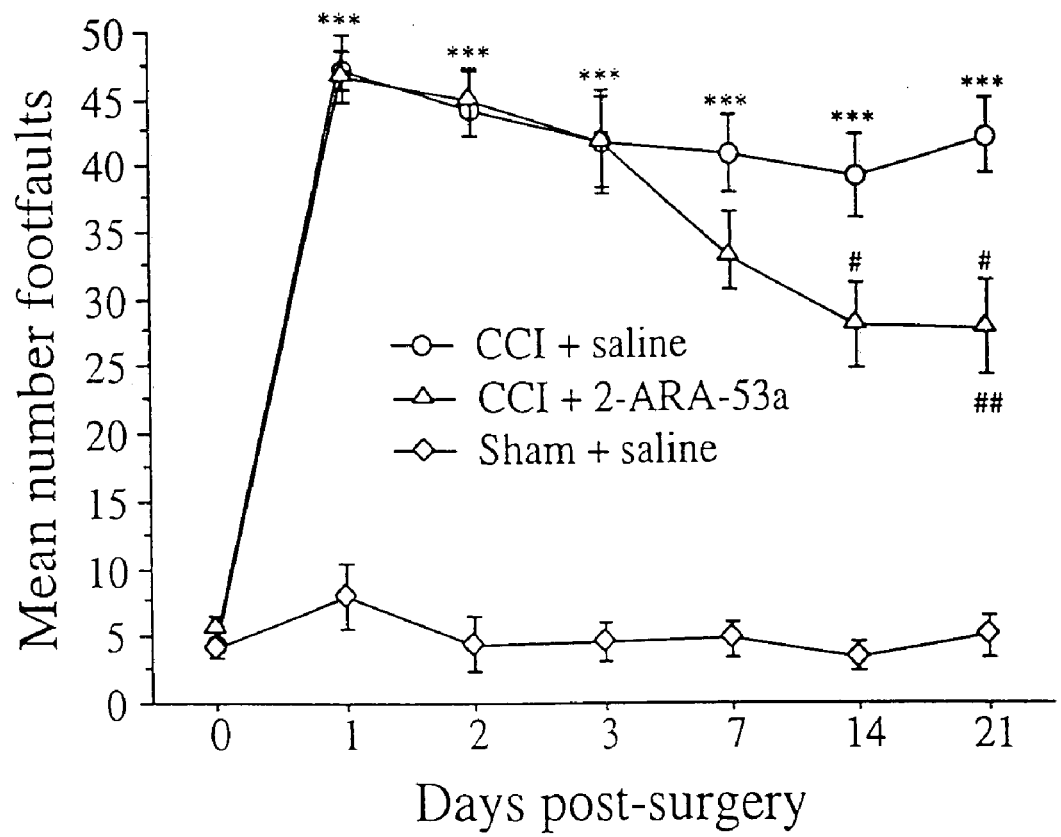

Recovery of righting reflex did not differ significantly between saline or Compound 14c treated groups, although latency to reflex recovery was significantly attenuated in rats administered YM-14673 (FIG. 11) ($p<0.0001$ Bonferroni post-hoc test), thus demonstrating the analeptic effects of YM-14673, and lack thereof in animals treated with vehicle or Compound 14c. MAP did not differ significantly between rats treated with vehicle or Compound 14c (FIG. 12). However, animals administered YM-14673 maintained a significantly higher MAP over the duration of testing as compared with all other groups. A repeated measures ANOVA yielded a significant Group effect [$F(3,21)=3.728$, $p<0.0271$], and Group X Time interaction [$F(36,252)=1.551$, $p<0.0289$]. Post-hoc analysis with Tukey's pairwise comparison detected significant differences between YM-14673-treated rats and all other groups at 60 and 120 min. after injection ($p<0.05$) and between YM-14673 and Compound 14c at 30, 40, 70, 90, 100, and 110 minutes after injection ($p<0.05$).

10. EXAMPLE

Formulations

The following examples provide exemplary, not limiting, formulations for administering the compounds of the invention to mammalian, especially human, patients. Any of the compounds described herein, or pharmaceutical salts or hydrates thereof, may be formulated as provided in the following examples.

10.1 Tablet Formulation

Tablets each containing 60 mg of active ingredient are made up as follows:

| | |
|---|---|
| Active C | 60 mg |
| Starch | 45 mg |
| Microcrystalline Cellulose | 45 mg |
| Sodium carboxymethyl starch | 4.5 mg |
| Talc | 1 mg |
| Polyvinylpyrrolidone (10% in water) | 4 mg |
| Magnesium Stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50°–60° C. and passed through a No. 18 mesh U.S. sieve. The sodium carboxymethyl starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed by wet granulation followed by compression.

10.2 Gelatin Capsules

Hard gelatin capsules are prepared using the following ingredients:

| | |
|---|---|
| Active C | 250 mg/capsule |
| Starch dried | 200 mg/capsule |
| Magnesium Stearate | 10 mg/capsule |

The above ingredients are mixed and filled into hard gelatin capsules in 460 mg quantities.

10.3 Aerosol Solution

An aerosol solution is prepared containing the following components:

| | |
|---|---|
| Active C | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

10.4 Suppositories

Suppositories each containing 225 mg of active ingredient are made as follows:

| | |
|---|---|
| Active C | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

10.5 Suspensions

Suspensions each containing 50 mg of medicament per 5 mL dose are made as follows:

| | |
|---|---|
| Active C | 50 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

All cited references are hereby incorporated in their entireties by reference herein.

The invention claimed is:

1. A method of providing neuroprotection to a subject resulting from either brain or spinal cord trauma or stroke comprising administering to a subject in need of such treatment an effective amount of a compound having the formula:

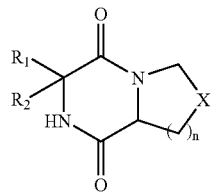

or a pharmaceutically acceptable salt or hydrate thereof, wherein:

n is an integer from 0 to 3;

X is selected from the group consisting of —S—, —O—, —NR— and CH$_2$—;

R$_1$ and R$_2$ are each independently selected from the group consisting of —H, —OR, —SR, —NRR, —NO$_2$, CN, —C(O)OR, —C(O)NRR, —C(NR)NRR, trihalomethyl, halogen, (C$_1$–C$_6$) alkyl, substituted (C$_1$–C$_6$) alkyl, (C$_2$–C$_6$) alkenyl, substituted (C$_2$–C$_6$) alkenyl, (C$_2$–C$_6$) alkynyl, substituted (C$_2$–C$_6$) alkynyl, (C$_5$–C$_{20}$) aryl, substituted (C$_5$–C$_{20}$) aryl, 5–20 membered heteroaryl, substituted 5–20 membered heteroaryl, (C$_6$–C$_{26}$) alkaryl, substituted (C$_6$–C$_{26}$) alkaryl, 6–26 membered alk-heteroaryl and substituted 6–26 membered alk-heteroaryl, or R$_1$ and R$_2$ taken together are —CH$_2$—(CH$_2$)$_m$—CH$_2$—, where m is an integer from 0 to 6;

each alkyl, alkenyl, alkynyl, aryl, alkaryl, heteroaryl or alk-heteroaryl substitutent is independently selected from the group consisting of —OR, —SR, —NRR, —CN, —NO$_2$, —C(O)OR, —C(O)NRR, —C(S)NRR, —C(NR)NRR, halogen and trihalomethyl; and each is R independently selected from the group consisting of —H, (C$_1$–C$_6$) alkyl, (C$_2$–C$_6$)alkenyl, (C$_2$–C$_6$) alkynyl, (C$_5$–C$_{20}$), aryl, 5–20 membered heteroaryl, (C$_6$–C$_{26}$) alkaryl and 6–26 membered alk-heteroaryl.

2. The method of claim 1, wherein both carbons at positions 3 and 6 of the parent bicyclic 2,5-diketopiperazine ring are in the S configuration.

3. The method of claim 1, wherein X is —CH$_2$—.

4. The method of claim 1, wherein is 1.

5. The method of claim 1, wherein said compound is selected from a group consisting of:

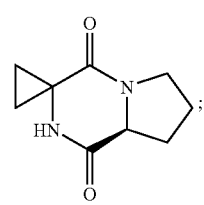

(1a)

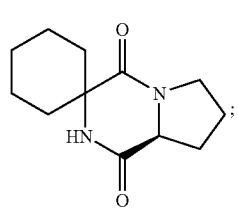

(2a)

-continued
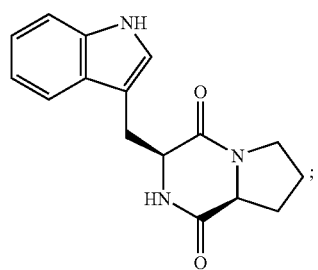
(3a)
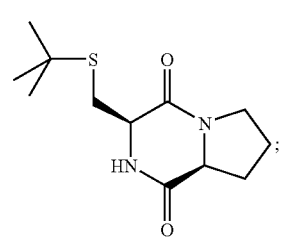
(4a)
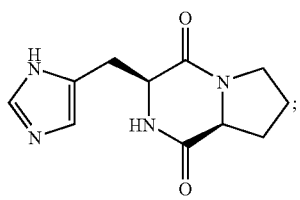
(5a)
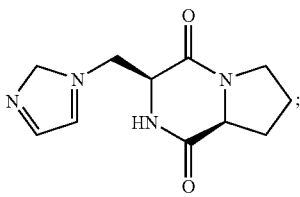
(6a)
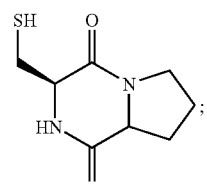
(7a)
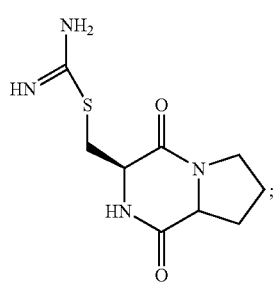
(8a)
-continued
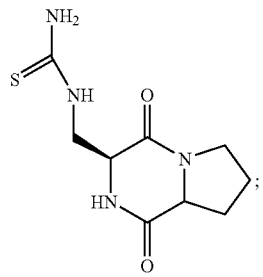
(9a)
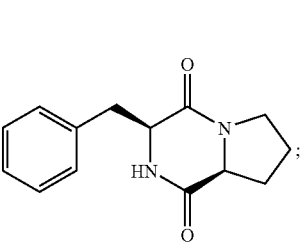
(10a)
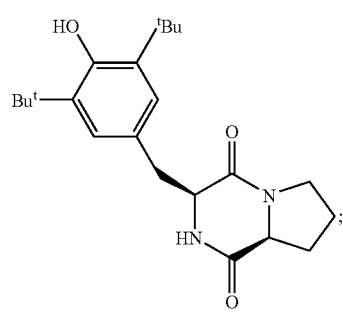
(11a)
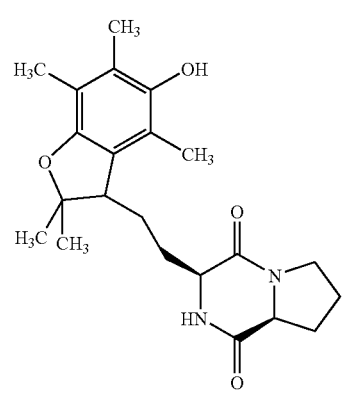
(12a)
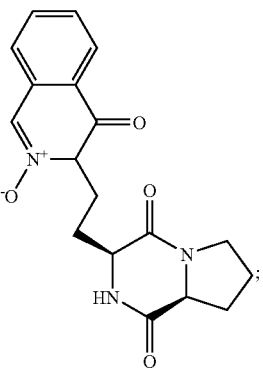
(13a)

(14a)

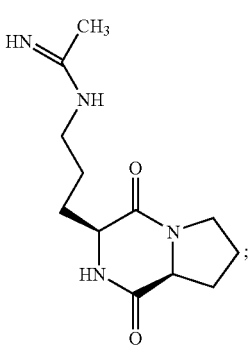

(15a)

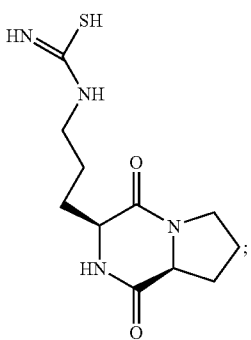

(16a)

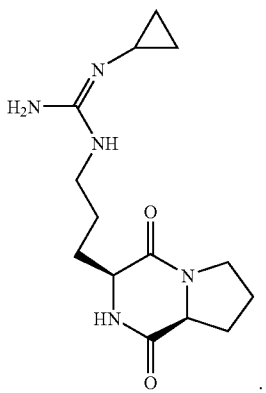

6. The method of claim 1 in which said compound has the following structure:

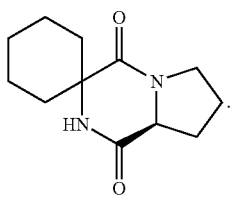

7. A method of enhancing cognitive function, said method comprising the step of administering to a subject an effective compound having the formula:

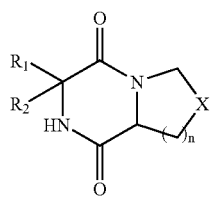

or a pharmaceutically acceptable salt or hydrate thereof, wherein:

n is an integer from 0 to 3;

X is selected from the group consisting of —S—, —O—, —NR— and —CH$_2$—;

R$_1$ and R$_2$ are each independently selected from the group consisting of —H, —OR, —SR, —NRR, —NO$_2$, —CN, —C(O)OR, —C(O)NRR, —C(NR)NRR, trihalomethyl, halogen, (C$_1$–C$_6$) alkyl, substituted (C$_1$–C$_6$) alkyl, (C$_2$–C$_6$) alkenyl, substituted (C$_2$–C$_6$) alkenyl, (C$_2$–C$_6$) alkynyl, substituted (C$_2$–C$_6$) alkynyl, (C$_5$–C$_{20}$) aryl, substituted (C$_5$–C$_{20}$) aryl, 5–20 membered heteroaryl, substituted 5–20 membered heteroaryl, (C$_6$–C$_{26}$) alkaryl, substituted (C$_6$–C$_{26}$) alkaryl, 6–26 membered alk-heteroaryl and substituted 6–26 membered alk-heteroaryl, or R$_1$ and R$_2$ taken together are —CH$_2$—(CH$_2$)$_m$—CH$_2$—, where m is an integer from 0 to 6;

each alkyl, alkenyl, alkynyl, aryl, alkaryl, heteroaryl or alk-heteroaryl subsistent is independently selected from the group consisting of —OR, —SR, —NRR, —CN, —NO$_2$, —C(O)OR, —C(O)NRR, —C(S)NRR, —C(NR)NRR, halogen and trihalomethyl; and each R is independently selected from the group consisting of —H, (C$_1$–C$_6$) alkyl, (C$_2$–C$_6$) alkenyl, (C$_2$–C$_6$) alkynyl, (C$_5$–C$_{20}$) aryl, 5–20 membered heteroaryl, (C$_6$–C$_{26}$) alkaryl and 6–26 membered alk-heteroaryl.

8. The method of claim 7, wherein the cognitive function is memory.

9. The method of claim 7, wherein both carbons at positions 3 and 6 of the parent bicyclic 2,5-diketopiperazine ring are in the S configuration.

10. The method of claim 7, wherein X is —CH$_2$—.

11. The method of claim 7, wherein n is 1.

12. The method of claim 7, wherein said compound is selected from the group consisting of:

(1a)

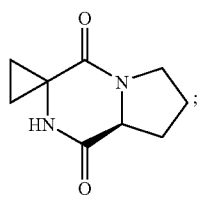

(2a)

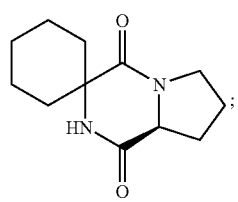

-continued
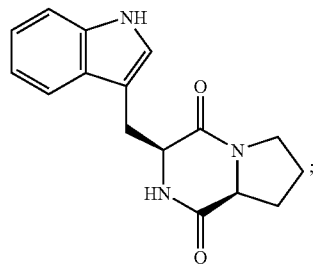
(3a)
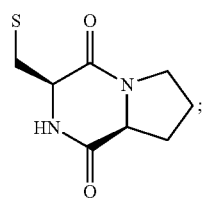
(4a)
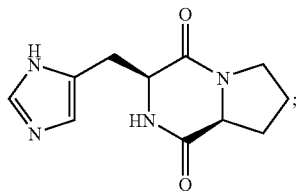
(5a)
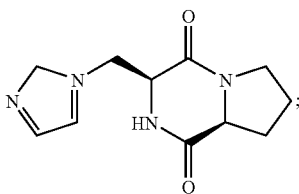
(6a)
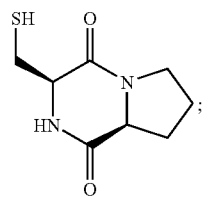
(7a)
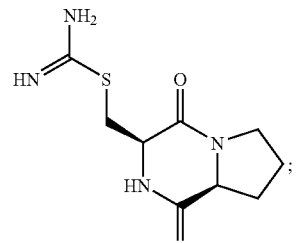
(8a)
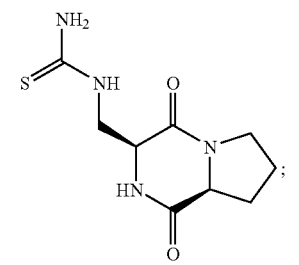
(9a)
-continued
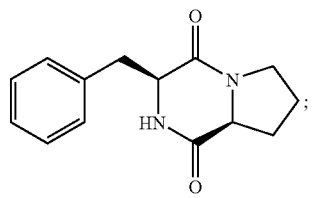
(10a)
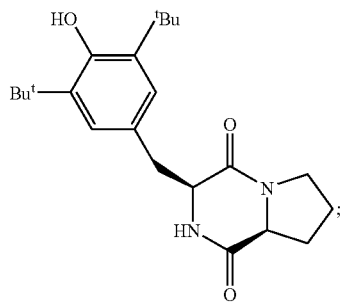
(11a)
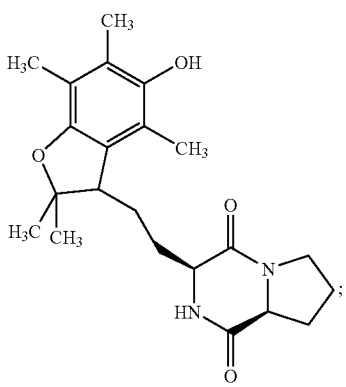
(12a)
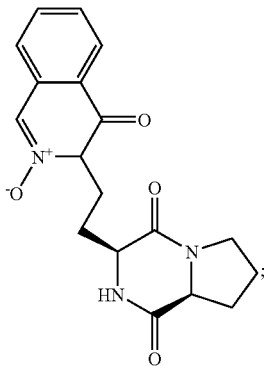
(13a)
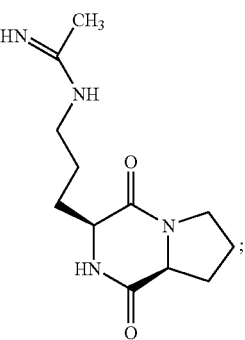
(14a)

-continued (15a)
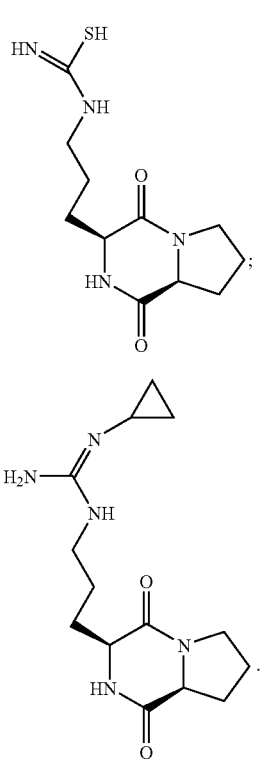

(16a)

13. The method of claim 7 in which said compound has the following structure:

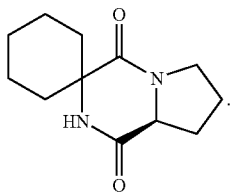

14. The method of claim 7, wherein said compound is administered following acute or chronic brain injury.

15. The method of claim 1, wherein $R_1$ is H.

16. The method of claim 12, wherein n is an integer from 1 to 3;

X is —S—, —O—, —NH— or —$CH_2$—;

$R_2$ is —$CH_2$—$R_5$, —$CH_2$—$R_5$ or —$CH_2$—$CH_2$—$CH_2$—$R_5$;

$R_5$ is phenyl, imidazolyl other than imidazol-2-yl, indolyl other than indol-3-yl, —$SR_6$, —$OR_6$ or —$NHR_6$; and $R_6$ is —H, ($C_1$–$C_6$) alkyl, ($C_2$–$C_6$) alkenyl, ($C_2$–$C_6$) alkynyl, —C(NH)$NH_2$ or —C(S)$NH_2$.

17. The method of claim 15, wherein n is an integer from 1 to 3;

X is —S—, —O—, —NH— or —$CH_2$—;

$R_2$ is —H, ($C_1$–$C_6$) alkyl, ($C_2$–$C_6$) alkenyl, ($C_2$–$C_6$) alkynyl or —($CH_2$)$_g$—$CH_2$—$R_7$;

g is an integer from 0 to 5;

$R_7$ is —$OR_8$, —$SR_8$, —$NR_8R_8$, —CH($OR_8$)—$CH_3$, —C(O)$R_8$, —C(O)$OR_8$, —C(O)$NR_8R_8$, —S—C(NH) $NH_2$, —NH—C(NH)$NH_2$, —NH—C(S)$NH_2$, phenyl, hydroxyphenyl imidazolyl, indolyl; and $R_8$ is —H, ($C_1$–$C_6$) alkyl, ($C_2$–$C_6$) alkenyl, ($C_2$–$C_6$) alkynyl.

18. The method of claim 7, wherein n is an integer from 1 to 3;

X is —S—, —O—, —NH— or —$CH_2$—; and $R_1$ and $R_2$ taken together are —$CH_2$—($CH_2$)$_b$— where b is an integer from 0 to 6.

19. The method of claim 7, wherein $R_1$ is H.

20. The method of claim 19, wherein n is an integer from 1 to 3;

X is —S—, —O—, —NH— or —$CH_2$—;

$R_2$ is —$CH_2$—$R_5$, —$CH_2$—$CH_2$—$R_5$ or —$CH_2$—$CH_2$—$CH_2$—$R_5$;

$R_5$ is phenyl, imidazolyl other than imidazol-2-yl, indolyl other than indol-3-yl, —$SR_6$, —$OR_6$ or —$NHR_6$; and $R_6$ is —H, ($C_1$–$C_6$) alkyl, ($C_2$–$C_6$) alkynyl or —($CH_2$)$_g$—$CH_2$—$R_7$.

21. The method of claim 19, wherein n is an integer from 1 to 3;

X is —S—, —O—, —NH— or —$CH_2$—;

$R_2$ is —H, ($C_1$–$C_6$) alkyl, ($C_2$–$C_6$) alkenyl, ($C_2$–$C_6$) alkynyl or —($CH_2$)$_g$—$CH_2$—$R_7$;

g is an integer from 0 to 5;

$R_7$ is —$OR_8$, $SR_8$, —$NR_8$, —$NR_8R_8$, —CH($OR_8$)—$CH_3$, —C(O)$R_8$, —C(O)$OR_8$, —C(O)$NR_8R_8$, —S—C(NH) $NH_2$, —NH—C(NH)$NH_2$, —NH—C(S)$NH_2$, phenyl, hydroxyphenyl, imidazolyl, indolyl; and $R_8$ is —H—, ($C_1$–$C_6$) alkyl, ($C_2$–$C_6$) alkenyl, ($C_2$–$C_6$) alkynyl.

22. The method of claim 19, wherein n is an integer from 1 to 3;

X is —S—, —O—, —NH— or —$CH_2$—; and $R_1$ and $R_2$ taken together are —$CH_2$—($CH_2$)$_b$—$CH_2$—, where b is an integer from 0 to 6.

23. The method of claim 1 wherein said compound has the formula:

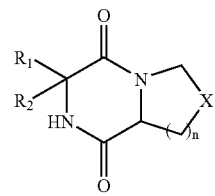

wherein

X is —$CH_2$—;

n is 1;

$R_1$ is H;

$R_2$ is ($CH_2$)$_q$$R_{18}$, q is 0, 1, 2, 3 or 4; and $R_{18}$ is di-t-butylhydroxyphenyl.

24. The method of claim 23 wherein $R_{18}$ is 3,5-di-t-butyl-4 hydroxy phenyl.

25. The method of claim 24 wherein q is 1.

26. The method of claim 23 wherein said compound has the formula:

wherein
X is —CH$_2$—;
n is 1;
R$_1$ is H, and
R$_2$ is (CH$_2$)$_q$R$_{18}$;
q is 0, 1, 2, 3, or 4; and
R$_{18}$ is di-t-butylhydroxyphenyl.

27. The method of claim 26 wherein R$_{18}$ is 3,5-di-t-butyl-4-hydroxyphenyl.

28. The method of claim 27 wherein q is 1.

29. The method of claim 7, wherein said compound has the formula:

wherein
X is —CH$_2$—;
n is 1;
R$_1$ is H;
R$_2$ is (CH$_2$)$_q$R$_{18}$,
q is 0, 1, 2, 3 or; and
R$_{18}$ is di-t-butylhydroxyphenyl.

30. The method of claim 29 wherein R$_{18}$ is 3,5-di-t-butyl-4-hydroxyphenyl.

31. The method of claim 30 wherein q is 1.

32. The method of claim 7 wherein said compound has the formula:

wherein
X is —CH$_2$—;
n is 1
R$_1$ is H and
R$_2$ is (CH$_2$)$_q$R$_{18}$;
q is 0, 1, 2, 3, or 4
R$_{18}$ is di-t-butylhydroxy phenyl.

33. The method of claim 32 wherein R$_8$ is 3,5-di-t-butyl-4-hydroxyphenyl.

34. The method of claim 33 wherein q is 1.

35. The method of claim 16 wherein R$_6$ is t-butyl.

36. The method of claim 20 wherein R$_6$ is t-butyl.

* * * * *